United States Patent
Jamal

(10) Patent No.: US 12,077,604 B2
(45) Date of Patent: *Sep. 3, 2024

(54) DEUTERATED COMPOUNDS, COMPOSITIONS, AND METHODS FOR TREATING CANCERS ASSOCIATED WITH ETBR ACTIVATION

(71) Applicant: ENB Therapeutics Inc., New York, NY (US)

(72) Inventor: Sumayah Jamal, New York, NY (US)

(73) Assignee: ENB Therapeutics, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/350,497

(22) Filed: Jun. 17, 2021

(65) Prior Publication Data

US 2021/0309694 A1 Oct. 7, 2021

Related U.S. Application Data

(63) Continuation of application No. 16/526,862, filed on Jul. 30, 2019, now Pat. No. 11,066,442, which is a continuation of application No. 16/246,398, filed on Jan. 11, 2019, now Pat. No. 10,435,434.

(60) Provisional application No. 62/616,729, filed on Jan. 12, 2018.

(51) Int. Cl.
| C07K 5/02 | (2006.01) |
| A61K 38/17 | (2006.01) |
| A61P 35/00 | (2006.01) |
| C07B 59/00 | (2006.01) |
| C07K 5/083 | (2006.01) |

(52) U.S. Cl.
CPC .............. *C07K 5/02* (2013.01); *A61K 38/177* (2013.01); *A61P 35/00* (2018.01); *C07B 59/002* (2013.01); *C07K 5/0808* (2013.01); *C07B 2200/05* (2013.01)

(58) Field of Classification Search
CPC .... A61P 35/00; A61P 37/02; A61K 2039/505; A61K 38/00; C07K 14/57536
See application file for complete search history.

(56) References Cited

U.S. PATENT DOCUMENTS

| 4,522,811 | A | | 6/1985 | Eppstein et al. | |
| 5,496,928 | A | | 3/1996 | Ishikawa et al. | |
| 6,545,048 | B1 | * | 4/2003 | Patterson | G01N 33/574 |
| | | | | | 514/564 |
| 7,566,452 | B1 | * | 7/2009 | Schneider | A61K 31/7088 |
| | | | | | 424/156.1 |
| 7,713,440 | B2 | | 5/2010 | Anderson | |
| 7,976,835 | B2 | | 7/2011 | Gulati | |
| 8,067,000 | B2 | * | 11/2011 | Schneider | G01N 33/57407 |
| | | | | | 514/19.2 |
| 8,597,645 | B2 | * | 12/2013 | Schneider | G01N 33/74 |
| | | | | | 514/19.2 |
| 9,125,897 | B2 | * | 9/2015 | Schneider | C07K 14/57536 |
| 9,463,201 | B2 | | 10/2016 | Alster et al. | |
| 10,174,120 | B2 | | 1/2019 | Buckanovich et al. | |
| 10,435,434 | B2 | * | 10/2019 | Jamal | A61P 35/00 |
| 10,695,400 | B2 | * | 6/2020 | Jamal | A61K 31/4025 |
| 11,066,442 | B2 | * | 7/2021 | Jamal | C07K 5/02 |
| 11,338,014 | B2 | * | 5/2022 | Jamal | A61K 38/16 |
| 2006/0122180 | A1 | | 6/2006 | Boyle et al. | |
| 2008/0102451 | A1 | | 5/2008 | Lesniewski et al. | |
| 2008/0305147 | A1 | | 12/2008 | Macdonald et al. | |
| 2009/0005394 | A1 | * | 1/2009 | Harbeson | C07C 309/86 |
| | | | | | 514/252.16 |
| 2009/0202507 | A1 | | 8/2009 | Li et al. | |
| 2009/0214518 | A1 | | 8/2009 | Buckanovich et al. | |
| 2011/0311525 | A1 | | 12/2011 | Herbert-Fransen et al. | |
| 2013/0216547 | A1 | | 8/2013 | Morton et al. | |
| 2013/0309253 | A1 | | 11/2013 | Schneider et al. | |
| 2014/0227260 | A1 | | 8/2014 | Zhang | |
| 2014/0341916 | A1 | | 11/2014 | Polakis et al. | |
| 2015/0190506 | A1 | | 7/2015 | Cheung et al. | |
| 2016/0257752 | A1 | | 9/2016 | Kim et al. | |
| 2017/0008971 | A1 | | 1/2017 | Dennis et al. | |
| 2017/0035836 | A1 | | 2/2017 | Jamal | |
| 2018/0030138 | A1 | | 2/2018 | Kowanetz | |
| 2018/0037655 | A1 | | 2/2018 | Hegde et al. | |
| 2019/0218251 | A1 | | 7/2019 | Jamal | |
| 2019/0314444 | A1 | | 10/2019 | Jamal | |
| 2019/0345197 | A1 | | 11/2019 | Jamal | |

(Continued)

FOREIGN PATENT DOCUMENTS

| EP | 0555537 A2 | 8/1993 |
| JP | S63250341 A | 10/1988 |

(Continued)

OTHER PUBLICATIONS

Saharsh Davuluri. API Manufacture of Deuterated Molecules. https://www.neulandlabs.com/blog/2016/12/04/api-manufacture-deuterated-molecules/ (Year: 2016).*

Lin et al. PD-1 Antibody Monotherapy for Malignant Melanoma: A Systematic Review and Meta-Analysis. PLoS ONE. 2016; 11(8): e0160485. (Year: 2016).*

Peng et al. PD-1 Blockade Enhances T Cell Migration to Tumors by Elevating IFN-γ Inducible Chemokines. Cancer Res. Oct. 15, 2012; 72(20): 5209-5218. (Year: 2012).*

Pimenta et al. Role of Tertiary Lymphoid Structures (TLS) in Anti-Tumor Immunity: Potential Tumor-Induced Cytokines/Chemokines that Regulate TLS Formation in Epithelial-Derived Cancers. Cancers 2014, 6, 969-997. (Year: 2014).*

(Continued)

*Primary Examiner* — Aradhana Sasan
*Assistant Examiner* — Jia-Hai Lee
(74) *Attorney, Agent, or Firm* — Goodwin Procter LLP

(57) ABSTRACT

Disclosed herein are deuterated compounds, pharmaceutical compositions thereof, and methods for treating ETBR-related cancers. Also disclosed herein is a delivery system for the controlled, systemic release of at least one deuterated ETBR antagonist, optionally in conjunction with an additional anti-oncologic agent.

13 Claims, 18 Drawing Sheets

Specification includes a Sequence Listing.

(56) References Cited

U.S. PATENT DOCUMENTS

| | | |
|---|---|---|
| 2020/0268829 A1 | 8/2020 | Jamal |
| 2020/0289495 A1 | 9/2020 | Jamal |
| 2020/0316046 A1 | 10/2020 | Jamal |
| 2020/0316049 A1 | 10/2020 | Jamal |
| 2021/0077562 A1 | 3/2021 | Jamal |
| 2021/0309694 A1 | 10/2021 | Jamal |
| 2022/0257700 A1 | 8/2022 | Jamal |

FOREIGN PATENT DOCUMENTS

| | | |
|---|---|---|
| JP | 2001519355 A | 10/2001 |
| WO | WO-1999018120 A1 | 4/1999 |
| WO | WO-0067024 A1 | 11/2000 |
| WO | WO-0100198 A2 | 1/2001 |
| WO | WO-2004035057 A1 | 4/2004 |
| WO | WO-2011019630 A2 | 2/2011 |
| WO | WO-2013127004 A1 | 9/2013 |
| WO | WO-2014025837 A1 | 2/2014 |
| WO | WO-2015110593 A1 | 7/2015 |
| WO | WO-2016196381 A1 | 12/2016 |
| WO | WO-2017024032 A2 | 2/2017 |
| WO | WO-2017151502 A1 | 9/2017 |
| WO | WO-2017165491 A1 | 9/2017 |
| WO | WO-2019140324 A1 | 7/2019 |
| WO | WO-2019191721 A1 | 10/2019 |
| WO | WO-2021011925 A1 | 1/2021 |

OTHER PUBLICATIONS

American Cancer Society. Cancer Facts & Figures 2015. Atlanta: American Cancer Society (2015).
Asundi, et al. MAPK pathway inhibition enhances the efficacy of an anti-endothelin B receptor drug conjugate by inducing target expression in melanoma. Mol Cancer Ther, 13 (6): 1599-610 (2014).
Bacon et al. Serodiagnosis of Lyme disease by kinetic enzyme-linked immunosorbent assay using recombinant VlsE1 or peptide antigens of Borrelia burgdorferi compared with 2-tiered testing using whole-cell lysates. J Infect Dis 187:1187-99 (2003).
Bagnato et al. Endothelin B receptor blockade inhibits dynamics of cell interactions and communications in melanoma cell progression. Cancer Res 64:1436-1443 (2004).
Bagnato et al. Endothelin receptors as novel targets in tumor therapy. J Transl Med 2:16, pp. 1-9 (2004).
Baker et al. Inhibitory effects of deuterium substitution on the metabolism of sevoflurane by the rat. Drug Metabolism and Disposition 21:1170-1171 (1993).
Beatty, G.L., et al. Chimeric receptor T cells are vulnerable to immunosuppressive mechanisms present within the tumor microenvironment, OncoImmunology, 3(11): e970027, (2014).
Bittner et al. Molecular classification of cutaneous malignant melanoma by gene expression profiling. Nature 406:536-540 (2000).
Buckanovich et al. Endothelin B receptor mediates the endothelial barrier to T cell homing to tumors and disables immune therapy. Nature Medicine 14:28-36. (2008).
Böhm et al. Diffuse melanosis arising from metastatic melanoma: pathogenetic function of elevated melanocyte peptide growth factors. J Am Acad Dermatol 44:747-754 (2001).
Chapman et al. Improved survival with vemurafenib in melanoma with BRAF V600E mutation. New Engl J of Med 364(26):2507-2516 (2011).
Chiriboga et al. Endothelin-1 in the tumor microenvironment correlates with melanoma invasion. Melanoma Research 26(3):236-244 (2016).
ClinicalTrials.gov, NCT00730639 first posted Aug. 8, 2008.
ClinicalTrials.gov, NCT01024231 first posted Dec. 2, 2009.
ClinicalTrials.gov, NCT01295827 first posted Feb. 15, 2011.
ClinicalTrials.gov, NCT01375842 first posted Jun. 17, 2011.
ClinicalTrials.gov, NCT01721772 first posted Nov. 6, 2012.
Coffman et al. Endothelin receptor-A is required for the recruitment of antitumor T cells and modulates chemotherapy induction of cancer stem cells. Cancer Biology & Therapy 14(2):184-192 (2013).
Cruz-Munoz, W., et al., Roles for endothelin receptor B and BCL2A1 in spontaneous CNS metastasis of melanoma, Cancer Res, 72(19): 4909-4919 (2012).
De Tayrac et al. Prognostic significance of EDN/RB, HJURP, p60/CAF-1 and PDLI4, four new markers in high-grade gliomas. PLOS One 8:e73332 (2013).
Deeks, Nivolumab: a review of its use in patients with malignant melanoma. Drugs 74:1233-1239 (2014).
Duraiswamy et al. Therapeutic PD-1 pathway blockade augments with other modalities of immunotherapy T-cell function to prevent immune decline in ovarian cancer. Cancer Research 73:6900-6912. (2013).
Egidy, G., et al. The Endothelin System in Human Glioblastoma, Laboratory Investigation, 80(11): 1681-1689, (2000).
Ehrenreich et al. Potent stimulation of monocytic endothelin-1 production by HIV-1 glycoprotein 120. J Immunol, 150:4601-4609 (1993).
Embers et al. Dominant epitopes of the C6 diagnostic peptide of Borrelia burgdorferi are largely inaccessible to antibody on the parent VISE molecule. Clin Vaccine Immunol 14:931-6 (2007).
Eton, O., et al., "Active Immunotherapy with Ultraviolet B-irradiated Autologous Whole Melanoma Cells plus DETOX in Patients with Metastatic Melanoma", Critical Cancer Research, Vo. 4, pp. 619-627, (Mar. 1998).
Fife et al. Determinants of outcome in melanoma patients with cerebral metastases. J Clin Oncol 22(7): 1293-1300 (2004).
Gangadhar et al. Clinical applications of PD-1-based therapy: a focus on pembrolizumab (MK-3475) in the management of melanoma and other tumor types. Oncotargets And Therapy, 8: 929-937 (2015).
Gide, T.N., et al., Primary and acquired resistance to immune checkpoint inhibitors in metastatic melanoma, Clin Cancer Res, 24(6):1260-1270 (2018).
Gray-Schopfer et al. The role of B-RAF in melanoma. Cancer Metastasis Rev 24:165-183 (2005).
Greish, Enhanced permeability and retention of macromolecular drugs in solid tumors: a royal gate for targeted anticancer nanomedicines. J Drug Target 15(7-8): 457-464 (2007).
How Significant Can Keytruda Be For Merck? Forbes (3 pgs) (Oct. 2014) http://www.forbes.com/sites/greatspeculations/2014/10/03/how-significant-can-keytruda-be-for-merck/.
Howlader et al. SEER Cancer Statistics Review, 1975-2012, National Cancer Institute. Bethesda, MD. Available at http://seer.cancer.gov/archive/csr/1975_2012/ (4 pgs) (2015).
Huang, X., et al., Transdermal BQ-788/EA@ZnO quantum dots as targeting and smart tyrosinase inhibitors in melanocytes, Mater Sci Eng C Mater Biol Appl, 102: 45-52 (2019).
Imokawa et al. The role of endothelin-1 in epidermal hyperpigmentation and signaling mechanisms of mitogenesis and melanogenesis. Pigment Cell Res 10:218-228 (1997).
Ishikawa et al. Biochemical and pharmacological profile of a potent and selective endothelin B-receptor antagonist, BQ-788. PNAS USA 91(11): 4892-4896 (1994).
Ishikawa et al. Cyclic pentapeptide endothelin antagonists with high ETA selectivity. Potency- and solubility-enhancing modifications. Journal of Medicinal Chemistry 35(11): 2139-2142 (1992).
Jamal et al. UV-induction of keratinocyte endothelin-1 downregulates E-cadherin in melanocytes and melanoma cells. J Clin Invest 110(4): 443-452 (2002).
Jamal, Endothelin-1 down-regulates E-cadherin in melanocytic cells by apoptosis-independent activation of caspase-8, J Am Acad Dermatol, 43(4): 703-704 (2000).
Johnstrom et al. Positron emission tomography using 18F-labelled endothelin-1 reveals prevention of binding to cardiac receptors owing to tissue-specific clearance by ETB receptors in vivo. Br J Pharmacol 144(1):115-122 (2005).
Jones, G.W., et al., Understanding immune cells in tertiary lymphoid organ development: It is all starting to come together, Front Immunol. 7: 401 (2016).
Kamino et al. Immunoperoxidase technique modified by counterstain with azure B as a diagnostic aid in evaluating heavily pigmented melanocytic neoplasms. J Cutan Pathol 18:436-439 (1991).

(56) References Cited

OTHER PUBLICATIONS

Kandalaft, L.E., et al., Endothelin B receptor, a new target in cancer immune therapy, Clin Cancer Res, 15(14): 4521-4528 (2009).
Karaki et al. Novel antagonist of endothelin ETB1 and ETB2 receptors, BQ-788: effects on blood vessel and small intestine. Biochem Biophys Res Commun. 205:168-173 (1994).
Kim et al. Effective treatment of glioblastoma requires crossing the blood-brain barrier and targeting tumors including cancer stem cells: The promise of nanomedicine. Biochem Biophys Res Commun. 468:485-489 (2015).
Kitadai, T., et al., "Targeting the Expression of Platelet-Derived Growth Factor Receptor by Reactive Stroma Inhibits Growth and Metastasis of Human Colon Carcinoma", American Journal of Pathology, 169:6, pp. 2054-2065 (Dec. 2006).
Lahav et al. An endothelin receptor B antagonist inhibits growth and induces cell death in human melanoma cells in vitro and in vivo. PNAS USA 96(20):11496-11500 (1999).
Lahav et al. Endothelin receptor B inhibition triggers apoptosis and enhances angiogenesis in melanomas, Cancer Res 64: 8945-8953 (2004).
Liang et al. An immunodominant conserved region within the variable domain of VlsE, the variable surface antigen of Borrelia burgdorferi. J Immunol 163:5566-5573 (1999).
Liang et al. Sensitive and specific serodiagnosis of Lyme disease by enzyme-linked immunosorbent assay with a peptide based on an immunodominant conserved region of Borrelia burgdorferi vlsE. J Clin Microbiol 37:3990-6 (1999).
Liu et al. Autocrine endothelin-3/endothelin receptor B signaling maintains cellular and molecular properties of glioblastoma stem cells, Mol Cancer Res, 9(12): 1668-1685 (2011).
Mahoney, K.M., et al., The next immune-checkpoint inhibitors: PD-1/PD-L1 blockade in melanoma, Clin Ther, 37(4): 764-782 (2015).
Mangahas et al. Endothelin-1 induces CXCL1 and CXCL8 secretion in human melanoma cells. J Invest Dermatol 125:307-311 (2005).
Mangahas et al. Endothelin-1 upregulates MCAM in melanocytes. J Invest Dermatol 123:1135-1139 (2004).
Medina et al. Dabrafenib in the treatment of advanced melanoma. Drugs of Today 49(6):377-385 (2013).
Moretti et al. Immunohistochemical evidence of cytokine networks during progression of human melanocytic lesions. Int J Cancer, 84:160-168 (1999).
Nakashima, S., et al., Endothelin B receptor expression in malignant gliomas: the perivascular immune escape mechanism of gliomas, J Neurooncol, 127(1): 23-32 (2016).
Nelson et al. The endothelin axis: emerging role in cancer, Nat Rev Cancer 3(2): 110-116 (2003).
Okada, BQ-788, a selective endothelin ET(B) receptor antagonist. Cardiovascular drug reviews 20(1):53-66 (2002).
Okazawa, M., et al. Endothelin-induced Apoptosis of A375 Human Melanoma Cells, J Biol Chem, 273(20): 12584-12592 (1998).
Ott, P.A., et al., CTLA-4 and PD-1/PD-L1 blockade: new immunotherapeutic modalities with durable clinical benefit in melanoma patients, Clin Cancer Res, 19(19): 5300-5309 (2013).
Pardoll, D.M. The blockade of immune checkpoints in cancer immunotherapy, Nature, 12: 252-264, (2012).
Pardoll, D.M., et al., The blockade of immune checkpoints in cancer immunotherapy, Nat Rev Cancer, 12(4): 252-264 (2012).
Park, J., et al., Immune checkpoint inhibitors for cancer treatment, Arch Pharm Res, 39(11): 1577-1587 (2016).
PCT/US2016/45343 International Search Report and Written Opinion dated Feb. 17, 2017.
PCT/US2019/013377 International Search Report and Written Opinion dated May 8, 2019.
PCT/US2019/013377 Invitation to Pay Additional Fees dated Mar. 12, 2019.
PCT/US2019/025050 International Search Report and Written Opinion dated Aug. 12, 2019.
PCT/US2019/025050 Invitation to Pay Additional Fees dates Jun. 7, 2019.
PCT/US2020/042673 International Search Report and Written Opinion dated Dec. 7, 2020.
Rizvi et al. Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol 16(3):257-265 (2015).
Rosario et al. Endothelin receptor blockade inhibits molecular effectors of Kaposi's sarcoma cell invasion and tumor growth in vivo, Am J Pathol, 163(2): 753-762 (2003).
Ross et al. Systematic variation in gene expression patterns in human cancer cell lines. Nat Genet 24:227-235 (2000).
Saldana-Caboverde et al. Roles in endothelin signaling in melanocyte development and melanoma, Pigment Cell and Melanoma Res. 23(2):160-170 (2010).
Saldanha et al. High BRAF mutation frequency does not characterize all melanocytic tumor types. Int J Cancer 111:705-710 (2004).
Samlowski et al. Management of brain metastases in melanoma, Up To Date literature review. http://www.uptodate.com/contents/management-of-brain-metastases-in-melanoma. (5 pgs) (2016).
Sampson et al. Demographics, prognosis, and therapy in 702 patients with brain metastases from malignant melanoma. J Neurosurg 88:11 (1998).
Sampson, J.H., et al., Randomized phase IIb study of Nivolumab (anti-PD-1; BMS-936558, ONO-4538) alone or in combination with ipilimumab versus bevacizumab in patients (pts) with recurrent glioblastoma (GBM), J Clin Oncol, 32(15): Abstract, (2014).
Sautes-Fridman, C., et al., Tertiary lymphoid structures in the era of cancer immunotherapy, Nat Rev Cancer, 19(6): 307-325 (2019).
Seiwert, T.Y., et al., Antitumor activity and safety of pembrolizumab in patients (pts) with advanced squamous cell carcinoma of the head and neck (SCCHN): Preliminary results from KEYSOTE-012 expansion cohort, J Clin Oncol, 33(18 spp): LBA6008 (Abstract) (2005).
Sharma et al. The future of immune checkpoint therapy. Science 348:56-61 (2015).
Singh, R.K., et al., Organ site-dependent expression of basic fibroblast growth factor in human renal cell carcinoma cells, Am J Pathol, 145(2): 365-374 (1994).
Sosman, Immunotherapy of advanced melanoma with immune checkpoint inhibition, Up To Date literature review. http://www.uptodate.com/contents/immunotherapy-of-advanced-melanoma-with-immune-checkpoint-inhibition. (12 pgs.) (2016).
Sosman, Molecularly targeted therapy for metastatic melanoma, Up to Date Literature review http://www.uptodate.com/contents/molecularly-targeted-therapy-for-metastatic-melanoma. (11 pgs.) (2016).
Steiniger, S.C.J., et al., Chemotherapy of glioblastoma in rats using doxorubicin-loaded nanoparticles, Int J Cancer, 109: 759-767 (2004).
Takahashi, Molecular-target therapy for advanced malignant melanoma. Japanese Journal of Cancer and Chemotherapy 40(1): 19-25 (2013) (English Summary).
Tang et al. Endothelin-3 is produced by metastatic melanoma cells and promotes melanoma cell survival, J Cutan Med and Surg, 12(2): 64-70 (2008).
Terrades-Garcia et al. Pathogenesis of giant-cell arteritis: how targeted therapies are influencing our understanding of the mechanisms involved. Rheumatology (Oxford) 57(supp 2):ii51-ii62 (2018).
Topalian et al. Immune checkpoint blockade: a common denominator approach to cancer therapy. Cancer Cell 27:450-461 (2015).
U.S. Appl. No. 15/227,792 Office Action dated Nov. 15, 2019.
U.S. Appl. No. 15/227,792 Office Action dated Sep. 21, 2018.
U.S. Appl. No. 16/246,398 First Action Interview dated Apr. 8, 2019.
U.S. Appl. No. 16/419,931 Office Action dated Jan. 13, 2020.
U.S. Appl. No. 16/419,931 Office Action dated Jul. 24, 2020.
U.S. Appl. No. 16/526,862 Office Action dated Jan. 7, 2021.
U.S. Appl. No. 16/828,895 Office Action dated Dec. 2, 2020.
U.S. Appl. No. 16/828,895 Office Action dated Jun. 30, 2020.
U.S. Appl. No. 16/828,895 Office Action dated Mar. 3, 2021.
U.S. Appl. No. 16/828,900 Office Action dated Jun. 25, 2020.
U.S. Appl. No. 16/828,900 Office Action dated Nov. 10, 2020.
U.S. Appl. No. 16/828,911 Office Action dated Dec. 1, 2020.
U.S. Appl. No. 16/828,911 Office Action dated May 29, 2020.

(56) References Cited

OTHER PUBLICATIONS

Voronin, K., Deuteriodesilylation: a mild and selective method for the site-specific incorporation of deuterium into drug candidates and pharmaceutical structures. Thesis (132 pgs) (2012).

Yohn, J.J., et al. Human melanoma cells express functional endothelin-1 receptors, Biochem Biophys Res Commun, 201:449-457 (1994).

Brosseau, J-P, et al., Development of an efficient strategy for the synthesis of the ETB receptor antagonist BQ-788 and some related analogues, Peptides, 26(8): 1441-1453 (2005).

Fukami, T., et al., Synthesis and structure—Activity relationships of 2-Substituted d-Tryptophan-containing peptidic endothelin receptor antagonists: Importance of the C-2 substituent of the d-Tryptophan residue for endothelin A and B receptor subtype selectivity, J Med Chem, 39(12): 2313-2330 (1996).

Fukami, T., et al., Synthesis of 2-substituted d-tryptophan-containing peptide derivatives with endothelin receptor antagonist activity, Bioorg Med Chem Lett, 5(14): 1483-1488 (1995).

He, J.X., et al., An efficient preparation of the pseudopeptide endothelin-B receptor selective antagonist BQ-788, J Org Chem, 60: 8262-8266 (1995).

Nagase, T., et al., Linear peptide $ET_A$ antagonists: Rational design and practical derivitization of N-terminal amino- and imino-carboylated tripeptide derivatives, Bioorg Med Chem Lett, 5(13): 1395-1400 (1995).

U.S. Appl. No. 17/101,676 Office Action dated Oct. 6, 2022.

Allard, B., et al., Generation and characterization of rendomab-B1, a monoclonal antibody displaying potent and specific antagonism of the human endothelin B receptor, MAbs, 5(1): 56-69 (2013).

U.S. Appl. No. 16/828,895 Office Action dated Sep. 15, 2021.

Budi, H.S., et al., Human epidermal growth factor receptor 2 (HER2)-specific chimeric antigen receptor (CAR) for tumor immunotherapy; recent progress, Stem Cell Res Ther, 13: 40, pp. 1-21 (2022).

Montgomery, J.P., et al., Endothelin receptor B antagonists decrease glioma cell viability independently of their cognate receptor, BMC Cancer, 8:354 (2008).

PCT/US2023/078095 International Search Report and Written Opinion mailed Mar. 5, 2024.

Tóth, G., et al., A Small Number of HER2 Redirected CAR T Cells Significantly Improves Immune Response of Adoptively Transferred Mouse Lymphocytes against Human Breast Cancer Xenografts, Int J Mol Sci, 21(3): 1039, pp. 1-10 (2020).

Wulfing, C., et al., Expression of the endothelin axis in bladder cancer: relationship to clinicopathologic parameters and long-term survival, Eur Urol, 47(5): 593-600 (2005).

* cited by examiner

FIG. 10
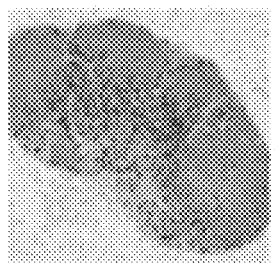
CD8
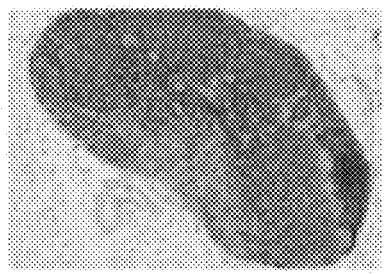
CD4
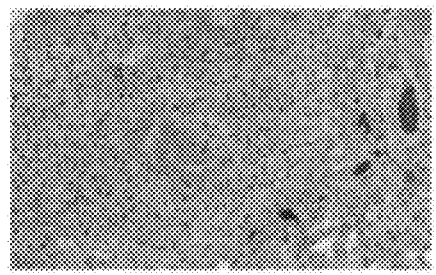
FoxP3

|  | Group # | Animal # | TLO formation | Tumor eradication |
|---|---|---|---|---|
| control | Group 1 | 6 | no | no |
|  |  | 23 | no | no |
|  |  | 28 | no | no |
|  |  | 29 | no | no |
|  |  | 33 | no | no |
| D+P | Group 2 | 3 | no | no |
|  |  | 10 | no | no |
|  |  | 17 | tlo peripheral | no |
|  |  | 32 | no | no |
|  |  | 35 | no | no |
| D+P+B (0.6 μg) | Group 3 | 5 | no | no |
|  |  | 13 | no | no |
|  |  | 20 | tumor undetectable |  |
|  |  | 24 | no | no |
|  |  | 31 | no | 25% |

|  | Group # | Animal # | TLO formation | Tumor eradication |
|---|---|---|---|---|
| D+P+B (4.0 μg) | Group 4 | 1 | no | no |
|  |  | 19 | tlo peripheral | no |
|  |  | 21 | no | no |
|  |  | 26 | tlo peripheral | no |
|  |  | 27 | tlo internal | 90% |
| D+P+B (100 μg) | Group 5 | 8 | no | no |
|  |  | 14 | tlo internal | 80% |
|  |  | 16 | no | no |
|  |  | 22 | no | no |
|  |  | 25 | no | no |
| P+B (4.0 μg) | Group 6 | 7 | tumor undetectable |  |
|  |  | 9 | tlo internal | 90% |
|  |  | 12 | no | 100% |
|  |  | 38 | tlo internal | 90% |
|  |  | 40 | tlo internal | 50% |

D = dabrafenib    P = immunocheckpoint inhibitor    B = BQ-788-B (dosage)

D = dabrafenib
P = anti-PD1
B = BQ-788-B (dosage)

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (20)..(20)
<223> OTHER INFORMATION: Carboxylation

<400> SEQUENCE: 1

Ala Ala Val Ala Leu Leu Pro Ala Val Leu Leu Ala Ala Leu Ala Pro
1               5                   10                  15

Ile Glu Thr Asp
            20
```

DEUTERATED COMPOUNDS, COMPOSITIONS, AND METHODS FOR TREATING CANCERS ASSOCIATED WITH ETBR ACTIVATION

CROSS-REFERENCE

This application is a continuation of U.S. application Ser. No. 16/526,862, filed on Jul. 30, 2019, which is a continuation of U.S. application Ser. No. 16/246,398, filed Jan. 11, 2019, now issued as U.S. Pat. No. 10,435,434 on Oct. 8, 2019, which claims the benefit of U.S. Provisional Application No. 62/616,729, filed Jan. 12, 2018, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Mar. 23, 2021, is named "ENB_003C2_SL.txt" and is 823 bytes in size.

BRIEF SUMMARY

Disclosed herein are compounds. In some embodiments, a compound can be a compound of Formula (1):

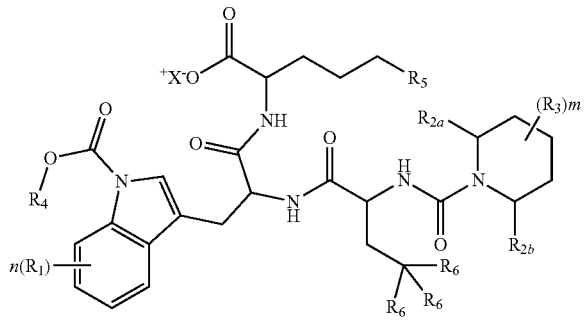

Formula (1)

a stereoisomer thereof, or a pharmaceutically acceptable salt thereof, where: n can be an integer from 0-5; m can be an integer from 0-3; X can be a positively charged counterion; $R_1$ and $R_3$ can be independently —H, -D, —$CH_3$, —$CH_2D$, —$CHD_2$, or —$CD_3$; $R_{2a}$, $R_{2b}$, $R_4$, $R_5$, and $R_6$ can be independently —$CH_3$, —$CH_2D$, —$CHD_2$, or —$CD_3$; and at least one of $R_1$, $R_2$, or $R_3$ comprises deuterium. In some embodiments, m can be 0, n can be 0, and $R_{2a}$ and $R_{2b}$ can be —$CH_2D$. In some embodiments, a compound can be a compound of Formula (2):

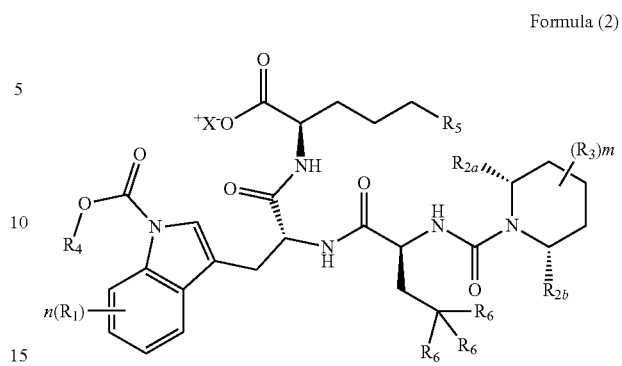

Formula (2)

or a pharmaceutically acceptable salt thereof. In some embodiments, a compound can be a compound of Formula (3):

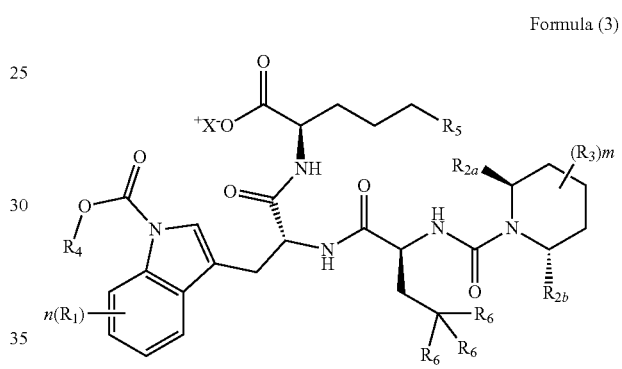

Formula (3)

or a pharmaceutically acceptable salt thereof. In some embodiments, a compound can be a compound of Formula (4):

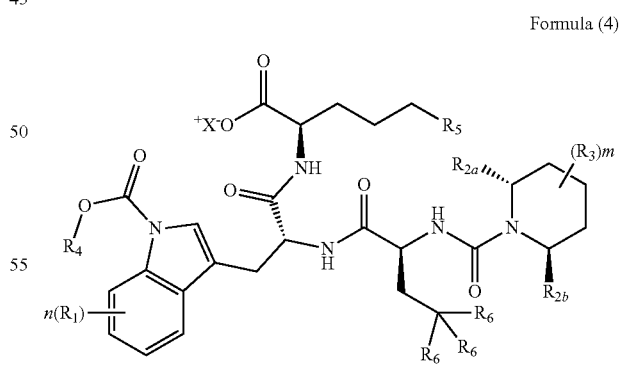

Formula (4)

or a pharmaceutically acceptable salt thereof. In some embodiments, a compound can be a compound of Formula (5):

Formula (5)

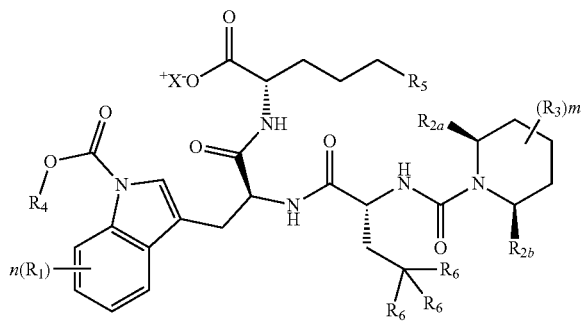

or a pharmaceutically acceptable salt thereof. In some embodiments, a compound can be a compound of Formula 6:

Formula (6)

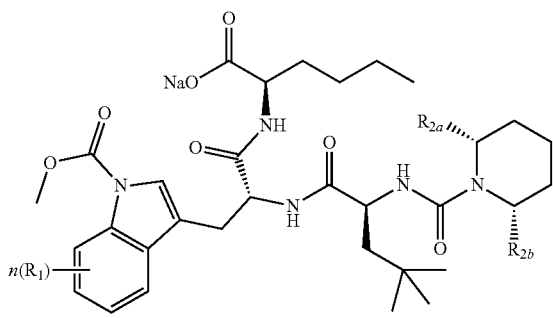

In some embodiments, n can be 0 or 1. In some embodiments, n can be 1, $R_1$ can be -D; and $R_{2a}$ and $R_{2b}$ can be —$CH_3$. In some embodiments, n can be 0, $R_1$ can be —H; $R_{2a}$ can be —$CH_3$ and $R_{2b}$ can be —$CH_2D$. In some embodiments, n can be 0, $R_1$ can be —H; $R_{2a}$ can be —$CH_2D$ and $R_{2b}$ can be —$CH_3$. In some embodiments, n can be 0, $R_1$ can be —H; and $R_{2a}$ and $R_{2b}$ can be —$CH_2D$. In some embodiments, n can be 1, $R_1$ can be -D; and $R_{2a}$ and $R_{2b}$ can be —$CH_2D$.

Also disclosed herein are compounds or pharmaceutically acceptable salts thereof selected from the group consisting of:

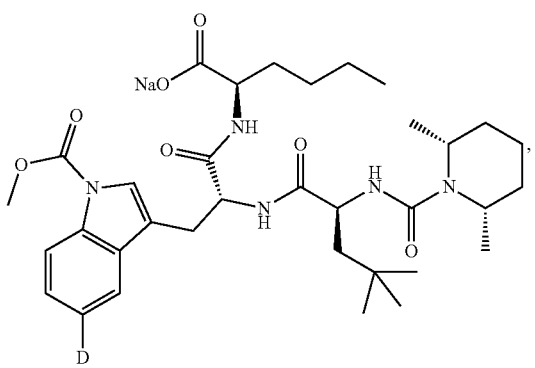

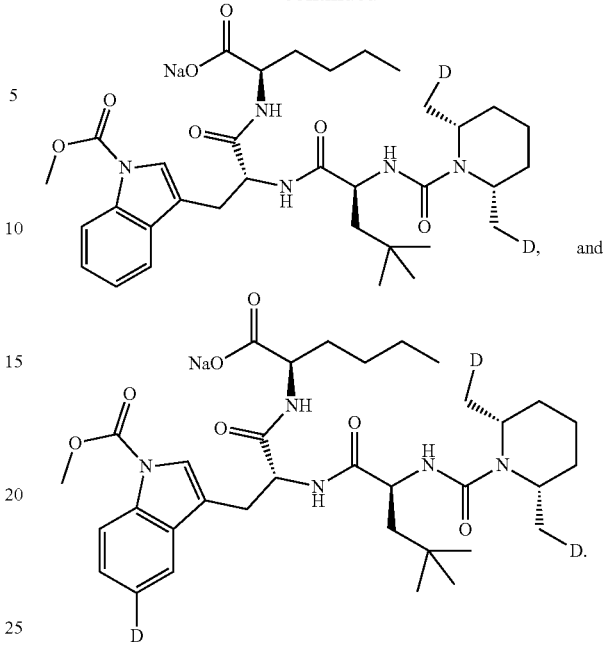

Also disclosed herein are pharmaceutical composition that comprises a compound as described herein and a pharmaceutically acceptable excipient, diluent, or carrier. In some embodiments, a pharmaceutical composition comprises a pharmaceutically acceptable carrier. In some embodiments, a pharmaceutically acceptable carrier can be dimethyl sulfoxide (DMSO). In some embodiments, the compound is:

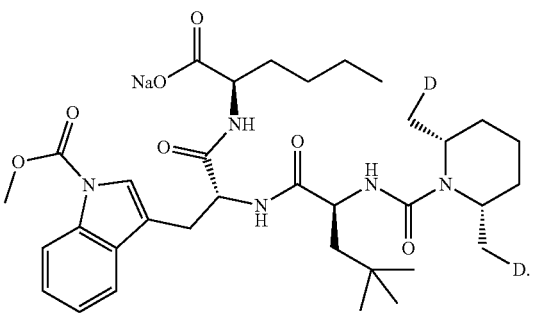

Also disclosed herein are methods of treating cancer that comprises administering to a subject in need thereof a pharmaceutical composition as described herein. In some embodiments, a method can further comprise administering an immune checkpoint inhibitor to the subject. In some embodiments, an immune checkpoint inhibitor can be an anti-PD1 antibody.

Also disclosed herein are methods of treating cancer in a subject in need thereof, that comprises administering to the subject a compound as described herein, wherein the compound can be in an amount effective for treating or ameliorating at least one symptom of the cancer in the subject. In some embodiments, a method can further comprise administering to the subject at least one immune checkpoint inhibitor to the subject. In some embodiments, the at least one immune checkpoint inhibitor comprises at least one anti-PD1 antibody, at least one anti-PD-L1 antibody, at least one anti-CTLA4 antibody, or any combination thereof. In some embodiments, the at least one anti-PD1 antibody comprises pidilizumab, BMS-936559, nivolumab, pembrolizumab or any combination thereof. In some embodiments, the at least one anti-PD-L1 antibody comprises atezolizumab, avelumab, durvalumab, MDX-1105, or any combination thereof. In some embodiments, the cancer can be a solid tumor cancer, malignant melanoma, metastatic melanoma, malignant squamous cell carcinoma, metastatic squamous cell carcinoma, glioblastoma, brain cancer, pancreatic cancer, colon cancer, breast cancer, ovarian cancer, prostate cancer, or any combination thereof. In some embodiments, the compound and the immune checkpoint inhibitor can be administered at different times. In some embodiments, the compound can be administered 2, 3, 4, or 5 times frequently as the immune checkpoint inhibitor. In some embodiments, the compound can be administered 3 times frequently as the immune checkpoint inhibitor. In some embodiments, the compound can be administered 3 times every 2-3 weeks and the immune checkpoint inhibitor can be administered 1 time the every 2-3 weeks. In some embodiments, the compound can be administered 3 times about every 21 days and the immune checkpoint inhibitor can be administered 1 time the about every 21 days. In some embodiments, the subject can be a human. In some embodiments, the subject can be resistant to an immunotherapy before the treatment. In some embodiments, the administration results in at least one of improved biologic activity, increased stability, prolonged serum bioavailability, prolonged ETBR target engagement, or any combination thereof, compared to a non-deuterated parent compound, as determined by measuring a serum ET-1 level. In some embodiments, the administration restores Tumor Infiltrating Lymphocytes (TILs), intratumoral tertiary lymphoid organ (TLO) formation, or a combination thereof, in a tumor microenvironment.

Also disclosed herein are methods of forming a tertiary lymphoid organ (TLO) within a tumor in a subject in need thereof, that comprises administering to the subject a compound as described herein, whereby the tumor can be reduced or eradicated. In some embodiments, the compound is

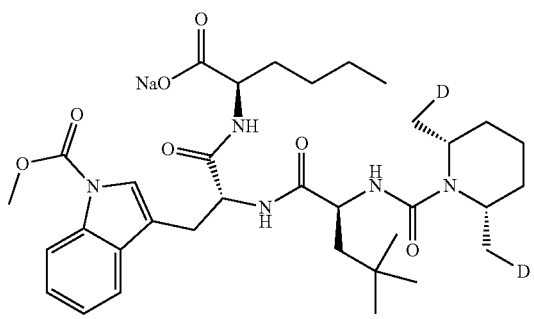

a stereoisomer thereof, or a pharmaceutically acceptable salt thereof. In some embodiments, the compound can be in a pharmaceutically acceptable excipient that comprises dimethyl sulfoxide (DMSO).

Also disclosed herein are compounds of Formula (7):

Formula (7)

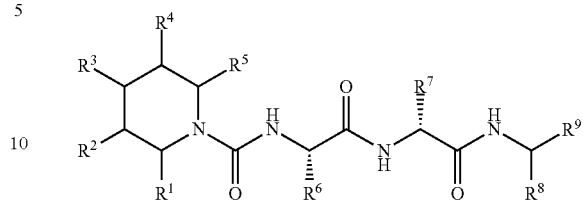

a stereoisomer thereof, or a pharmaceutically acceptable salt thereof, where: $R^1$, $R^2$, $R^3$, $R^4$, or $R^5$ can be independently hydrogen, halogen, hydroxyl, deuterium, halogen, hydroxy, amino, nitro, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ haloalkykl, optionally substituted aryl, or optionally substituted heteroaryl, optionally wherein one or more of the carbons in the piperidinyl ring can be a heteroatom selected from O, N, or S, or wherein the piperidinyl ring may contain one or more double bonds; $R^6$ can be optionally substituted $C_1$-$C_8$ alkyl, optionally substituted $C_2$-$C_8$ alkenyl, optionally substituted $C_2$-$C_8$ alkynyl, optionally substituted $C_3$-$C_8$-cycloalkyl, optionally substituted $C_1$-$C_8$ alkoxy, optionally substituted $C_1$-$C_8$ haloalkykl, optionally substituted aryl, or optionally substituted heteroaryl, wherein $R^6$ optionally comprises deuterium; $R^7$ can be optionally substituted cycloalkyl, optionally substituted heterocycloalkyl, optionally substituted aryl, optionally substituted heteroaryl, optionally substituted polycyclic ring system, optionally substituted bicyclic, optionally substituted heterobycyclic, wherein $R^7$ optionally comprises deuterium; $R^8$ and $R^9$ can be independently optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ haloalkyl, optionally substituted aryl, optionally substituted heteroaryl, or —COOR', or $R^8$ and $R^9$ may be taken together to form a optionally substituted cycloalkyl, optionally substituted cycloalkyl heterocycloalkyl, optionally substituted aryl, optionally substituted heteroaryl, or optionally substituted polycyclic ring system, wherein $R^8$ or $R^9$ each optionally comprises deuterium; R' can be hydrogen, hydroxy, or $C_1$-$C_8$ alkyl; and wherein at least one of $R^1$, $R^2$, $R^3$, $R^4$, $R^5$, $R^6$, $R^7$, $R^8$, or $R^9$ comprises deuterium. In some embodiments, two of $R^1$, $R^2$, $R^3$, $R^4$, or $R^5$ comprise deuterium. Also disclosed herein are pharmaceutical compositions that comprise an effective amount of the compound, and a pharmaceutically acceptable carrier. In some embodiments, the pharmaceutically acceptable carrier can be dimethyl sulfoxide (DMSO). Also disclosed herein are methods of treating cancer in a subject in need thereof, that comprises administering to the subject the compound the pharmaceutical composition, wherein the method can be effective in treating or ameliorating at least one symptom of the cancer in the subject. In some embodiments, the method can further comprise administering to the subject at least one additional anti-oncologic therapeutic agent. In some embodiments, the at least one additional anti-oncologic agent comprises a bRAF inhibitor, an immune checkpoint inhibitor, a caspase-8 inhibitor, an ETAR antagonist, niacinamide, a chemotherapeutic agent, or any combination thereof. In some embodiments, the at least one additional anti-onco-logic agent comprises at least one of the immune checkpoint inhibitor. In some embodiments, the at least one immune checkpoint inhibitor comprises at least one anti-PD1 antibody, at least one anti-PD-L1 antibody, at least one anti-CTLA4 antibody, or any combination thereof. In some embodiments, the at least one anti-PD1 antibody comprises pidilizumab, BMS-936559, nivolumab, pembrolizumab or any combination thereof. In some embodiments, the at least one anti-PD-L1 antibody comprise atezolizumab, avelumab, durvalumab, MDX-1105, or any combination thereof. In some embodiments, the cancer can be a solid tumor cancer, malignant melanoma, metastatic melanoma, malignant squamous cell carcinoma, metastatic squamous cell carcinoma, glioblastoma, brain cancer, pancreatic cancer, colon cancer, breast cancer, ovarian cancer, prostate cancer, or any combination thereof. In some embodiments, the compound and the at least one additional anti-oncologic agent can be administered at different times. In some embodiments, the compound can be administered 2, 3, 4, or 5 times frequently as the immune checkpoint inhibitor. In some embodiments, the compound can be administered 3 times frequently as the immune checkpoint inhibitor. In some embodiments, the compound can be administered 3 times every 2-3 weeks and the immune checkpoint inhibitor can be administered 1 time the every 2-3 weeks. In some embodiments, the compound can be administered 3 times about every 21 days and the immune checkpoint inhibitor can be administered 1 time the about every 21 days. In some embodiments, the subject can be a human. In some embodiments, the subject can be resistant to an immunotherapy before the treatment. In some embodiments, the administration results in at least one of improved biologic activity, increased stability, prolonged serum bioavailability, prolonged ETBR target engagement, or any combination thereof, compared to a non-deuterated parent compound, as determined by measuring a serum ET-1 level. In some embodiments, the administration restores Tumor Infiltrating Lymphocytes (TILs), intratumoral tertiary lymphoid organ (TLO) formation, or a combination thereof, in a tumor microenvironment.

Also disclosed herein are compounds of Formula (8):

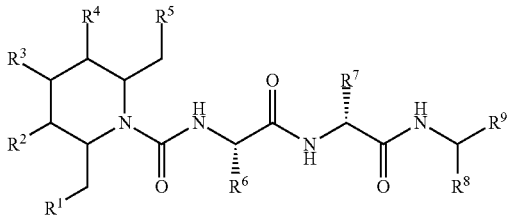

Formula (8)

a stereoisomer thereof, or a pharmaceutically acceptable salt thereof, where: $R^2$, $R^3$, or $R_4$ can be independently hydrogen, deuterium, halogen, hydroxy, amino, nitro, $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ haloalkykl, aryl, or heteroaryl; $R^6$ can be $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ haloalkykl, aryl, or heteroaryl, wherein $R^6$ optionally comprises deuterium; $R^7$ can be substituted or unsubstituted cycloalkyl, substituted or unsubstituted heterocycloalkyl, substituted or unsubstituted aryl, substituted or unsubstituted heteroaryl, or a substituted or unsubstituted polycyclic ring system, wherein $R^7$ optionally comprises deuterium; $R^8$ and $R^9$ can be independently $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, heteroaryl, or —COOR', or $R^8$ and $R^9$ may be taken together to form a substituted or unsubstituted cycloalkyl, substituted or unsubstituted cycloalkyl heterocycloalkyl, substituted or unsubstituted aryl, substituted or unsubstituted heteroaryl, or substituted or unsubstituted polycyclic ring system, wherein $R^8$ or $R^9$ each optionally comprises deuterium; R' can be hydrogen, hydroxy, or $C_1$-$C_8$ alkyl; and wherein at least one of $R^1$, $R^2$, $R^3$, $R^4$, $R^5$, $R^6$, $R^7$, $R^8$, or $R^9$ comprises deuterium. In some embodiments, two of $R^1$, $R^2$, $R^3$, $R^4$, or $R^5$ comprise deuterium. Also disclosed herein are pharmaceutical compositions that comprise an effective amount of the compound, and a pharmaceutically acceptable carrier. In some embodiments, the pharmaceutically acceptable carrier can be dimethyl sulfoxide (DMSO). Also disclosed herein are methods of treating cancer in a subject in need thereof, that comprises administering to the subject the compound the pharmaceutical composition, wherein the method can be effective in treating or ameliorating at least one symptom of the cancer in the subject. In some embodiments, the method can further comprise administering to the subject at least one additional anti-oncologic therapeutic agent. In some embodiments, the at least one additional anti-oncologic agent comprises a bRAF inhibitor, an immune checkpoint inhibitor, a caspase-8 inhibitor, an ETAR antagonist, niacinamide, a chemotherapeutic agent, or any combination thereof. In some embodiments, the at least one additional anti-oncologic agent comprises at least one of the immune checkpoint inhibitor. In some embodiments, the at least one immune checkpoint inhibitor comprises at least one anti-PD1 antibody, at least one anti-PD-L1 antibody, at least one anti-CTLA4 antibody, or any combination thereof. In some embodiments, the at least one anti-PD1 antibody comprises pidilizumab, BMS-936559, nivolumab, pembrolizumab or any combination thereof. In some embodiments, the at least one anti-PD-L1 antibody comprise atezolizumab, avelumab, durvalumab, MDX-1105, or any combination thereof. In some embodiments, the cancer can be a solid tumor cancer, malignant melanoma, metastatic melanoma, malignant squamous cell carcinoma, metastatic squamous cell carcinoma, glioblastoma, brain cancer, pancreatic cancer, colon cancer, breast cancer, ovarian cancer, prostate cancer, or any combination thereof. In some embodiments, the compound and the at least one additional anti-oncologic agent can be administered at different times. In some embodiments, the compound can be administered 2, 3, 4, or 5 times frequently as the immune checkpoint inhibitor. In some embodiments, the compound can be administered 3 times frequently as the immune checkpoint inhibitor. In some embodiments, the compound can be administered 3 times every 2-3 weeks and the immune checkpoint inhibitor can be administered 1 time the every 2-3 weeks. In some embodiments, the compound can be administered 3 times about every 21 days and the immune checkpoint inhibitor can be administered 1 time the about every 21 days. In some embodiments, the subject can be a human. In some embodiments, the subject can be resistant to an immunotherapy before the treatment. In some embodiments, the administration results in at least one of improved biologic activity, increased stability, prolonged serum bioavailability, prolonged ETBR target engagement, or any combination thereof, compared to a non-deuterated parent compound, as determined by measuring a serum ET-1 level. In some embodiments, the administration restores Tumor Infiltrating Lymphocytes (TILs), intratumoral tertiary lymphoid organ (TLO) formation, or a combination thereof, in a tumor microenvironment.

Also disclosed herein are compounds of Formula (9):

Formula (9)

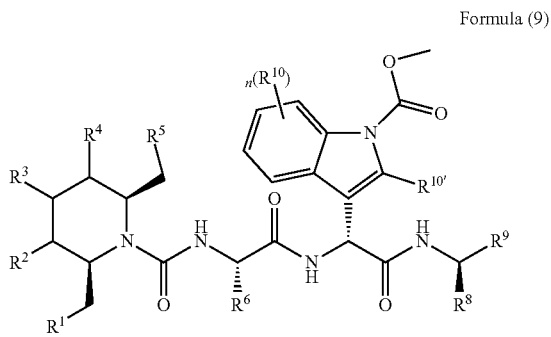

a stereoisomer thereof, or a pharmaceutically acceptable salt thereof, where: $R^1$ $R_2$, $R^3$, $R^4$, or $R^5$ can be independently hydrogen, deuterium, halogen, hydroxy, amino, nitro, $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ haloalkyl, aryl, or heteroaryl; $R^6$ can be $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, or heteroaryl, wherein $R^6$ optionally comprises deuterium; $R^8$ and $R^9$ can be independently $C_1$-$C_8$ alkyl, $C_2$-$C_8$ alkenyl, $C_2$-$C_8$ alkynyl, $C_3$-$C_8$ cycloalkyl, $R^8$ and $R^9$ can be independently $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, heteroaryl, or —COOR', or $R^8$ and $R^9$ may be taken together to form a substituted or unsubstituted cycloalkyl, substituted or unsubstituted cycloalkyl heterocycloalkyl, substituted or unsubstituted aryl, substituted or unsubstituted heteroaryl, or substituted or unsubstituted polycyclic ring system, wherein $R^8$ or $R^9$ each optionally comprises deuterium; $R^{10}$ and $R^{10'}$ can be independently hydrogen, deuterium, halogen, hydroxy, amino, nitro, $C_1$-$C_8$ alkyl, $C_2$-$C_8$ alkenyl, $C_2$-$C_8$ alkynyl, $C_3$-$C_8$-cycloalkyl, $C_1$-$C_8$ alkoxy, $C_1$-$C_8$ haloalkykl, aryl, or heteroaryl; n can be an integer from 0-4; and wherein at least one of $R^1$, $R^2$, $R^3$, $R^4$, $R^5$, $R^6$, $R^7$, $R^8$, $R^9$, $R^{10}$ or $R^{10'}$ comprises deuterium. In some embodiments, n can be 0 and both $R^{10}$ and $R^{10'}$ can be hydrogen. In some embodiments, two of $R^1$, $R^2$, $R^3$, $R^4$, or $R^5$ comprise deuterium. Also disclosed herein are pharmaceutical compositions that comprise an effective amount of the compound, and a pharmaceutically acceptable carrier. In some embodiments, the pharmaceutically acceptable carrier can be dimethyl sulfoxide (DMSO). Also disclosed herein are methods of treating cancer in a subject in need thereof, that comprises administering to the subject the compound the pharmaceutical composition, wherein the method can be effective in treating or ameliorating at least one symptom of the cancer in the subject. In some embodiments, the method can further comprise administering to the subject at least one additional anti-oncologic therapeutic agent. In some embodiments, the at least one additional anti-oncologic agent comprises a bRAF inhibitor, an immune checkpoint inhibitor, a caspase-8 inhibitor, an ETAR antagonist, niacinamide, a chemotherapeutic agent, or any combination thereof. In some embodiments, the at least one additional anti-oncologic agent comprises at least one of the immune checkpoint inhibitor. In some embodiments, the at least one immune checkpoint inhibitor comprises at least one anti-PD1 antibody, at least one anti-PD-L1 antibody, at least one anti-CTLA4 antibody, or any combination thereof. In some embodiments, the at least one anti-PD1 antibody comprises pidilizumab, BMS-936559, nivolumab, pembrolizumab or any combination thereof. In some embodiments, the at least one anti-PD-L1 antibody comprise atezolizumab, avelumab, durvalumab, MDX-1105, or any combination thereof. In some embodiments, the cancer can be a solid tumor cancer, malignant melanoma, metastatic melanoma, malignant squamous cell carcinoma, metastatic squamous cell carcinoma, glioblastoma, brain cancer, pancreatic cancer, colon cancer, breast cancer, ovarian cancer, prostate cancer, or any combination thereof. In some embodiments, the compound and the at least one additional anti-oncologic agent can be administered at different times. In some embodiments, the compound can be administered 2, 3, 4, or 5 times frequently as the immune checkpoint inhibitor. In some embodiments, the compound can be administered 3 times frequently as the immune checkpoint inhibitor. In some embodiments, the compound can be administered 3 times every 2-3 weeks and the immune checkpoint inhibitor can be administered 1 time the every 2-3 weeks. In some embodiments, the compound can be administered 3 times about every 21 days and the immune checkpoint inhibitor can be administered 1 time the about every 21 days. In some embodiments, the subject can be a human. In some embodiments, the subject can be resistant to an immunotherapy before the treatment. In some embodiments, the administration results in at least one of improved biologic activity, increased stability, prolonged serum bioavailability, prolonged ETBR target engagement, or any combination thereof, compared to a non-deuterated parent compound, as determined by measuring a serum ET-1 level. In some embodiments, the administration restores Tumor Infiltrating Lymphocytes (TILs), intratumoral tertiary lymphoid organ (TLO) formation, or a combination thereof, in a tumor microenvironment.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 10 shows intratumoral TLO formation induced by combination therapy including the immunocheckpoint inhibitor anti-PD1 and the specifically deuterated ETRB antagonist BQ-788-B. Histological examination of V600E+ melanoma tumor cells implanted into C57BL/6 mice 21 days after treatment as indicated in FIG. 8 with BQ-788-B and anti-PD1 combination therapy. The staining of CD8+, CD4+ and Treg (FoxP3) lymphocytes indicates that the combination therapy promotes strong mobilization of lymphocytes to the tumor, which is associated with tumor eradication and positive patient outcomes.

FIG. 11 shows intratumoral (internal) TLO formation associated with treatment with the specifically deuterated compound BQ-788-B. The tables summarize results obtained with combination therapies (two- and three-part), TLO formation and efficacy for tumor eradication. The data indicate that (i) internal TLO formation is associated with tumor reduction; and (ii) the combination immunocheckpoint inhibitors and BQ-788-B was most frequently associated with intratumoral TLO formation and tumor reduction.

DETAILED DESCRIPTION

Figure 1:
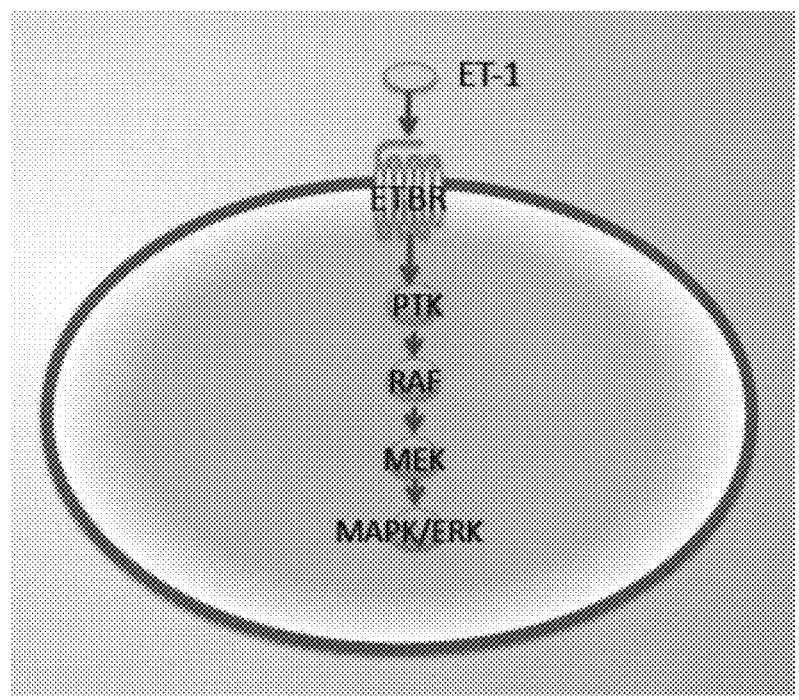
FIG. 1 shows endothelin B receptor (ETBR) cell signal pathway. ETBR is a seven transmembrane G-protein coupled receptor (GPCR). Endothelin-1 (ET-1) is the ligand for the ETBR. Binding of ET-1 to the receptor results in the activation of a number of downstream kinases, including PTK, RAF, MEK, MAPK/ERK.

Disclosed herein are specifically deuterated ETBR antagonist compounds, compositions, and methods useful for the treatment of cancer for example an ETBR-related cancer, e.g., malignant melanoma, metastatic melanoma, squamous cell carcinoma, glioblastoma, ovarian cancer, pancreatic cancer, or any combination thereof. As described herein, specifically deuterated ETBR antagonists as formulated herein are surprisingly advantageous for treating ETBR-related cancers. The use of a specifically deuterated ETBR antagonist significantly improves biologic activity relative to the non-deuterated parent compound, as determined by measuring serum ET-1 levels, and results in at least one of increased stability, prolonged serum bioavailability, prolonged ETBR target engagement, or any combination thereof. In some embodiments, the subject treated is resistant to an immunotherapy. In some embodiments, the composition and method disclosed herein restores Tumor Infiltrating Lymphocytes (TILs) and/or intratumoral tertiary lymphoid organ (TLO) formation in a tumor microenvironment.

Also disclosed herein is a combination that comprises at least one specifically deuterated ETBR antagonist as disclosed herein, and at least one additional anti-oncologic therapeutic agent, administered either at the same time or at different times. In some embodiments, the at least one anti-oncologic agent comprises a bRAF inhibitor, an immune checkpoint inhibitor, a caspase-8 inhibitor, an ETAR antagonist, niacinamide, a chemotherapeutic agent such as, e.g., a taxane, a kinase inhibitor, or other receptor antagonist or combination thereof. In some embodiments, the at least one anti-oncologic agent is an immune checkpoint inhibitor. In some embodiments, the immune checkpoint inhibitor is an anti-PD1 antibody or an anti-PD-L1 antibody. In some embodiments, the anti-PD1 antibody is nivolumab, pembrolizumab, pidilizumab, cemiplimab, or any combination thereof. In some embodiments, the anti-PD-L1 antibody is atezolizumab, MDX-1105, avelumab, durvalumab, or any combination thereof. In some embodiments, specifically deuterated ETRB antagonists as described herein and anti-oncologic agents (i.e. immunocheckpoint inhibitors such as anti-anti-CTLA, anti-PDL1, and anti-PD1 antibodies) can be administered at the same time (e.g. simultaneously. In some embodiments, specifically deuterated ETRB antagonists as described herein and anti-oncologic agents (i.e. immunocheckpoint inhibitors such as anti-CTLA, anti-PDL1, and anti-PD1 antibodies) can be administered at the different times (e.g. simultaneously. In some embodiments, the specifically deuterated ETBR antagonist can be administered once weekly, biweekly, monthly, or bimonthly. In some embodiments, the anti-oncologic agent (i.e. immunocheckpoint inhibitors such as anti-CTLA, anti-PDL1, and anti-PD1 antibodies) can be administered once weekly, biweekly, monthly, or bimonthly. In some embodiments, the specifically deuterated ETBR antagonist is administered 2, 3, 4, or 5 times frequently as the additional anti-oncologic agent, for example that the deuterated ETBR antagonist is administered 3 times during 2-3 weeks (e.g., 21 days) while the additional anti-oncologic agent is administered 1 time during the 2-3 weeks (e.g., the 21 days). In some embodiments, the combination comprises an effective amount of the at least one deuterated ETBR antagonist and an effective amount of the at least one anti-oncologic agent. In some embodiments, the combination includes a pharmaceutically acceptable carrier for example DMSO. In some embodiments, the combination is in separate unit dosage forms, for example, a first container that comprises the at least one specifically deuterated ETBR antagonist, and a second container that comprises the at least one anti-oncologic agent. In some embodiments, the active agents disclosed herein are in a controlled-release delivery system comprises at least one of: (1) a biocompatible polymer, (2) a liposome preparation; (3) a DMSO solution, or a combination thereof.

Definitions

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "combination therapy" refers to both concurrent administration (administration of two or more therapeutic agents at the same time) and time varied administration (administration of one or more therapeutic agents at a time different from that of the administration of an additional therapeutic agent or agents). In some embodiments, the therapeutic agents are present in the patient to some extent, for example at effective amounts, at the same time. In some embodiments, one or more of the compounds described herein, are administered in combination with at least one additional bioactive agent, especially including an anticancer agent. In some embodiments, the combination therapy of compounds results in synergistic activity, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure, are set forth hereinabove.

The term "anti-oncologic agent" is used to describe an anti-cancer agent, which may be combined with compounds according to the present disclosure to treat cancer. These agents include, for example, everolimus, niacinamide, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bc1-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts. In some embodiments, sodium and potassium salts are suitable neutralization salts of the phosphates.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The term "effective" is used to describe an amount of a compound, composition or component which, when used within the context of its intended use, effects an intended result. The term "effective" subsumes all other effective amount or effective concentration terms, which are otherwise described or used in the present application.

The term "therapeutically effective amount" refers to that amount which is sufficient to effect treatment, as defined herein, when administered to a mammal in need of such treatment.

The term "patient" or "subject" is used throughout the specification to describe an animal, for example a human, or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term. Activation of the ETBR by endothelins such as ET-1 and ET-3, results in a variety of molecular events that promote melanoma invasion and metastasis. Without being bound by any particular theory, it is hypothesized that while the majority of melanomas express ETBR, a subset of these also expresses the ETBR activator ET-1 and/or ET-3. It is this subset that is therefore most likely dependent upon ETBR activation for viability, invasive potential and metastatic potential. Thus, this subset of patients is most likely to respond to ETBR blockade. Furthermore, this subset of patients is least likely to response to immune based therapy.

The Endothelin B receptor (ETBR) pathway (FIG. 1) plays a significant role in the metastatic spread of melanoma, and therefore, is a target for therapeutic intervention. The Endothelin B receptor is a 7 transmembrane G-protein coupled receptor (GPCR). It is expressed at very low levels in normal melanocytes, but is upregulated during melanoma development and progression. RAF and MEK kinases, current melanoma drug targets, are activated by the deuterated ETBR. The specific deuterated are beneficial because, as compared to nondeuterated, there is an improvement in one or more pharmaceutical properties (e.g. efficacy, solubility)

Figure 2:
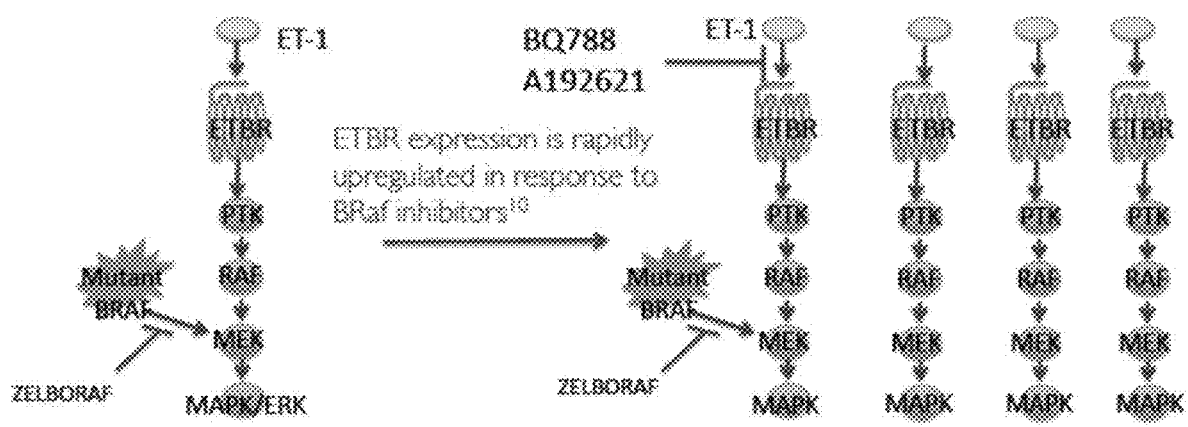
FIG. 2 shows drug resistance to bRAF inhibitors is due to ETBR upregulation. Upregulation of ETBR allows melanoma cells to bypass the block to MAPK/ERK activation. ETBR antagonists, including specifically deuterated ETBR antagonists as described herein, block ET-1 binding.
Figure 3:
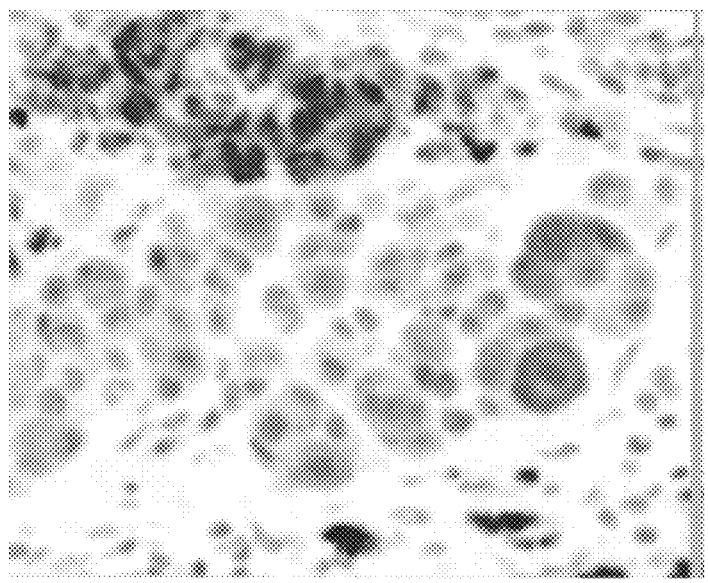
FIG. 3 shows that ET-1 is expressed by advanced melanomas. ET-1 is the ligand that activates the ETBR, which causes melanoma cells to proliferate, metastasize, and generate their own blood supply. The tissue section is from a human invasive melanoma specimen stained with an ET-1 specific label. The photograph indicates that the melanoma is positive for ET-1. Invasive and metastatic melanomas produce ET-1.

Endothelin-1 (ET-1) (and Endothelin-3, not shown) is a ligand that activates the ETBR (FIG. 2). ET-1 activation of ETBR causes melanoma cells to proliferate, metastasize and generate their own blood supply. Our studies show that the majority of pigmented invasive melanomas and metastatic melanomas produce ET-1 (FIG. 3).

Deuterated Compounds (Specific)

Disclosed herein is a specifically deuterated ETBR antagonist, e.g., a deuterated form of BQ-788 as described herein. In some embodiments, the description provides a composition comprising at least one specifically deuterated ETBR antagonist, e.g., a deuterated form of BQ-788 as described herein, and a pharmaceutically acceptable carrier. In some embodiments, the description provides a composition, e.g., a pharmaceutical composition, comprising an effective amount of at least one specifically deuterated ETBR antagonist, e.g., a deuterated form of BQ-788 as described herein, and a pharmaceutically acceptable carrier. In some embodiments, the pharmaceutical composition as described herein can be in unit dosage form configured for administration one or more times, for example, one or more times per day, per week, or per month.

In some embodiments, the specifically deuterated ETBR antagonist is a compound of the Formula (1) below:

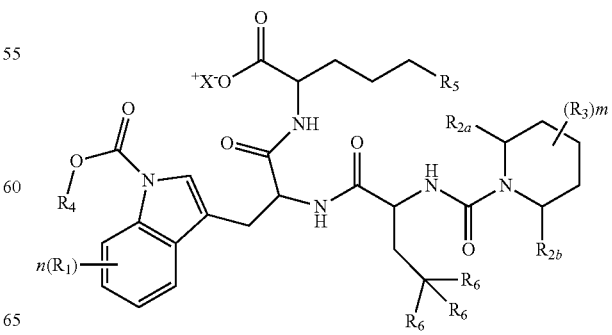

Formula (1)

wherein n is an integer from 0-5;

m is an integer from 0-3;

X is a positively charged counterion;

$R_1$ and $R_3$ are independently —H, -D, —$CH_3$, —$CH_2D$, —$CHD_2$, or —$CD_3$; $R_{2a}$, $R_{2b}$, $R_4$, $R_5$, and $R_6$ are independently —$CH_3$, —$CH_2D$, —$CHD_2$, or —$CD_3$; and at least one of $R_1$, $R_2$, or $R_3$ comprises deuterium.

In some embodiments, the specifically deuterated ETBR antagonist of formula (1) comprises 1-8 deuterium atoms. In specific embodiments, the specifically deuterated ETBR antagonist of formula (1) comprises 1, 2, or 3 deuterium atoms.

In some embodiments, the specifically deuterated ETBR antagonist is a compound of the Formula (2) below:

In some embodiments, the specifically deuterated ETBR antagonist is a compound of the Formula (3) below:

In some embodiments, the specifically deuterated ETBR antagonist is a compound of the Formula (4) below:

In some embodiments, the specifically deuterated ETBR antagonist is a compound of the Formula (5) below:

In some embodiments, the specifically deuterated ETBR antagonist is a compound of the formula (6) below:

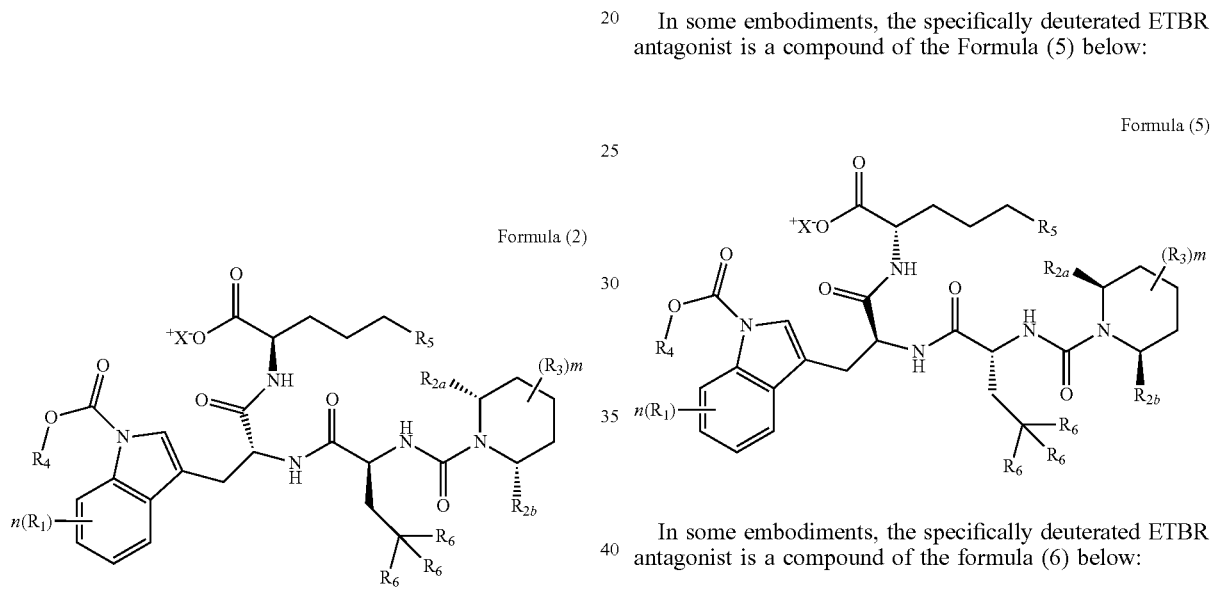

In some embodiments, the specifically deuterated ETBR antagonist of formula (6), n is 0 or 1.

In some embodiments of the specifically deuterated ETBR antagonist of formula (6), n is 1 and R1 is -D.

In some embodiments of the specifically deuterated ETBR antagonist of formula (6), n is 1, $R_1$ is -D; and $R_{2a}$ and $R_{2b}$ are —$CH_3$.

In some embodiments of the specifically deuterated ETBR antagonist of formula (6), n is 0, $R_1$ is —H; $R_{2a}$ is —$CH_3$ and $R_{2b}$ is —$CH_2D$.

In some embodiments of the specifically deuterated ETBR antagonist of formula (6), n is 0, $R_1$ is —H; $R_{2a}$ is —CH$_2$D and $R_{2b}$ is —CH$_3$.

In some embodiments of the specifically deuterated ETBR antagonist of formula (6), n is 0, $R_1$ is —H; and $R_{2a}$ and $R_{2b}$ are —CH$_2$D.

In some embodiments of the specifically deuterated ETBR antagonist of formula (6), n is 1, $R_1$ is -D; and $R_{2a}$ and $R_{2b}$ are —CH$_2$D.

In some embodiments, the specifically deuterated ETBR antagonist is at least one of BQ-788-A, BQ-788-B, BQ-788-C, or a combination thereof, including analogs, derivatives, polymorphs, prodrugs, and salts thereof, including fluorinated analogues. For example, the specifically deuterated ETBR antagonist can be a fluorinated analog of BQ-788-A, BQ-788-B, or BQ-788-C.

In some embodiments, BQ-788-A is a specifically deuterated ETBR antagonist depicted below.

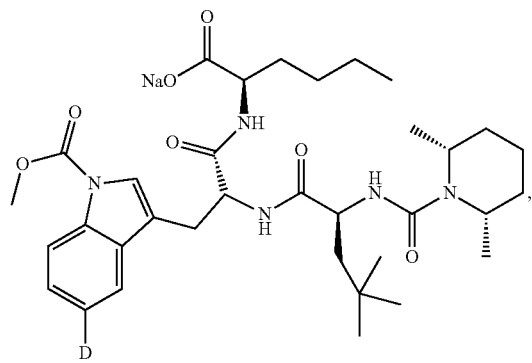

a stereoisomer thereof, or a pharmaceutically acceptable salt thereof.

In some embodiments, BQ-788-B is a specifically deuterated ETBR antagonist depicted below:

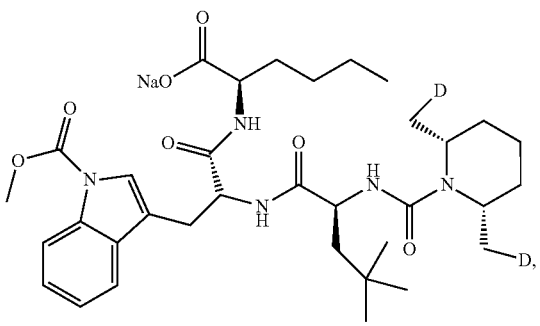

a stereoisomer thereof, or a pharmaceutically acceptable salt thereof.

In some embodiments, BQ-788-C is a specifically deuterated ETBR antagonist depicted below:

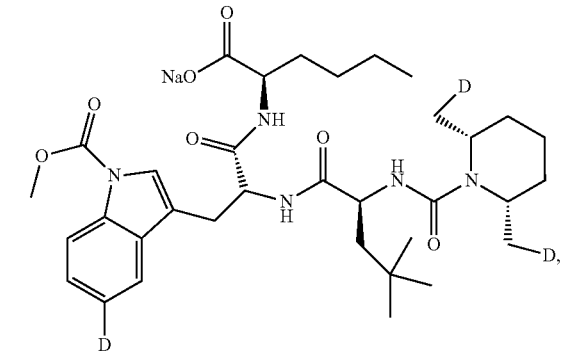

a stereoisomer thereof, or a pharmaceutically acceptable salt thereof.

In some embodiments, a compound disclosed here is of Formula (7):

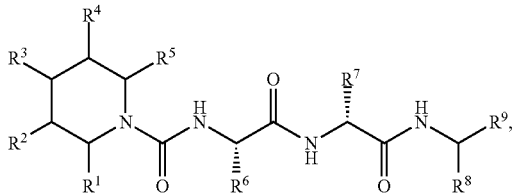

Formula (7)

a stereoisomer thereof, or a Pharmaceutically acceptable salt thereof,
wherein:
each of $R^1$, $R^2$, $R^3$, $R^4$, or $R^5$ is independently hydrogen, halogen, hydroxyl, deuterium, halogen, hydroxy, amino, nitro, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ haloalkykl, optionally substituted aryl, or optionally substituted heteroaryl, optionally wherein one or more of the carbons in the piperidinyl ring can be a heteroatom selected from O, N, or S, or wherein the piperidinyl ring may contain one or more double bonds;
$R^6$ is optionally substituted $C_1$-$C_8$ alkyl, optionally substituted $C_2$-$C_8$ alkenyl, optionally substituted $C_2$-$C_8$ alkynyl, optionally substituted $C_3$-$C_8$-cycloalkyl, optionally substituted $C_1$-$C_8$ alkoxy, optionally substituted $C_1$-$C_8$ haloalkykl, optionally substituted aryl, or optionally substituted heteroaryl, wherein $R^6$ optionally comprises deuterium;
$R^7$ is optionally substituted cycloalkyl, optionally substituted heterocycloalkyl, optionally substituted aryl, optionally substituted heteroaryl, optionally substituted polycyclic ring system, optionally substituted bicyclic, optionally substituted heterobicyclic, wherein $R^7$ optionally comprises deuterium; $R^8$ and $R^9$ are independently optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted C₁-C₈ haloalkyl, optionally substituted aryl, optionally substituted heteroaryl, or —COOR', or R⁸ and R⁹ may be taken together to form a optionally substituted cycloalkyl, optionally substituted cycloalkyl heterocycloalkyl, optionally substituted aryl, optionally substituted heteroaryl, or optionally substituted polycyclic ring system, wherein R⁸ or R⁹ each optionally comprises deuterium;

R' is hydrogen, hydroxy, or C₁-C₈ alkyl; and wherein at least one of R¹, R², R³, R⁴, R⁵, R⁶, R⁷, R⁸, or R⁹ is deuterium.

In some embodiments, a compound disclosed here is of Formula (8):

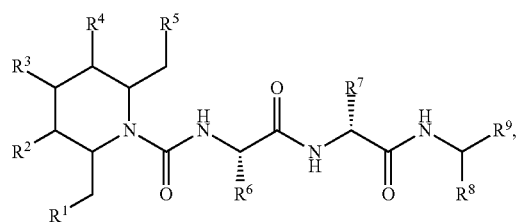

Formula (8)

a stereoisomer thereof, or a pharmaceutically acceptable salt thereof, wherein:

each of R², R³, or R⁴ is independently hydrogen, deuterium, halogen, hydroxy, amino, nitro, C₁-C₈ alkyl, C₂-C₈ alkenyl, C₂-C₈ alkynyl, C₃-C₈ cycloalkyl, C₁-C₈ alkoxy, C₁-C₈ haloalkykl, aryl, or heteroaryl;

R⁶ is C₁-C₈ alkyl, C₂-C₈ alkenyl, C₂-C₈ alkynyl, C₃-C₈ cycloalkyl, C₁-C₈ alkoxy, C₁-C₈ haloalkykl, aryl, or heteroaryl, wherein R⁶ optionally comprises deuterium;

R⁷ is substituted or unsubstituted cycloalkyl, substituted or unsubstituted heterocycloalkyl, substituted or unsubstituted aryl, substituted or unsubstituted heteroaryl, or a substituted or unsubstituted polycyclic ring system, wherein R⁷ optionally comprises deuterium;

R⁸ and R⁹ are independently C₁-C₈ alkyl, C₂-C₈ alkenyl, C₂-C₈ alkynyl, C₃-C₈-cycloalkyl, C₁-C₈ alkoxy, C₁-C₈ haloalkykl, aryl, heteroaryl, or —COOR', or R⁸ and R⁹ may be taken together to form a substituted or unsubstituted cycloalkyl, substituted or unsubstituted cycloalkyl heterocycloalkyl, substituted or unsubstituted aryl, substituted or unsubstituted heteroaryl, or substituted or unsubstituted polycyclic ring system, wherein R⁸ or R⁹ each optionally comprises deuterium;

R' is hydrogen, hydroxy, or C₁-C₈ alkyl; and wherein at least one of R¹, R², R³, R⁴, R⁵, R⁶, R⁷, R⁸, or R⁹ is deuterium.

In some embodiments, a compound disclosed here is Formula (9):

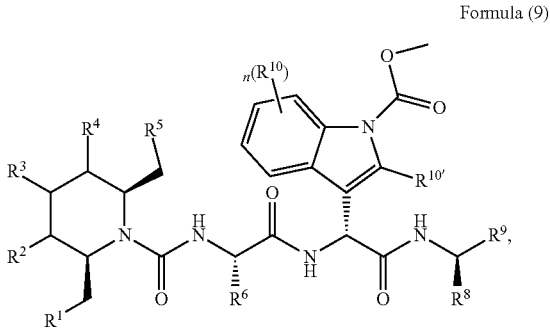

Formula (9)

a stereoisomer thereof, or a pharmaceutically acceptable salt thereof, wherein:

each of R¹ R₂, R³, R⁴, or R⁵ is independently hydrogen, deuterium, halogen, hydroxy, amino, nitro, C₁-C₈ alkyl, C₂-C₈ alkenyl, C₂-C₈ alkynyl, C₃-C₈ cycloalkyl, C₁-C₈ alkoxy, C₁-C₈ haloalkyl, aryl, or heteroaryl;

R⁶ is C₁-C₈ alkyl, C₂-C₈ alkenyl, C₂-C₈ alkynyl, C₃-C₈-cycloalkyl, C₁-C₈ alkoxy, C₁-C₈ haloalkykl, aryl, or heteroaryl, wherein R⁶ optionally comprises deuterium;

R⁸ and R⁹ are independently C₁-C₈ alkyl, C₂-C₈ alkenyl, C₂-C₈ alkynyl, C₃-C₈ cycloalkyl, R⁸ and R⁹ are independently C₁-C₈ alkyl, C₂-C₈ alkenyl, C₂-C₈ alkynyl, C₃-C₈-cycloalkyl, C₁-C₈ alkoxy, C₁-C₈ haloalkykl, aryl, heteroaryl, or —COOR', or R⁸ and R⁹ may be taken together to form a substituted or unsubstituted cycloalkyl, substituted or unsubstituted cycloalkyl heterocycloalkyl, substituted or unsubstituted aryl, substituted or unsubstituted heteroaryl, or substituted or unsubstituted polycyclic ring system, wherein R⁸ or R⁹ each optionally comprises deuterium;

R¹⁰ and R¹⁰' are independently hydrogen, deuterium, halogen, hydroxy, amino, nitro, C₁-C₈ alkyl, C₂-C₈ alkenyl, C₂-C₈ alkynyl, C₃-C₈-cycloalkyl, C₁-C₈ alkoxy, C₁-C₈ haloalkykl, aryl, or heteroaryl;

n is an integer from 0-4; and wherein at least one of R¹, R², R³, R⁴, R⁵, R⁶, R⁷, R⁸, R⁹, R¹⁰ or R¹⁰' is deuterium.

Pharmaceutical Compositions

Provided herein are pharmaceutical compositions comprising at least one specifically deuterated ETBR antagonist, e.g., a deuterated form of BQ-788 as described herein, and a pharmaceutically acceptable carrier.

In some embodiments, the compositions herein are formulated in a unit dosage form, including any desired carrier or excipient, and configured for administration via any desired route, e.g., oral, intravenous, subcutaneous, intramuscular, intraperitoneal, parenteral, intranasal, intracranial.

In some embodiments, the compositions as described herein are useful for the treatment of ETBR-related cancer in a patient. In some embodiments, the cancer is a solid tumor. In some embodiments, the cancer is at least one of breast cancer, melanoma, SCC, glioblastoma, ovarian cancer, pancreatic cancer, or a combination thereof.

In some embodiments, the compositions comprise a dosage of the specifically deuterated ETBR antagonist of about 0.1 mg to about 500 mg (e.g., about 10 mg to about 100 mg), and/or a concentration of the specifically deuterated ETBR antagonist of about 0.01 g/mL to about 1000 mg/mL (e.g., about 0.1 mg/mL to about 5 mg/mL).

In some embodiments, the compositions as described herein are formulated in a conventional manner using one or more pharmaceutically acceptable carriers and may also be administered in controlled-release formulations. Pharmaceutically acceptable carriers that may be used in these pharmaceutical compositions include, but are not limited to, dimethyl sulfoxide (DMSO), soybean oil as a carrier, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the compositions include at least one of soybean oil, dimethyl sulfoxide (DMSO), hydrogel, or a combination thereof. Any of the embodiments described herein can be a single-component oil phase formulation, as described above, wherein each active ingredient can be at any of the dosages or concentrations described herein. The single-component oil phase can be a fixed oil, such as soybean oil. For example, the formulation comprises about 0.1 mg to about 5.0 mg of each active ingredient in 1 mL of the single-component oil (i.e., about 0.5 mg/mL, about 1 mg/mL, or about 1.5 mg/mL of each active ingredient in the single-component oil). The single-component oil phase formulation can be prepared by adding each active ingredient (e.g., about 1 mg to about 50 mg of each of the active ingredient(s)) to about 10 mL of the single-component oil solution.

In some embodiments, pharmaceutical compositions herein comprise a DMSO, e.g., in a DMSO solution that is about 5% to about 100% DMSO (e.g., about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 30% to about 95%, about 45% to about 95%, about 75% to about 95%, about 30% to about 90%, about 45% to about 90%, about 75% to about 90%, about 30% to about 85%, about 45% to about 85%, or about 75% to about 85%). For example, the pharmaceutical compositions comprises about 0.1 mg to about 5.0 mg of each active ingredient in 1 mL of DMSO (i.e., about 0.5 mg/mL, about 1 mg/mL, or about 1.5 mg/mL of each active ingredient in DMSO). The DMSO pharmaceutical compositions can be prepared by adding each active ingredient (e.g., about 1 mg to about 50 mg of each of the active ingredient(s)) to about 10 mL of the DMSO solution. For example, the DMSO is a DMSO solution comprising about 5% to about 100% DMSO, about 25% to about 100% DMSO, about 50% to about 100% DMSO, about 75% to about 100% DMSO, about 5% to about 75% DMSO, about 25% to about 75% DMSO, about 50% to about 75% DMSO, about 5% to about 50% DMSO, about 25% to about 50% DMSO, or about 5% to about 25% DMSO.

In some embodiments, the description provides a controlled release subcutaneous or intramuscular dosage formulation comprising a uniform dispersion of a specifically deuterated ETBR antagonist (e.g., BQ-788, BQ-017, A192621, a deuterated or fluorinated analog thereof, or combinations thereof) and an ETAR antagonist (e.g., BQ123) in a biocompatible delivery system whereby following administration the deuterated ETBR and ETAR antagonists are released slowly and simultaneously from the formulation into the systemic circulation.

In some embodiments, the pharmaceutical composition as described herein is formulated into a controlled release delivery system comprising at least one biocompatible polymer. In some embodiments, the active compounds are prepared with carriers that will protect the compound against rapid elimination from the body, such as a controlled release formulation, including implants, hydrogels, thermo-sensitive hydrogels, and microencapsulated delivery systems. Biodegradable, biocompatible polymers can be used, such as ethylene vinyl acetate, acrylates, polycarboxylic acids, polyanhydrides, polyglycolic acid, collagen, polyorthoesters, and polylactic acid. In some embodiments, the biocompatible polymer is at least one of a poly(lactide), poly(glycolide), poly(lactide-co-glycolide), poly(lactic acid), poly(glycolic acid), poly(lactic acid-co-glycolic acid), polycaprolactone, polycarbonate, polyesteramide, polyanhydride, poly(amino acid), polyorthoester, polycyanoacrylate, poly(p-dioxanone), poly(alkylene oxalate), biodegradable polyurethane, blend, or a copolymer thereof.

In some embodiments, the pharmaceutically acceptable carrier comprises or is a liposome. For example, the pharmaceutical composition or formulation may comprise a liposome having an interior volume comprising a specifically deuterated ETBR antagonist. In some embodiments, the liposome is configured to effectuate the controlled release of the specifically deuterated ETBR antagonist, e.g., rapid release, extended release, or a combination thereof.

In some embodiments, the liposome is configured to effectuate the controlled release of the pharmaceutical compositions. In some embodiments, the liposome is configured to effectuate rapid release of the pharmaceutical compositions. In other embodiments, the liposome is configured or formulated to effectuate extended release the pharmaceutical compositions. In some embodiments, the liposome is configured to result in both the rapid and extended release of pharmaceutical compositions.

In some embodiments, the liposome is configured to effectuate the controlled release of the specifically deuterated ETBR antagonist or the caspase-8 inhibitor or a combination thereof. In some embodiments, the liposome is configured to effectuate rapid release of the specifically deuterated ETBR antagonist or the caspase-8 inhibitor or a combination thereof. In other embodiments, the liposome is configured or formulated to effectuate extended release the specifically deuterated ETBR antagonist or the caspase-8 inhibitor or a combination thereof. In some embodiments, the liposome is configured to result in both the rapid and extended release of the specifically deuterated ETBR antagonist or the caspase-8 inhibitor or a combination thereof.

In some embodiments, liposomal suspensions are pharmaceutically acceptable carriers. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

In some embodiments, the pharmaceutical compositions comprise a liposome having an interior volume comprising a specifically deuterated ETBR antagonist or a caspase-8 inhibitor or a combination thereof, and an effective amount of at least one of an ETAR antagonist, an anti-PD1 antibody, a bRAF inhibitor, niacinamide or a combination thereof. In some embodiments, the liposome comprises at least one of a neutral lipid, a basic (having a net positive charge) lipid, an acidic (having a net negative charge) lipid, cholesterol, or a combination thereof. In some embodiments, the liposome further comprises a polymeric component. In some embodiments, the interior volume of the liposome is at least partially aqueous, and comprises a specifically deuterated ETBR antagonist.

In some embodiments, the description provides the pharmaceutical composition as described herein in a liposomal delivery system, e.g., at least one of a phosphatidylethanolamine (PE) such as dipalmitoyl PE (DPPE), and partially unsaturated phosphatidylcholine (PC), such as egg PC (EPC) or SPC, fully unsaturated PC such as HSPC, PG, phosphatidylserine (PS), phosphatidylinositol (PI) or a combination thereof. In some embodiments, the phospholipid is at least one of a partially unsaturated PG, dipalmitoylphosphatidylglycerol (DPPG), cholesterol, DSPE-PEG2000, polysorbate-80 or combination thereof. In some embodiments, the liposomal delivery system is a controlled release system, e.g., at least one of rapid release, extended release, rapid and extended release, delayed release, sustained release, slow release, and combinations thereof.

In some embodiments, the pharmaceutical compositions herein comprise pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, bitartrate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others. Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form nontoxic base salts with such compounds. Such nontoxic base salts include, but are not limited to those derived from such pharmacologically acceptable cations such as alkali metal cations (eg., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

In some embodiments, oral compositions include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

In some embodiments, the active compound or pharmaceutically acceptable salt thereof is administered as a component of an elixir, suspension, syrup, wafer, chewing gum or the like. A syrup may contain, in addition to the active compounds, sucrose as a sweetening agent and certain preservatives, dyes and colorings and flavors.

In some embodiments, solutions or suspensions used for parenteral, intradermal, subcutaneous, intravenous, intramuscular, or topical application include the following components: a sterile diluent such as water for injection, saline solution, fixed oils (e.g., soybean oil), polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. In some embodiments, carriers for intravenous administration are physiological saline or phosphate buffered saline (PBS).

Combination Therapy

Disclosed herein are pharmaceutical compositions for therapeutic combinations, in a single dosage form or separate dosage forms administered concurrently or separately, comprising at least one of specifically deuterated ETBR antagonist as described herein, and at least one additional anti-oncologic agent. In some embodiments, the at least one additional anti-oncologic agent is an immune checkpoint inhibitor, e.g., an anti-PD1 antibody or anti-PD-L1 antibody. In some embodiments, the specifically deuterated ETBR antagonist is administered 2, 3, 4, or 5 times frequently as the additional anti-oncologic agent, for example that the specifically deuterated ETBR antagonist is administered 3 times during 1-3 weeks (e.g., about 2-3 weeks or about 21 days) while the additional anti-oncologic agent is administered 1 time during the 1-3 weeks (e.g., about 2-3 weeks or about 21 days).

In some embodiments, the pharmaceutical compositions as described herein demonstrate a synergistic effect in that the pharmaceutical compositions achieve at least one of: a greater therapeutic effect (i.e., more efficacious) than the additive therapeutic effect obtained by administration of the constituent ingredients alone, a greater therapeutic effect than achieved by administration of a higher dose of the constituent ingredients alone, a similar or greater therapeutic effect but with a decrease in adverse events or side effects relative to that observed by administration of the constituent ingredients alone (i.e., improved therapeutic window), or increased duration of effects, or a similar or greater therapeutic effect at a smaller dose of one or both of the constituent ingredients or a combination thereof.

In some embodiments, the description provides pharmaceutical compositions comprising a first composition comprising a specifically deuterated ETBR antagonist as described herein in an amount effective when administered with at least one additional anticancer or anti-oncologic agent; and a second composition comprising an effective amount of the at least one additional anticancer or anti-oncologic agent as described herein.

In some embodiments, the description provides a combination comprising at least one ETBR antagonist, e.g., a specifically deuterated ETBR antagonist, and at least one additional anti-oncologic therapeutic agent. In some embodiments, the at least one anti-oncologic agent is a bRaf inhibitor, an immune checkpoint inhibitor, a caspase-8 inhibitor, an ETAR antagonist, niacinamide, a chemotherapeutic agent such as, e.g., a taxane, a kinase inhibitor, or other receptor antagonist or combination thereof. In some embodiments, the pharmaceutical compositions comprise an effective amount (e.g., a synergistically effective amount) of at least two of specifically deuterated ETBR antagonist, bRaf inhibitor, an immune checkpoint inhibitor, a caspase-8 inhibitor, an ETAR antagonist, niacinamide, a chemotherapeutic agent such as, e.g., a taxane, a kinase inhibitor, or other receptor antagonist or combination thereof.

In some embodiments, the specifically deuterated ETBR antagonist and the at least one additional anti-oncologic therapeutic agent are comprised in separate pharmaceutical compositions. In some embodiments, the specifically deuterated ETBR antagonist and the at least one additional anti-oncologic therapeutic agent are comprised in the same pharmaceutical composition.

In some embodiments, the description provides methods comprising administering a specifically deuterated ETBR antagonist as described herein in an amount effective for treating cancer and an anti-oncologic agent, and a pharmaceutically acceptable excipient or carrier. In some embodiments, the specifically deuterated ETBR antagonist is at least one of a deuterated BQ-788, BQ-017, A192621, BQ-788-A, BQ-788-B, or BQ-788-C or a combination thereof.

In some embodiments, the description provides a pharmaceutical composition comprising a specifically deuterated ETBR antagonist as described herein in an amount effective for treating cancer, and a pharmaceutically acceptable carrier. In some embodiments, the amount is effective to treat cancer when also administered with at least one additional anti-oncologic agent, and a pharmaceutically acceptable excipient or carrier. In some embodiments, the specifically deuterated ETBR antagonist is at least one of a deuterated BQ-788, BQ-017, A192621, BQ-788-A, BQ-788-B, or BQ-788-C or a combination thereof.

In some embodiments, the description provides a therapeutic combination comprising, in the same or separate dosage forms, an effective amount of the at least one ETBR antagonist and an effective amount of at least one anti-oncologic agent. In some embodiments, the combination comprises a synergistically effective amount of the at least one ETBR antagonist. In some embodiments, the combination comprises a synergistically effective amount of the at least one anti-oncologic agent. In some embodiments, the combination includes a pharmaceutical acceptable carrier. In some embodiments, the combination or formulation is comprised in one or more unit dosage forms. In further embodiments, the combination is comprised in separate unit dosage forms, for example, a first container comprising the at least one ETBR antagonist, and a second container comprising the at least one anti-oncologic agent. In some embodiments, the ETBR antagonist is a specifically deuterated ETBR antagonist as described herein.

In some embodiments, the description provides a combination therapy comprising administering: (a) a first composition comprising an effective amount of a specifically deuterated ETBR antagonist and a pharmaceutically acceptable carrier or excipient; and (b) a second composition comprising an effective amount of at least one additional anti-oncologic agent, and a pharmaceutically acceptable carrier or excipient, wherein the administering demonstrates synergistic anti-cancer activity. In some embodiments, the specifically deuterated ETBR antagonist is a deuterated BQ-788 as described herein.

In some embodiments, the at least one anti-oncologic agent is an immune checkpoint inhibitor. In some embodiments, the immune checkpoint inhibitor is an anti-PD1 antibody or an anti-PD-L1 antibody. In some embodiments, the anti-PD1 antibody is at least one of nivolumab, pembrolizumab, pidilizumab, or any combination thereof. In some embodiments, the anti-PD-L1 antibody is atezolizumab, MDX-1105, avelumab, durvalumab, or any combination thereof.

In some embodiments, the bRAF inhibitor is at least one of dabrafenib, sorafenib, vemurafenib, or any other bRAF inhibitor known or that becomes known to one skilled in the art.

In some embodiments, caspase-8 is a downstream effector of the ETBR, and caspase-8 inhibitors block molecular events that promote invasion and metastasis that are triggered as a result of ETBR activation. As such, caspase-8 inhibitors can be classified as a caspase-8 antagonist or an antagonist/inhibitor of ETBR signaling. In some embodiments, the caspase-8 inhibitor peptide has a sequence of Ac-AAVALLPAVLLAALAPIETD-CHO, which is commercially available from EMD Millipore (Billerica, MA 01821, USA).

In some embodiments, the physiologic role of the ETBR is to clear excess levels of endothelin-1 (ET-1), from the circulation. Without being bound by any particular theory, it is hypothesized that administering a specifically deuterated ETBR antagonist prevents ET-1 clearance and elevates serum ET-1 levels. Elevated serum levels of ET-1 are associated with a variety of adverse effects due to its activation of the Endothelin A receptor (ETAR) including, hypertension, pulmonary hypertension and renal vasoconstriction. In some embodiments, in order to minimize the unwanted effect of ETAR activation, the description provides pharmaceutical compositions and methods for combination therapy (in a single dosage form or separate dosage forms administered approximately contemporaneously) of a specifically deuterated ETBR antagonist with an ETAR antagonist. The ETAR antagonist acts synergistically to enhance the beneficial effects of a specifically deuterated ETBR antagonist while minimizing adverse events or side effects. It was also surprising that an effective amount (e.g., a synergistically effective amount) of niacinamide was effective at synergistically minimizing adverse events or side effects, such as weight loss, from the specifically deuterated ETBR antagonist. The formulations as described herein are useful for the treatment of cancer in a patient, for example, breast cancer, melanoma, SCC, glioblastoma; solid tumors or a combination thereof.

In some embodiments, the ETAR antagonist is BQ123. BQ123 (2-[(3R,6R,9S,12R,15S)-6-(1H-indol-3-ylmethyl)-9-(2-methylpropyl)-2,5,8,11,14-pentaoxo-12-propan-2-yl-1,4,7,10,13-pentazabicyclo[13.3.0]octadecan-3-yl]acetic acid or cyclo(D-Trp-D-Asp-Pro-D-Val-Leu)) is a selective ETAR antagonist. (Ishikawa et al., (1992). "Cyclic pentapeptide endothelin antagonists with high ETA selectivity. Potencyand solubility-enhancing modifications." Journal of Medicinal Chemistry 35 (11): 1239-42, which is incorporated herein by reference). BQ123 is available commercially from, e.g., ABI Chem (AC1L9EDH).

In some embodiments, pharmaceutical compositions herein comprise an effective amount of a specifically deuterated ETBR antagonist in combination with an effective amount of an ETAR antagonist, and a pharmaceutically acceptable carrier. In some embodiments, the effective amount of an ETAR is a synergistically effective amount. In some embodiments, the specifically deuterated ETBR antagonist is at least one of a deuterated form of BQ-788, A192621, or a combination thereof, including analogs, derivatives, polymorphs, prodrugs, and salts thereof. In some embodiments, the ETAR antagonist is BQ123, including analogs, derivatives, polymorphs, prodrugs, and salts thereof.

In some embodiments, the additional anti-oncologic agent is at least one of apx005m, ipilimumab, vemurafenib, dacabazine, nivolumab, pembrolizumab, niacinamide, interleukin-2, DEDN6526, Talimogene laherparepvec, tumor infiltrating lymphocytes, an anti-angiogenic agent, adriamycin, camptothecin, carboplatin, cisplatin, daunorubicin, doxorubicin, alpha, beta, or gamma interferon, irinotecan, docetaxel, paclitaxel, topotecan, atrasentan, tezosentan, bosentan, sitaxsentan, enrasentan, zibotentan, Ro468443, TBC10950, TBC10894, A192621, A308165, SB209670, SB17242, A182086, (s)-Lu302872, J-104132, TAK-044, Sarafotoxin 56c, IRL2500, RES7011, Aselacins A, B, and C, Ro470203, Ro462005, sulfamethoxazole, cochinmicin I, II, and III, L749329, L571281, L754142, J104132, CGS27830, PD142893, PD143296, PD145065, PD156252, PD159020, PD160672, PD160874, TM-ET-1, IRL3630, Ro485695, L75037, LU224332, PD142893, LU302872, PD145065, Ro610612, SB217242, or a combinations thereof. In some embodiments, the additional anti-oncologic agent is a RAF kinase antagonist, a MEK antagonist or a combination thereof. In some embodiments, the anti-oncologic agent is at least one of an IDO inhibitor, HDAC inhibitor, DNMT inhibitor, adenosine receptor inhibitor, CXCR4/CXCL12 axis inhibitor or a combination thereof. In some embodiments, the DNMT inhibitor is vidaza. In some embodiments, the HDAC inhibitor is at least one of entinostat, mocetinostat, inostat, romidepsin, ACY-241, farydak or a combination thereof. In some embodiments, the adenosine receptor inhibitor is at least one of CPI-444 (V81444), PBF-509, MEDI9447, MK-3814, AZD4635, BMS-986179 or a combination thereof. In some embodiments, the CXCR4/CXCL12 axis inhibitor is at least one of ulocuplumab, BL-8040, PF-06747143, POL6326, plerixafor, ALX-0651, LY2510924, AMD11070, X4P-001, Q122, USL311, burixafor hyrobromid, CX-01, CTCE 9908, GMI-1359 or a combination thereof. In some embodiments, the anti-oncologic agent is an anti-angiogenic agent selected from thalidomide, marimastat, COL-3, BMS275291, squalamine, 2-ME, SU6668, neovastat, Medi522, EMD121974, CAI, celecoxib, interleukin-12, IM862, TNP470, avastin, gleevac, herceptin, or a combination thereof. In some embodiments, the anti-oncologic agent is a cell CDK4/6 cycle inhibitor, for example, ribociclib, palbociclib, milciclib, voruciclib, abemaciclib, flavopiridol or a combination thereof.

In some embodiments, a dosage of the specifically deuterated ETBR antagonist is about 0.1 µg to about 500 mg (e.g., about 100 µg to about 4000 µg) and/or a concentration of the specifically deuterated ETBR antagonist is about 0.01 µg/mL to about 1000 mg/mL of the composition (e.g., about 0.1 mg/mL to about 5 mg/mL).

In some embodiments, a dosage of the ETAR antagonist is about 0.1 µg to about 500 mg (e.g., about 100 µg to about 4000 µg) and/or a concentration of the ETAR antagonist is about 0.01 µg/mL to about 1000 mg/mL of the composition (e.g., about 0.1 mg/mL to about 5 mg/mL).

In some embodiments, a dosage of the anti-PD1 antibody is about 0.1 µg to about 500 mg (e.g., about 100 µg to about 4000 µg) and/or a concentration of the anti-PD1 antibody is about 0.01p g/mL to about 1000 mg/mL of the composition (e.g., about 0.1 mg/mL to about 5 mg/mL).

In some embodiments, a dosage of the bRAF inhibitor is about 0.1 µg to about 500 mg (e.g., about 100 µg to about 4000 µg) and/or a concentration of the bRAF inhibitor is about 0.01 µg/mL to about 1000 mg/mL of the composition (e.g., about 0.1 mg/mL to about 5 mg/mL).

In some embodiments, a dosage of the niacinamide is about 0.1 µg to about 500 mg (e.g., about 100 µg to about 4000 µg) and/or a concentration of the niacinamide is about 0.01 µg/mL to about 1000 mg/mL of the composition (e.g., about 0.1 mg/mL to about 5 mg/mL).

In some embodiments, a dosage of the caspase-8 inhibitor is about 0.1 µg to about 500 mg (e.g., about 100 µg to about 4000 µg or about 1 µg to about 4000 µg) and/or a concentration of the caspase-8 inhibitor is about 0.01 µg/mL to about 1000 mg/mL of the composition (e.g., about 0.1 mg/mL to about 5 mg/mL).

In some embodiments, the concentration of the at least one specifically deuterated ETBR antagonist, and/or the at least one anti-oncologic agent can independently be about 0.01 µg/mL to about 1000 mg/mL, about 0.01 µg/mL to about 750 mg/mL, about 0.01 µg/mL to about 500 mg/mL, about 0.01 µg/mL to about 300 mg/mL, about 0.01 µg/mL to about 150 mg/mL, about 0.01 µg/mL to about 100 mg/mL, about 0.01 µg/mL to about 50 mg/mL, about 0.01 µg/mL to about 25 mg/mL, about 0.01 µg/mL to about 10 mg/mL, about 0.01 µg/mL to about 1.0 mg/mL, about 0.01 µg/mL to about 0.1 µg/mL, about 0.1 µg/mL to about 750 mg/mL, about 0.1 µg/mL to about 500 mg/mL, about 0.1 µg/mL to about 300 mg/mL, about 0.1 µg/mL to about 150 mg/mL, about 0.1 µg/mL to about 100 mg/mL, about 0.1 µg/mL to about 50 mg/mL, about 0.1 µg/mL to about 25 mg/mL, about 0.1 µg/mL to about 10 mg/mL, about 0.1 µg/mL to about 1.0 mg/mL, about 1.0 µg/mL to about 750 mg/mL, about 1.0 µg/mL to about 500 mg/mL, about 1.0 µg/mL to about 300 mg/mL, about 1.0 µg/mL to about 150 mg/mL, about 1.0 µg/mL to about 100 mg/mL, about 1.0 µg/mL to about 50 mg/mL, about 1.0 µg/mL to about 25 mg/mL, about 1.0 µg/mL to about 10 mg/mL, about 10 µg/mL to about 750 mg/mL, about 10 µg/mL to about 500 mg/mL, about 10 µg/mL to about 300 mg/mL, about 10 µg/mL to about 150 mg/mL, about 10 µg/mL to about 100 mg/mL, about 10 µg/mL to about 50 mg/mL, about 10 µg/mL to about 25 mg/mL, about 25 µg/mL to about 750 mg/mL, about 25 µg/mL to about 500 mg/mL, about 25 µg/mL to about 300 mg/mL, about 25 µg/mL to about 150 mg/mL, about 25 µg/mL to about 100 mg/mL, about 25 µg/mL to about 50 mg/mL, about 50 µg/mL to about 750 mg/mL, about 50 µg/mL to about 500 mg/mL, about 50 µg/mL to about 300 mg/mL, about 50 µg/mL to about 150 mg/mL, about 50 µg/mL to about 100 mg/mL, about 100 µg/mL to about 750 mg/mL, about 100 µg/mL to about 500 mg/mL, about 100 µg/mL to about 300 mg/mL, about 100 µg/mL to about 150 mg/mL, about 150 µg/mL to about 750 mg/mL, about 150 µg/mL to about 500 mg/mL, about 150 µg/mL to about 300 mg/mL, about 300 µg/mL to about 750 mg/mL, about 300 µg/mL to about 500 mg/mL, or about 500 µg/mL to about 750 mg/mL.

In some embodiments, the dosage of the at least one specifically deuterated ETBR antagonist, and/or at least one anti-oncologic agent can independently be about 0.1 µg to about 5000 µg, about 0.1 µg to about 4500 µg, about 0.1 µg to about 4000 µg, about 0.1 µg to about 3500 µg, about 0.1 µg to about 3000 µg, about 0.1 µg to about 2500 µg, about 0.1 µg to about 2000 µg, about 0.1 µg to about 1500 µg, about 0.1 µg to about 1000 µg, about 0.1 µg to about 500 µg, about 1.0 µg to about 5000 µg, about 1.0 µg to about 4500 µg, about 1.0 µg to about 4000 µg, about 1.0 µg to about 3500 µg, about 1.0 µg to about 3000 µg, about 1.0 µg to about 2500 µg, about 1.0 µg to about 2000 µg, about 1.0 µg to about 1500 µg, about 1.0 g to about 1000 µg, about 1.0 µg to about 500 µg, about 100 µg to about 5000 µg, about 100 µg to about 4500 µg, about 100 µg to about 4000 µg, about 100 µg to about 3500 µg, about 100 µg to about 3000 µg, about 100 µg to about 2500 µg, about 100 µg to about 2000 µg, about 100 µg to about 1500 µg, about 100 µg to about 1000 µg, about 100 µg to about 500 µg, about 250 µg to about 5000 µg, about 250 µg to about 4500 µg, about 250 µg to about 4000 µg, about 250 µg to about 3500 µg, about 250 µg to about 3000 µg, about 250 µg to about 2500 µg, about 250 µg to about 2000 µg, about 250 µg to about 1500 µg, about 250 µg to about 1000 µg, about 250 µg to about 500 µg, about 500 µg to about 5000 µg, about 500 µg to about 4500 µg, about 500 µg to about 4000 µg, about 500 µg to about 3500 µg, about 500 µg to about 3000 µg, about 500 µg to about 2500 µg, about 500 µg to about 2000 µg, about 500 µg to about 1500 µg, about 500 µg to about 1000 µg, about 750 µg to about 5000 µg, about 750 µg to about 4500 µg, about 750 µg to about 4000 µg, about 750 µg to about 3500 µg, about 750 µg to about 3000 µg, about 750 µg to about 2500 µg, about 750 µg to about 2000 µg, about 75 µg to about 1500 µg, about 750 µg to about 1000 µg, about 1500 µg to about 5000 µg, about 1500 µg to about 4500 µg, about 1500 µg to about 4000 µg, about 1500 µg to about 3500 µg, about 1500 µg to about 3000 µg, about 1500 µg to about 2500 µg, about 1500 µg to about 2000 µg, about 2000 µg to about 5000 µg, about 2000 µg to about 4500 µg, about 2000 µg to about 4000 µg, about 2000 µg to about 3500 µg, about 2000 µg to about 3000 µg, about 2000 µg to about 2500 µg, about 2500 µg to about 5000 µg, about 2500 µg to about 4500 µg, about 2500 µg to about 4000 µg, about 2500 µg to about 3500 µg, about 2500 µg to about 3000 µg, about 3000 µg to about 5000 µg, about 3000 µg to about 4500 µg, about 3500 µg to about 4000 µg, about 3500 µg to about 5000 µg, about 3500 µg to about 4500 µg, about 3500 µg to about 4000 µg, about 4000 µg to about 5000 µg, about 4000 µg to about 4500 µg, or about 4500 µg to about 5000 µg.

In some embodiments, a dosage of the anti-PD1 antibody is about 0.1 mg/kg to about 9.0 mg/kg. For example, the dosage of the anti-PD1 antibody is about 0.1 mg/kg to about 9.0 mg/kg, about 0.1 mg/kg to about 8.0 mg/kg, about 0.1 mg/kg to about 7.0 mg/kg, about 0.1 mg/kg to about 6.0 mg/kg, about 0.1 mg/kg to about 5.0 mg/kg, about 0.1 mg/kg to about 4.0 mg/kg, about 0.1 mg/kg to about 3.0 mg/kg, about 0.1 mg/kg to about 2.0 mg/kg, about 0.1 mg/kg to about 1.0 mg/kg, about 1.0 mg/kg to about 9.0 mg/kg, about 1.0 mg/kg to about 8.0 mg/kg, about 1.0 mg/kg to about 7.0 mg/kg, about 1.0 mg/kg to about 6.0 mg/kg, about 1.0 mg/kg to about 5.0 mg/kg, about 1.0 mg/kg to about 4.0 mg/kg, about 1.0 mg/kg to about 3.0 mg/kg, about 1.0 mg/kg to about 2.0 mg/kg, about 2.0 mg/kg to about 9.0 mg/kg, about 2.0 mg/kg to about 8.0 mg/kg, about 2.0 mg/kg to about 7.0 mg/kg, about 2.0 mg/kg to about 6.0 mg/kg, about 2.0 mg/kg to about 5.0 mg/kg, about 2.0 mg/kg to about 4.0 mg/kg, about 2.0 mg/kg to about 3.0 mg/kg, about 3.0 mg/kg to about 9.0 mg/kg, about 3.0 mg/kg to about 8.0 mg/kg, about 3.0 mg/kg to about 7.0 mg/kg, about 3.0 mg/kg to about 6.0 mg/kg, about 3.0 mg/kg to about 5.0 mg/kg, about 3.0 mg/kg to about 4.0 mg/kg, about 4.0 mg/kg to about 9.0 mg/kg, about 4.0 mg/kg to about 8.0 mg/kg, about 4.0 mg/kg to about 7.0 mg/kg, about 4.0 mg/kg to about 6.0 mg/kg, about 4.0 mg/kg to about 5.0 mg/kg, about 5.0 mg/kg to about 9.0 mg/kg, about 5.0 mg/kg to about 8.0 mg/kg, about 5.0 mg/kg to about 7.0 mg/kg, about 5.0 mg/kg to about 6.0 mg/kg, about 6.0 mg/kg to about 9.0 mg/kg, about 6.0 mg/kg to about 8.0 mg/kg, about 6.0 mg/kg to about 7.0 mg/kg, about 7.0 mg/kg to about 9.0 mg/kg, about 7.0 mg/kg to about 8.0 mg/kg, or about 8.0 mg/kg to about 9.0 mg/kg.

In some embodiments, a dosage of the bRAF inhibitor is about 1 mg to about 1500 mg. For example, the dosage of the bRAF inhibitor about 1 mg to about 1500 mg, about 1 mg to about 1250 mg, about 1 mg to about 1000 mg, about 1 mg to about 750 mg, about 1 mg to about 500 mg, about 1 mg to about 250 mg, about 250 mg to about 1500 mg, about 250 mg to about 1250 mg, about 250 mg to about 1000 mg, about 250 mg to about 750 mg, about 250 mg to about 500 mg, about 500 mg to about 1500 mg, about 500 mg to about 1250 mg, about 500 mg to about 1000 mg, about 500 mg to about 750 mg, about 750 mg to about 1500 mg, about 750 mg to about 1250 mg, about 750 mg to about 1000 mg, about 1000 mg to about 1500 mg, about 1000 mg to about 1250 mg, or about 1250 mg to about 1500 mg.

In some embodiments, a dosage of the niacinamide is about 1 mg to about 3000 mg. For example, the dosage of the niacinamide is about 1 mg to about 3000 mg, about 1 mg to about 2750 mg, about 1 mg to about 2500 mg, about 1 mg to about 2250 mg, about 1 mg to about 2000 mg, about 1 mg to about 1750 mg, about 1 mg to about 1500 mg, about 1 mg to about 1250 mg, about 1 mg to about 1000 mg, about 1 mg to about 750 mg, about 1 mg to about 500 mg, about 1 mg to about 250 mg, about 250 mg to about 3000 mg, about 250 mg to about 2750 mg, about 250 mg to about 2500 mg, about 250 mg to about 2250 mg, about 250 mg to about 2000 mg, about 250 mg to about 1750 mg, about 250 mg to about 1500 mg, about 250 mg to about 1250 mg, about 250 mg to about 1000 mg, about 250 mg to about 750 mg, about 250 mg to about 500 mg, about 500 mg to about 3000 mg, about 500 mg to about 2750 mg, about 500 mg to about 2500 mg, about 500 mg to about 2250 mg, about 500 mg to about 2000 mg, about 500 mg to about 1750 mg, about 500 mg to about 1500 mg, about 500 mg to about 1250 mg, about 500 mg to about 1000 mg, about 500 mg to about 750 mg, about 750 mg to about 3000 mg, about 750 mg to about 2750 mg, about 750 mg to about 2500 mg, about 750 mg to about 2250 mg, about 750 mg to about 2000 mg, about 750 mg to about 1750 mg, about 750 mg to about 1500 mg, about 750 mg to about 1250 mg, about 750 mg to about 1000 mg, about 1000 mg to about 3000 mg, about 1000 mg to about 2750 mg, about 1000 mg to about 2500 mg, about 1000 mg to about 2250 mg, about 1000 mg to about 2000 mg, about 1000 mg to about 1750 mg, about 1000 mg to about 1500 mg, about 100 mg to about 1250 mg, about 1250 mg to about 3000 mg, about 1250 mg to about 2750 mg, about 1250 mg to about 2500 mg, about 1250 mg to about 2250 mg, about 1250 mg to about 2000 mg, about 1250 mg to about 1750 mg, about 1250 mg to about 1500 mg, about 1500 mg to about 3000 mg, about 1500 mg to about 2750 mg, about 1500 mg to about 2500 mg, about 1500 mg to about 2250 mg, about 1500 mg to about 2000 mg, about 1500 mg to about 1750 mg, about 1750 mg to about 3000 mg, about 1750 mg to about 2750 mg, about 1750 mg to about 2500 mg, about 1750 mg to about 2250 mg, about 1750 mg to about 2000 mg, about 2000 mg to about 3000 mg, about 2000 mg to about 2750 mg, about 2000 mg to about 2500 mg, about 2000 mg to about 2250 mg, about 2250 mg to about 3000 mg, about 2250 mg to about 2750 mg, about 2250 mg to about 2500 mg, about 2500 mg to about 3000 mg, about 2500 mg to about 2750 mg, or about 2750 mg to about 3000 mg.

Kits

Disclosed herein is a kit or pharmaceutical compositions for treatment of a solid tumor cancer in a subject, e.g., a human subject, comprising at least one ETBR antagonist in an amount effective for use in a combination therapy with at least one immune checkpoint inhibitor, and a pharmaceutically acceptable carrier. In some embodiments, the at least one ETBR antagonist is at least one specifically deuterated ETBR antagonist, e.g., deuterated BQ-788 as described herein. In some embodiments, the at least one ETBR antagonist, e.g., deuterated BQ-788, is disposed in a single container with the immune checkpoint inhibitor. In some embodiments, the at least one ETBR antagonist, e.g., deuterated BQ-788, is disposed in a first container, and the immune checkpoint inhibitor is disposed in a second container, wherein the at least one ETBR antagonist and the immune checkpoint inhibitor are to be administered approximately contemporaneously.

In some embodiments, the description provides a kit for treatment of a solid tumor cancer in a human subject, comprising an amount of at least one immune checkpoint inhibitor, a synergistically effective amount of BQ-788, and a pharmaceutically acceptable carrier or excipient. In some embodiments, the BQ-788 is at least one deuterated BQ-788. In some embodiments, the at least one checkpoint inhibitor is an anti-PD1 antibody or anti-PD-L1 antibody.

Routes of Administration

Disclosed herein is a variety of routes of administration for the pharmaceutical compositions disclosed herein. The compounds as described herein may, in accordance with the disclosure, be administered in single or divided doses by the oral, parenteral or topical routes. Administration of the active compound may range from continuous (intravenous drip) to several oral administrations per day (for example, Q.O.D. or Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent(s) chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. In some embodiments, sustained or controlled release forms are y administered orally, but also in suppository and transdermal or other topical forms. Intramuscular injections in liposomal form may also be used to control or sustain the release of compound at an injection site.

In some embodiments, the pharmaceutical compositions as described herein is administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously.

In some embodiments, sterile injectable forms of the compositions as described herein are aqueous or oleaginous suspension. These suspensions may be formulated using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil, castor oil or soybean oil, especially in their polyoxyethylated versions. These oil solutions or suspensions may also contain a long-chain alcohol diluent or dispersant, such as Ph. Helv or similar alcohol.

In some embodiments, the pharmaceutical compositions as described herein are orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are used orally, the active ingredient is combined with emulsifying and suspending agents. If desired, certain sweetening, flavoring or coloring agents may also be added.

In some embodiments, the pharmaceutical compositions as described herein are administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

In some embodiments, the pharmaceutical compositions as described herein are administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

In some embodiments, for topical applications, the pharmaceutical compositions are formulated in a suitable ointment containing the active component suspended or dissolved in one or more carriers. Carriers for topical administration of the compounds of this disclosure include, but are not limited to, mineral oil, liquid petrolatum, DMSO, white petrolatum, propylene glycol, polyoxyethylene, polyoxypropylene compound, emulsifying wax and water. In some embodiments, the compounds may be coated onto a stent which is to be surgically implanted into a patient in order to inhibit or reduce the likelihood of occlusion occurring in the stent in the patient.

In some embodiments, the pharmaceutical compositions are formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In some embodiments, for ophthalmic use, the pharmaceutical compositions are formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutical compositions may be formulated in an ointment such as petrolatum.

In some embodiments, the pharmaceutical compositions as described herein are administered by nasal aerosol or inhalation. Such compositions are prepared according to techniques described herein relating to pharmaceutical compositions and may be prepared as solutions in saline, employing benzyl alcohol or other suitable preservatives, absorption promoters to enhance bioavailability, fluorocarbons, and/or other conventional solubilizing or dispersing agents. In some embodiments, the description provides formulations comprising liposomes including an effective amount (e.g., a synergistically effective amount) of at least one of a ETBR antagonist or a caspase-8 inhibitor or a combination thereof, and/or an effective amount (e.g., a synergistically effective amount) of at least one of an ETAR antagonist, an anti-PD1 antibody, a bRAF inhibitor, niacinamide or a combination thereof, wherein the liposome formulation is configured or adapted for intranasal delivery or sublingual delivery. In a further embodiment, the liposomes further comprise an additional anti-cancer agent as described above.

In some embodiments, the compositions should be formulated to contain between about 0.05 milligram to about 750 milligrams or more, for example about 1 milligram to about 600 milligrams, or about 10 milligrams to about 500 milligrams of active ingredient, alone or in combination with at least one other compound according to the present disclosure. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

In some embodiments, a patient or subject in need of therapy using compounds according to the methods described herein is treated by administering to the patient (subject) an effective amount of the compound according to the present disclosure including pharmaceutically acceptable salts, solvates or polymorphs thereof optionally in a pharmaceutically acceptable carrier or diluent, either alone, or in combination with other known erythopoiesis stimulating agents as otherwise identified herein.

In some embodiments, the compounds or compositions herein are administered orally, parenterally, intradermally, by an injection (intravenously, subcutaneously, or intramuscularly), topically, including transdermally, in liquid, cream, gel, or solid form, or by aerosol form.

In some embodiments, the active ingredients are included in the pharmaceutically acceptable carrier or diluent in an amount sufficient to deliver to a patient a therapeutically effective amount for the desired indication, without causing serious toxic effects in the patient treated. An exemplary dose of the active compound for all of the herein-mentioned conditions is in the range from about 10 ng/kg to 300 ng/kg, about 10 ng/kg to 1 µg/kg, about 1 µg/kg to 10 µg/kg, about 10 µg/kg to 100 µg/kg, about 100 µg/kg to 1000 µg/kg, about 1 mg/kg to 30 mg/kg, about 1 mg/kg to 300 mg/kg, or 0.1 to 100 mg/kg per day, more generally 0.5 to about 25 mg per kilogram body weight of the recipient/patient per day. A typical topical dosage will range from 0.01-5% wt/wt in a suitable carrier.

In some embodiments, the active ingredient herein is conveniently administered in any suitable unit dosage form, including but not limited to, one containing less than 1 mg, 1 mg to 3000 mg, for example 5 to 500 mg of active ingredient per unit dosage form. An oral dosage of about 25-250 mg is often convenient.

In some embodiments, the active ingredient is administered to achieve peak plasma concentrations of the active compound of about 0.00001-30 mM, for example about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

Methods for Treatment

Disclosed herein are methods for treating or ameliorating a disease, disorder or symptom thereof in a subject or a patient, e.g., an animal such as a human, comprising administering to a subject in need thereof an effective amount, e.g., a therapeutically effective amount or a synergistically effective amount, of a pharmaceutical composition as described herein, wherein the composition is effective for treating or ameliorating the disease or disorder or symptom thereof in the subject. In some embodiments, the disease or disorder is an ETBR-related cancer or a cancer that is insensitive to immune based therapy or both. In some embodiments, the pharmaceutical composition comprises an effective amount of a specifically deuterated ETBR antagonist, e.g., deuterated BQ-788 or BQ-788-B, as described herein. In some embodiments, the ETBR-related cancer is at least one of breast cancer, metastatic breast cancer, melanoma, squamous cell carcinoma, glioblastoma or a combination thereof. In some embodiments, the cancer is a solid tumor cancer. In some embodiments, the ETBR-related cancer to be treated does not include breast cancer, melanoma, metastatic breast cancer or metastatic melanoma.

In some embodiments, the administration of a specifically deuterated ETBR antagonist alone or in a combination with administration of at least one ETBR antagonist and an immune checkpoint inhibitor is sufficient to effectuate the treatment or amelioration of at least one symptom of cancer. In some embodiments, administration of the ETBR antagonist alone or in a combination with immune checkpoint inhibitor effectuates stimulation or enhancement of tumor infiltrating lymphocytes, macrophages, tertiary lymphoid organ formation or a combination thereof. In some embodiments, treatment or amelioration of cancer or stimulation or enhancement of tumor infiltrating lymphocytes, macrophages, induce tertiary lymphoid organ formation or a combination thereof, as determined using a V600E+SM1 cancer model in mice, e.g., C57BL/6 mouse model. In some embodiments, the at least one ETBR antagonist and immune checkpoint inhibitor (whether in single formulation or separate) are administered in unit dosage forms. In some embodiments, the unit dosage form or forms comprises a synergistically effective amount of each of the at least one ETBR antagonist, and the immune checkpoint inhibitor.

In some embodiments, the description provides methods for treating cancer in a subject, e.g., a solid tumor cancer, comprising administering to a subject in need thereof an effective dose of a specifically deuterated ETBR antagonist as described herein alone or in a combination with an immune checkpoint inhibitor, wherein the administering effectuates the treatment or amelioration of at least one symptom of the cancer.

In some embodiments, the description provides methods of treating cancer in a subject comprising administering to a subject in need thereof an effective dose of a specifically deuterated ETBR antagonist as described herein, and administering to the subject an immune checkpoint inhibitor, wherein the administrations effectuate at least one of:
 a. enhancement or stimulation of tumor infiltrating lymphocytes (TILs),
 b. increased tumor associated macrophages (TAMs),
 c. enhancement or stimulation of tertiary lymphoid organ (TLO) formation or
 d. a combination thereof, and
thereby treating or ameliorating at least one symptom of the cancer. In some embodiments, (a)-(d) are determined in a human by biopsy or in an animal model. In some embodiments, the animal model is a V600E+ SM1 cancer model in mice, e.g., C57BL/6 mouse model.

In some embodiments, the at least one specifically deuterated ETBR antagonist is at least one deuterated form of BQ-788 as described herein. In further embodiments, the deuterated BQ-788 is BQ-788-A, BQ-788-B, BQ-788-C or a combination thereof.

In some embodiments, a method for treating cancer herein comprises administering to a patient in need thereof at least one ETBR antagonist, wherein the at least one ETBR antagonist is effective in treating or ameliorating at least one symptom of the cancer in the patient. In some embodiments, the at least one ETBR antagonist is at least one specifically deuterated ETBR antagonist. In some embodiments, the method comprises administering an effective amount of the at least one specifically deuterated ETBR antagonist as described herein, e.g., a deuterated form of BQ-788. In some embodiments, the deuterated BQ-788 is at least one of BQ-788-A, BQ-788-B, or BQ-788-C. In some embodiments, the cancer is an ETBR-related cancer, e.g., an ETBR-related solid tumor cancer. In some embodiments, the ETBR-related cancer is at least one of breast cancer, melanoma, squamous cell carcinoma, glioblastoma, ovarian cancer, pancreatic cancer or a combination thereof. In some embodiments, the cancer is a solid tumor cancer. In further embodiments, the cancer is not breast cancer, melanoma, metastatic breast cancer or metastatic melanoma.

In some embodiments, the method comprises administering a composition comprising an effective amount of at least one ETBR antagonist, e.g., at least one specifically deuterated ETBR antagonist as described herein, and a pharmaceutically acceptable carrier or excipient as described herein. In some embodiments, the composition is administered in unit dosage form.

In some embodiments, the method further comprises administering an additional anti-oncologic agent in combination with, e.g., either in the same or separate formulations, a specifically deuterated ETBR antagonist such as a deuterated BQ-788, as described herein. In some embodiments, the anti-oncologic agent is an anti-PD1 antibody or anti-PD-L1 antibody. In some embodiments, the anti-oncologic agent, e.g., anti-PD1 or anti-PD-L1 antibody is administered as a composition comprising a pharmaceutically acceptable carrier or excipient.

In some embodiments, the method comprises administering a combination comprising at least one specifically deuterated ETBR antagonist as described herein, and at least one additional anti-oncologic agent as described herein. In some embodiments, the combination comprises a pharmaceutically acceptable carrier or excipient. In some embodiments, the combination comprises an effective amount of at least one specifically deuterated ETBR antagonist, e.g., a deuterated BQ-788, as described herein. In some embodiments, the combination comprises an amount of an immune checkpoint inhibitor and a synergistically effective amount of the at least one specifically deuterated ETBR antagonist, such as a deuterated BQ-788. In some embodiments, the immune checkpoint inhibitor is an anti-PD1 antibody.

In some embodiments, the combination comprises an effective amount of a specifically deuterated ETBR antagonist as described herein, and a synergistically effective amount of the at least one anti-oncologic agent. In some embodiments, the combination includes a pharmaceutical acceptable carrier. In some embodiments, the combination is comprised within one or more unit dosage forms. In further embodiments, the combination is administered in separate unit dosage forms, for example, a first container comprising the at least one ETBR antagonist, and a second container comprising the at least one anti-oncologic agent, such as an immune checkpoint inhibitor. In some embodiments, the specifically deuterated ETBR antagonist is a deuterated BQ-788 as described herein.

In some embodiments, the pharmaceutical compositions are delivered intravenously, intramuscularly, subcutaneously, orally, intranasally, sublingually, transdermally, topically, intraperitoneally, parenterally, intranasally, or intracranially.

In some embodiments, the ETBR-antagonist, e.g., deuterated ETBR-antagonist or deuterated BQ-788, is administered in the form of a liposomal formulation as described herein.

In some embodiments, a method for treating ETBR-related metastatic brain cancer is provided. The method comprises administering an effective amount to a subject in need thereof a pharmaceutical composition of the present disclosure, wherein the pharmaceutical composition is effective for treating or ameliorating a symptom of ETBR-related metastatic brain cancer. In some embodiments, the ETBR-related metastatic brain cancer is metastatic melanoma-related brain cancer, metastatic squamous cell carcinoma-related brain cancer, glioblastoma or a combination thereof. In some embodiments, the composition comprises an effective amount of a specifically deuterated ETBR antagonist, e.g., a deuterated BQ-788 as described herein, and a pharmaceutically acceptable carrier.

In some embodiments, the description provides methods for treating a solid tumor cancer in a human subject, comprising administering effective doses of an ETBR antagonist and further administering an immune checkpoint inhibitor to the subject in need thereof, wherein the administration of the ETBR antagonist and immune checkpoint inhibitor effectuates at least one of: (i) enhancement or stimulation of tumor infiltrating lymphocytes (TILs), (ii) increased tumor associated macrophages (TAMs), (iii) enhancement or stimulation of tertiary lymphoid organ (TLO) formation or (iv) a combination thereof, wherein the ETBR antagonist and immune checkpoint inhibitor effectuate the treatment or alleviation of at least one symptom of the solid tumor cancer. In some embodiments, the formation of (i)-(iv) is performed in a mouse model. In some embodiments, the mouse model is the V600E+ SM1 cancer model in C57BL/6 mice. In some embodiments, the immune checkpoint inhibitor is an anti-PD1 or anti-PD-L1 antibody.

In some embodiments, the effective dose is a synergistically effective amount, e.g., from 0.1 μg to 5000 mg. In some embodiments, the specifically deuterated ETBR antagonist is a deuterated BQ-788. In some embodiments, the deuterated BQ-788 is BQ-788-B. In some embodiments, the specifically deuterated ETBR antagonist, e.g., deuterated BQ-788, includes a pharmaceutically acceptable carrier or excipient. In some embodiments, the ETBR antagonist (e.g., deuterated ETBR such as deuterated BQ-788) and immune checkpoint inhibitor are administered separately. In some embodiments, the ETBR antagonist (e.g., deuterated ETBR such as deuterated BQ-788) and immune checkpoint inhibitor are administered in the same formulation.

In some embodiments, the description provides a method of treating an ETBR-related solid tumor cancer in a subject comprising administering to a subject in need thereof, e.g., a human, at least one deuterated BQ-788 at an effective amount or synergistically effective amount with an immune checkpoint inhibitor, and a pharmaceutically acceptable carrier or excipient, wherein the deuterated BQ-788 and immune checkpoint inhibitor effectuate the treatment or amelioration of at least one symptom of the ETBR-related solid tumor cancer in the subject. In some embodiments, the deuterated BQ-788 is administered as a liposomal formulation.

In some embodiments, the immune based therapy includes at least one of an immune checkpoint inhibitor (e.g., an anti-PD-1 antibody), a cancer vaccine, a Chimeric Antigen Receptor T-Cell (CAR-T) therapy or a combination thereof.

In some embodiments, the description provides a method of inhibiting melanoma invasion and metastasis in a patient comprising administering to a subject in need thereof an effective amount, e.g., a therapeutically effective amount or a synergistically effective amount, of a pharmaceutical composition as described herein, wherein the composition is effective for inhibiting melanoma invasion and metastasis.

In some embodiments, the description provides a method of inducing melanoma cell death (apoptosis) comprising administering to a subject in need thereof an effective amount, e.g., a therapeutically effective amount or a synergistically effective amount, of a pharmaceutical composition as described herein, wherein the composition is effective for inducing melanoma cell death.

In some embodiments, the description provides a method of inhibiting blood supply to melanoma tumors in a patient comprising administering to a subject in need thereof an effective amount, e.g., a therapeutically effective amount or a synergistically effective amount, of a pharmaceutical composition as described herein, wherein the composition is effective for inhibiting blood supply to melanoma tumors.

In some embodiments, the pharmaceutical composition comprises about 1% to about 95% of the active ingredient, single-dose forms of administration comprising about 20% to about 90% of the active ingredient and administration forms which are not single-dose comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

In some embodiments, the active ingredient is included in the pharmaceutically acceptable carrier or diluent in an amount sufficient to deliver to a patient a therapeutically effective amount for the desired indication, without causing serious toxic effects in the patient treated. An exemplary dose of the active compound for all of the herein-mentioned conditions is in the range from about 10 ng/kg to 300 mg/kg, for example 0.1 to 100 mg/kg per day, more generally 0.5 to about 25 mg per kilogram body weight of the recipient/patient per day. A typical topical dosage will range from 0.01-5% wt/wt in a suitable carrier. The compound is conveniently administered in any suitable unit dosage form, including but not limited to one containing less than 1 mg, 1 mg to 3000 mg, for example 5 to 500 mg of active ingredient per unit dosage form. An oral dosage of about 25-250 mg is often convenient. In some embodiments, the active ingredient is administered to achieve peak plasma concentrations of the active compound of about 0.00001-30 mM, for example about 0.1-30 μM.

Dosage Regimen

Disclosed herein is a treatment regimen. In some embodiments, the treatment regimen includes a dosage pharmaceutical composition with about 100 μg to about 4000 μg of each included active ingredient (i.e., at least one specifically deuterated ETBR antagonist as described herein, the ETAR antagonist, the anti-PD1 antibody, the bRAF inhibitor, the niacinamide, or the caspase-8 inhibitor). The dosage can be a sustained release dosage in which about 50 μg to about 3000 μg of each of the active ingredients is an initial burst, while about 50 μg to about 3000 μg of the each of the active ingredients is a sustained release over 2 hours.

In some embodiments, each of the active ingredient of a pharmaceutical composition of the present disclosure can be present in any of the dosage formulation (e.g., initial burst, sustained release dosage, etc.) in about 100 μg to about 4000 μg, about 100 μg to about 3750 μg, about 100 μg to about 3500 μg, about 100 μg to about 3250 μg, about 100 μg to about 3000 μg, about 100 μg to about 2750 μg, about 100 μg to about 2500 μg, about 100 μg to about 2250 μg, about 100 μg to about 2000 μg, about 100 μg to about 1750 μg, about 100 μg to about 1500 μg, about 100 μg to about 1250 μg, about 100 μg to about 1000 μg, about 100 μg to about 750 μg, about 100 μg to about 500 μg, about 250 μg to about 4000 μg, about 250 μg to about 3750 μg, about 250 μg to about 3500 μg, about 250 μg to about 3250 μg, about 250 μg to about 3000 μg, about 250 μg to about 2750 μg, about 250 μg to about 2500 μg, about 250 μg to about 2250 μg, about 250 μg to about 2000 μg, about 250 μg to about 1750 μg, about 250 μg to about 1500 μg, about 250 μg to about 1250 μg, about 250 μg to about 1000 μg, about 250 μg to about 750 μg, about 250 μg to about 500 μg, about 500 μg to about 4000 μg, about 500 μg to about 3750 μg, about 500 μg to about 3500 μg, about 500 μg to about 3250 μg, about 500 μg to about 3000 μg, about 500 μg to about 2750 μg, about 500 μg to about 2500 μg, about 500 μg to about 2250 μg, about 500 μg to about 2000 μg, about 500 μg to about 1750 μg, about 500 μg to about 1500 μg, about 500 μg to about 1250 μg, about 500 μg to about 1000 μg, about 500 μg to about 750 μg, about 750 μg to about 4000 μg, about 750 μg to about 3750 μg, about 750 μg to about 3500 μg, about 750 μg to about 3250 μg, about 750 μg to about 3000 μg, about 750 μg to about 2750 μg, about 750 μg to about 2500 μg, about 750 μg to about 2250 μg, about 750 μg to about 2000 μg, about 750 μg to about 1750 μg, about 750 μg to about 1500 μg, about 750 μg to about 1250 μg, about 750 μg to about 1000 μg, about 1000 μg to about 4000 μg, about 1000 μg to about 3750 μg, about 1000 μg to about 3500 μg, about 1000 μg to about 3250 μg, about 1000 μg to about 3000 μg, about 1000 μg to about 2750 μg, about 1000 μg to about 2500 μg, about 1000 μg to about 2250 μg, about 1000 μg to about 2000 μg, about 1000 μg to about 1750 μg, about 1000 μg to about 1500 µg, about 1000 µg to about 1250 µg, about 1250 µg to about 4000 µg, about 1250 µg to about 3750 µg, about 1250 µg to about 3500 µg, about 1250 µg to about 3250 µg, about 1250 µg to about 3000 µg, about 1250 µg to about 2750 µg, about 1250 µg to about 2500 µg, about 1250 µg to about 2250 µg, about 1250 µg to about 2000 µg, about 1250 µg to about 1750 µg, about 1250 µg to about 1500 µg, about 1500 µg to about 4000 µg, about 1500 µg to about 3750 µg, about 1500 µg to about 3500 µg, about 1500 µg to about 3250 µg, about 1500 µg to about 3000 µg, about 1500 µg to about 2750 µg, about 1500 µg to about 2500 µg, about 1500 µg to about 2250 µg, about 1500 µg to about 2000 µg, about 1500 µg to about 1750 µg, about 1750 µg to about 4000 µg, about 1750 µg to about 3750 µg, about 1750 µg to about 3500 µg, about 1750 µg to about 3250 µg, about 1750 µg to about 3000 µg, about 1750 µg to about 2750 µg, about 1750 µg to about 2500 µg, about 1750 µg to about 2250 µg, about 1750 µg to about 2000 µg, about 2000 µg to about 4000 µg, about 2000 µg to about 3750 µg, about 2000 µg to about 3500 µg, about 2000 µg to about 3250 µg, about 2000 µg to about 3000 µg, about 2000 µg to about 2750 µg, about 2000 µg to about 2500 µg, about 2000 µg to about 2250 µg, about 2250 µg to about 4000 µg, about 2250 µg to about 3750 µg, about 2250 µg to about 3500 µg, about 2250 µg to about 3250 µg, about 2250 µg to about 3000 µg, about 2250 µg to about 2750 µg, about 2250 µg to about 2500 µg, about 2500 µg to about 4000 µg, about 2500 µg to about 3750 µg, about 2500 µg to about 3500 µg, about 2500 µg to about 3250 µg, about 2500 µg to about 3000 µg, about 2500 µg to about 2750 µg, about 2750 µg to about 4000 µg, about 2750 µg to about 3750 µg, about 2750 µg to about 3500 µg, about 2750 µg to about 3250 µg, about 2750 µg to about 3000 µg, about 3000 µg to about 4000 µg, about 3000 µg to about 3750 µg, about 3000 µg to about 3500 µg, about 3000 µg to about 3250 µg, about 3250 µg to about 4000 µg, about 3250 µg to about 3750 µg, about 3250 µg to about 3500 µg, about 3500 µg to about 4000 µg, about 3500 µg to about 3750 µg, or about 3750 µg to about 4000 µg.

In some embodiments, each active ingredient of a pharmaceutical composition of the present disclosure is present in about 0.1 mg/mL to about 50 mg/mL, about 0.1 mg/mL to about 25 mg/mL, about 0.1 mg/mL to about 10 mg/mL, about 1 mg/mL to about 50 mg/mL, about 1 mg/mL to about 25 mg/mL, about 1 mg/mL to about 10 mg/mL, about 0.1 mg/mL to about 5.0 mg/mL (e.g., about 0.1 mg/mL to about 4.5 mg/mL, about 0.1 mg/mL to about 4.0 mg/mL, about 0.1 mg/mL to about 3.5 mg/mL, about 0.1 mg/mL to about 3.0 mg/mL, about 0.1 mg/mL to about 2.5 mg/mL, about 0.1 mg/mL to about 2.0 mg/mL, about 0.1 mg/mL to about 1.5 mg/mL, about 0.1 mg/mL to about 1.0 mg/mL, about 0.1 mg/mL to about 0.5 mg/mL, about 0.5 mg/mL to about 4.5 mg/mL, about 0.5 mg/mL to about 4.0 mg/mL, about 0.5 mg/mL to about 3.5 mg/mL, about 0.5 mg/mL to about 3.0 mg/mL, about 0.5 mg/mL to about 2.5 mg/mL, about 0.5 mg/mL to about 2.0 mg/mL, about 0.5 mg/mL to about 1.5 mg/mL, about 0.5 mg/mL to about 1.0 mg/mL, about 1.0 mg/mL to about 4.5 mg/mL, about 1.0 mg/mL to about 4.0 mg/mL, about 1.0 mg/mL to about 3.5 mg/mL, about 1.0 mg/mL to about 3.0 mg/mL, about 1.0 mg/mL to about 2.5 mg/mL, about 1.0 mg/mL to about 2.0 mg/mL, about 1.0 mg/mL to about 1.5 mg/mL, about 1.5 mg/mL to about 4.5 mg/mL, about 1.5 mg/mL to about 4.0 mg/mL, about 1.5 mg/mL to about 3.5 mg/mL, about 1.5 mg/mL to about 3.0 mg/mL, about 1.5 mg/mL to about 2.5 mg/mL, about 1.5 mg/mL to about 2.0 mg/mL, about 2.0 mg/mL to about 4.5 mg/mL, about 2.0 mg/mL to about 4.0 mg/mL, about 2.0 mg/mL to about 3.5 mg/mL, about 2.0 mg/mL to about 3.0 mg/mL, about 2.0 mg/mL to about 2.5 mg/mL, about 2.5 mg/mL to about 4.5 mg/mL, about 2.5 mg/mL to about 4.0 mg/mL, about 2.5 mg/mL to about 3.5 mg/mL, about 2.5 mg/mL to about 3.0 mg/mL, about 3.0 mg/mL to about 4.5 mg/mL, about 3.0 mg/mL to about 4.0 mg/mL, about 3.0 mg/mL to about 3.5 mg/mL, about 3.5 mg/mL to about 4.5 mg/mL, about 3.5 mg/mL to about 4.0 mg/mL, or about 3.5 mg/mL to about 4.5 mg/mL, relative to the pharmaceutical composition).

In some embodiments, each active ingredient of a pharmaceutical composition of the present disclosure is present in about 0.1 µg/mL to about 50 µg/mL, about 0.1 µg/mL to about 25 µg/mL, about 0.1 µg/mL to about 10 µg/mL, about 1 µg/mL to about 50 µg/mL, about 1 µg/mL to about 25 µg/mL, about 1 µg/mL to about 10 µg/mL, about 0.1 µg/mL to about 5.0 µg/mL, e.g., about 1 µg/mL to about 5 µg/mL, about 0.1 µg/mL to about 4.0 µg/mL, about 0.1 µg/mL to about 3.5 µg/mL, about 0.1 µg/mL to about 3.0 µg/mL, about 0.1 µg/mL to about 2.5 µg/mL, about 0.1 µg/mL to about 2.0 µg/mL, about 0.1 µg/mL to about 1.5 µg/mL, about 0.1 µg/mL to about 1.0 µg/mL, about 0.1 µg/mL to about 0.5 µg/mL, about 0.5 µg/mL to about 4.5 µg/mL, about 0.5 µg/mL to about 4.0 µg/mL, about 0.5 µg/mL to about 3.5 µg/mL, about 0.5 µg/mL to about 3.0 µg/mL, about 0.5 µg/mL to about 2.5 µg/mL, about 0.5 µg/mL to about 2.0 µg/mL, about 0.5 µg/mL to about 1.5 µg/mL, about 0.5 µg/mL to about 1.0 µg/mL, about 1.0 µg/mL to about 4.5 µg/mL, about 1.0 µg/mL to about 4.0 µg/mL, about 1.0 µg/mL to about 3.5 µg/mL, about 1.0 µg/mL to about 3.0 µg/mL, about 1.0 µg/mL to about 2.5 µg/mL, about 1.0 µg/mL to about 2.0 µg/mL, about 1.0 µg/mL to about 1.5 µg/mL, about 1.5 µg/mL to about 4.5 µg/mL, about 1.5 µg/mL to about 4.0 µg/mL, about 1.5 µg/mL to about 3.5 µg/mL, about 1.5 µg/mL to about 3.0 µg/mL, about 1.5 µg/mL to about 2.5 µg/mL, about 1.5 µg/mL to about 2.0 µg/mL, about 2.0 µg/mL to about 4.5 µg/mL, about 2.0 µg/mL to about 4.0 µg/mL, about 2.0 µg/mL to about 3.5 µg/mL, about 2.0 µg/mL to about 3.0 µg/mL, about 2.5 µg/mL to about 4.5 µg/mL, about 2.5 µg/mL to about 4.0 µg/mL, about 2.5 µg/mL to about 3.5 µg/mL, about 2.5 µg/mL to about 3.0 µg/mL, about 3.0 µg/mL to about 4.5 µg/mL, about 3.0 µg/mL to about 4.0 µg/mL, about 3.0 µg/mL to about 3.5 µg/mL, about 3.5 µg/mL to about 4.5 µg/mL, about 3.5 µg/mL to about 4.0 µg/mL, or about 3.5 µg/mL to about 4.5 µg/mL, relative to the pharmaceutical composition.

EXAMPLES

Example 1. Synthesis of Deuterated ETBR Antagonists

Deuterated ETBR antagonists may be prepared by deuterating known and commercial ETBR antagonists by standard methods and procedures.

Specific deuterated ETBR antagonists may be prepared by the schemes presented below. BQ-788-B can be prepared by the method demonstrated in FIG. 14.

Figure 14:
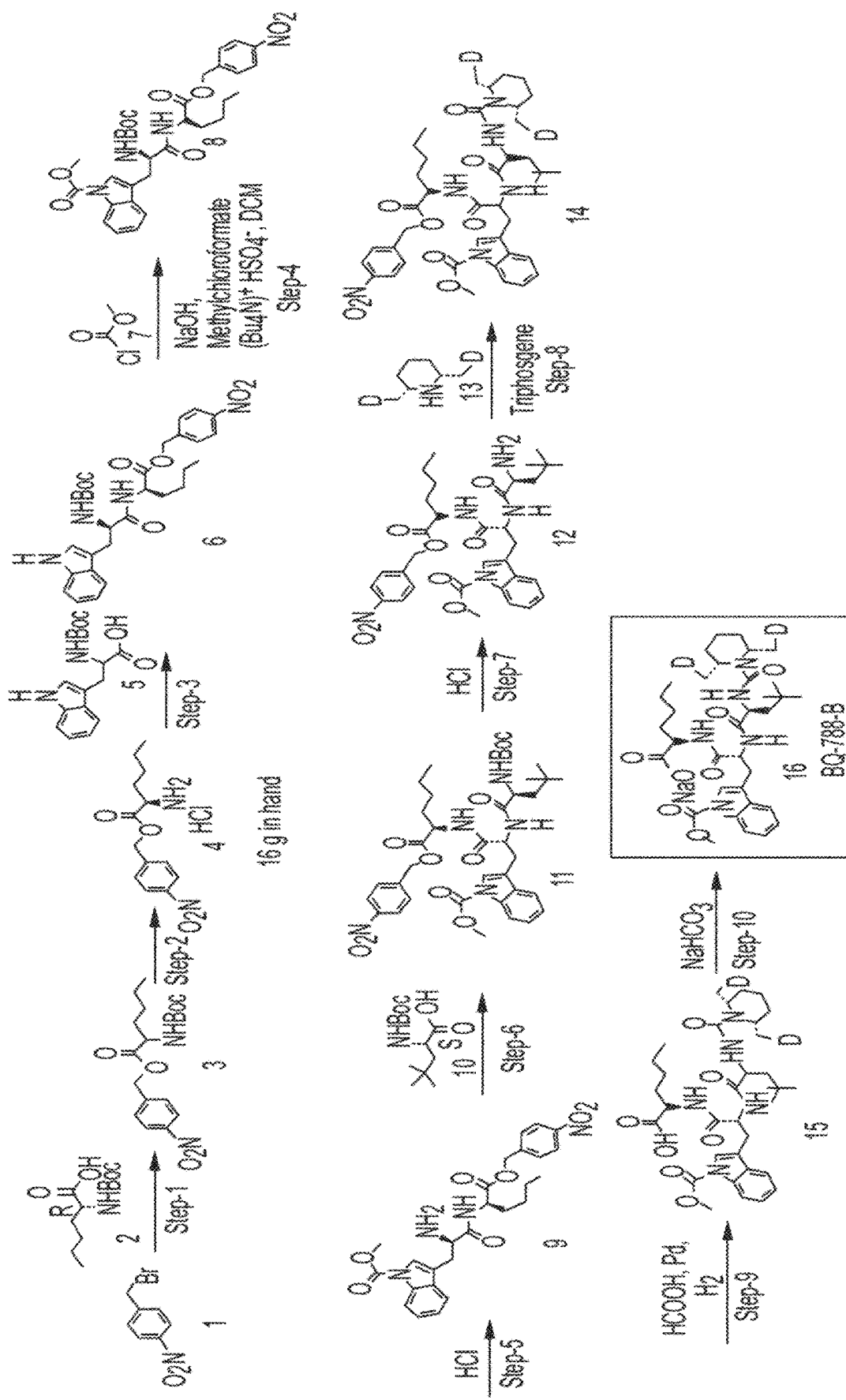
FIG. 14 depicts an exemplary synthetic scheme for preparation of specifically deuterated ETRB antagonists.
Figure 15:
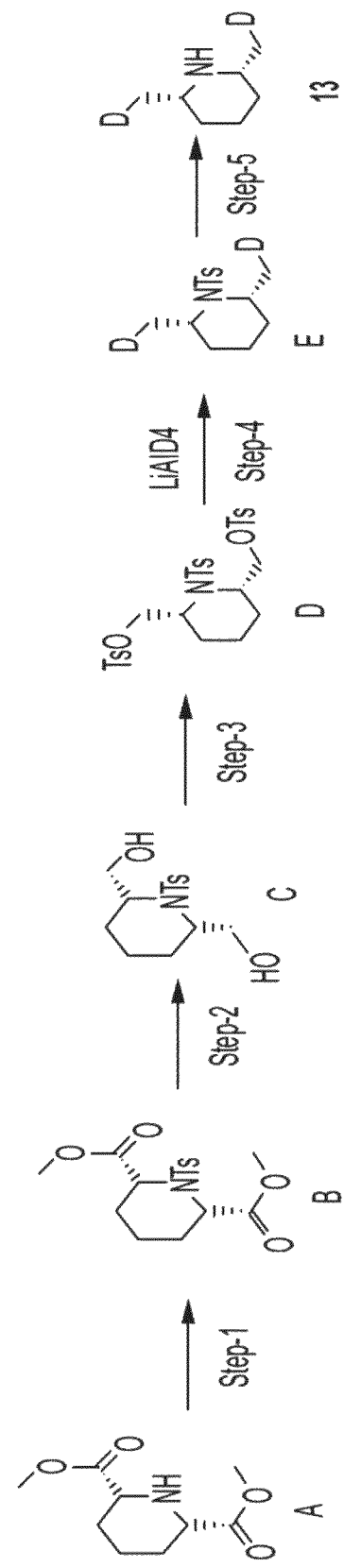
FIG. 15 depicts an exemplary synthetic scheme for preparation of intermediates for synthesis of specifically deuterated ETRB antagonists.

Intermediate 13 of FIG. 14 can be prepared by the following scheme 2 depicted in FIG. 15 (Intermediate 13):

A non-deuterated analog of Intermediate 13 can be prepared by substituting LiAlH$_4$ in place of LiAlD$_4$ in Step 4.

Figure 16:
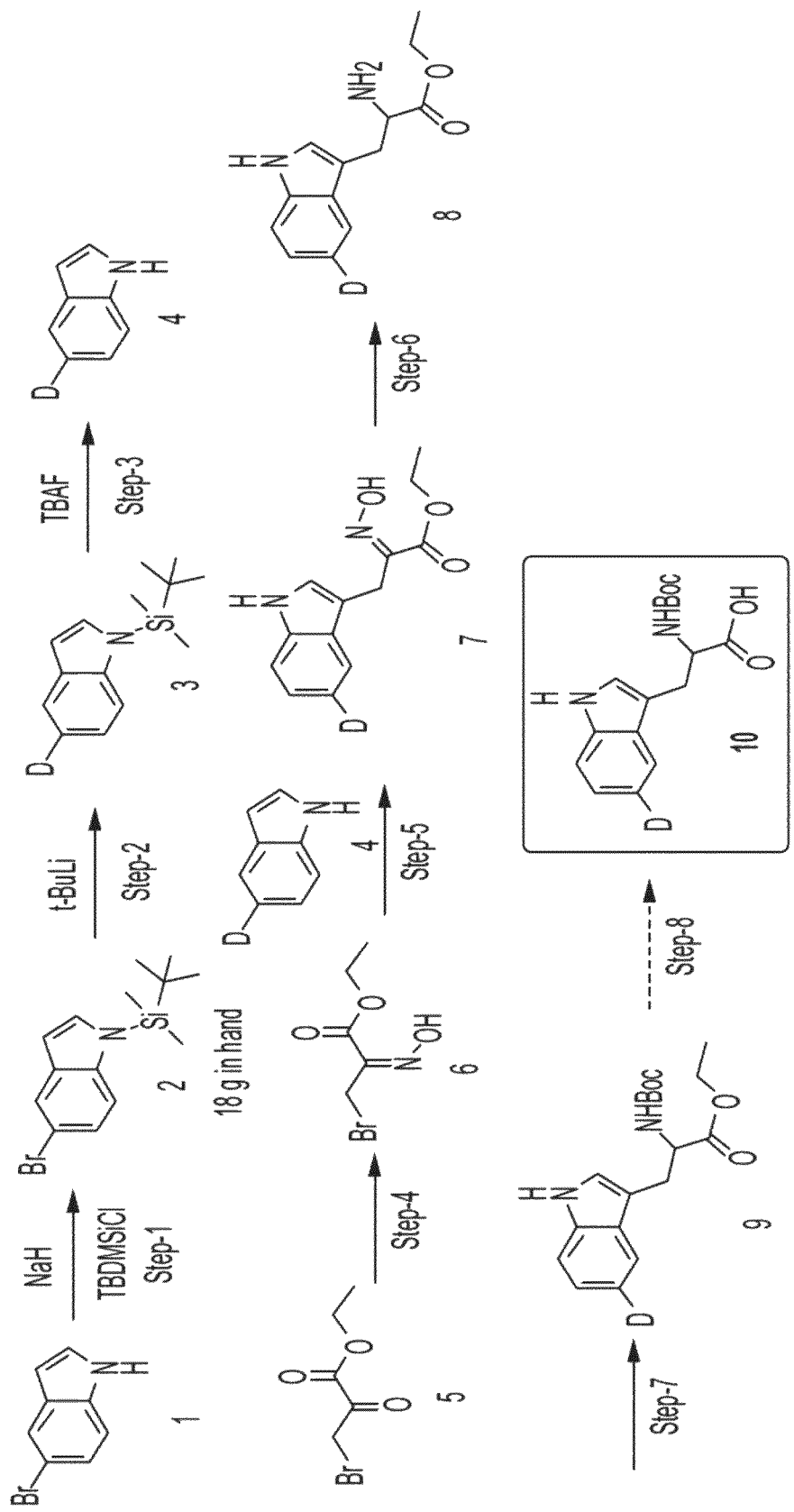
FIG. 16 depicts an exemplary synthetic scheme for preparation of intermediates for synthesis of the specifically deuterated ETRB antagonists BQ-788-A and BQ-788-C.

BQ-788-A and BQ-788-C can be prepared by substituting a deuterated analog of Intermediate 5 in Step 3 of scheme 1. Such an analog can be prepared by the method demonstrated in FIG. 16 (Intermediate 5d) below:

Compound 10 from Scheme 3 is then used in place of Compound 5 in scheme 1. For BQ-788-C Scheme 1 is then followed to completion. For BQ-788-A, the non-deuterated analog of Intermediate 13 of Scheme 1 is used Intermediate 4 of Scheme 3 can be prepared by reacting a bromonated indole with NaBD4 in the presence of a palladium catalyst.

Figure 17:
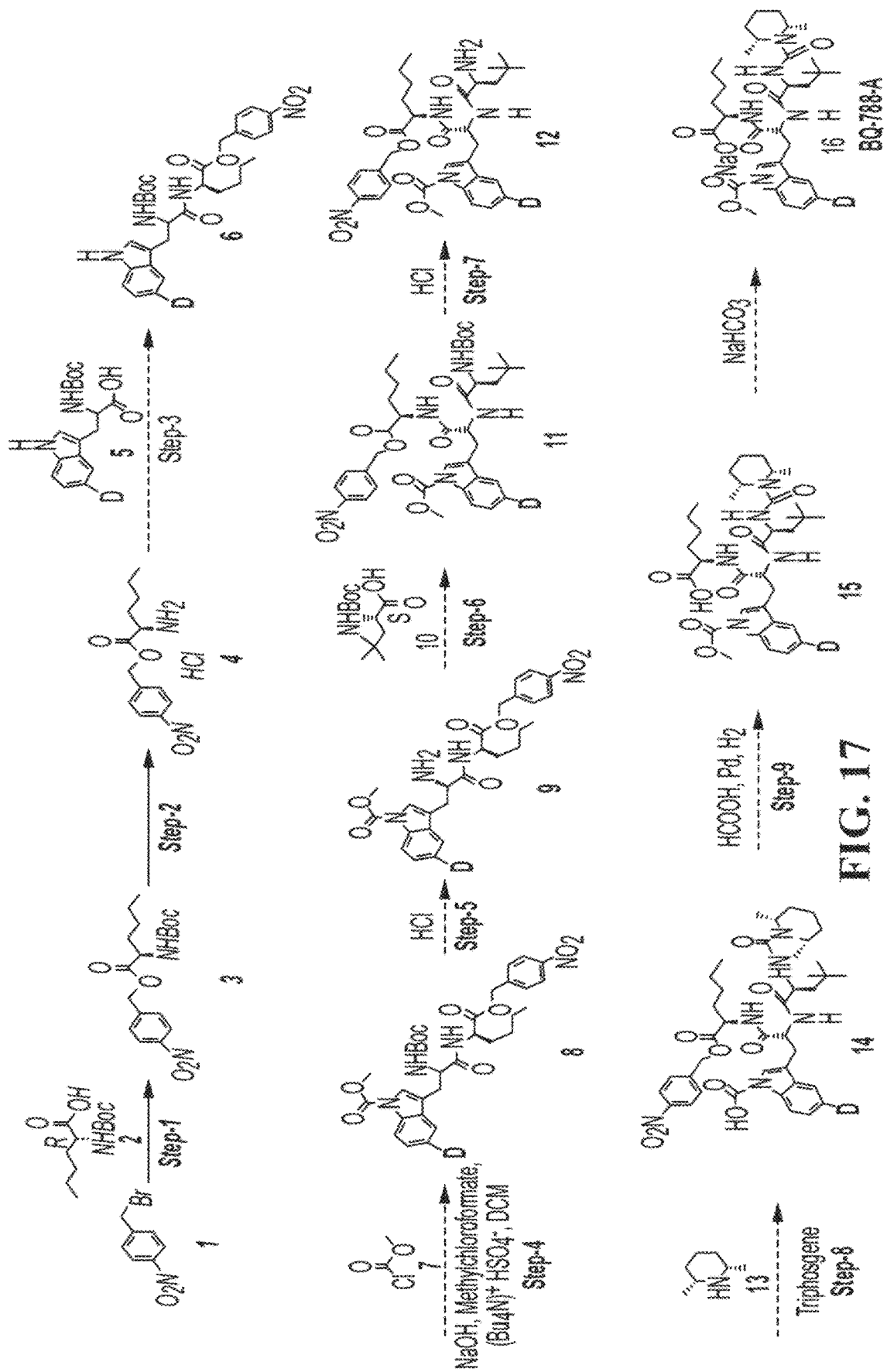
FIG. 17 depicts an exemplary synthetic scheme for preparation of the specifically deuterated ETRB antagonist BQ-788-A.

In an exemplary embodiment, compound BQ-788-A can be prepared by the method demonstrated in FIG. 17.

Figure 18:
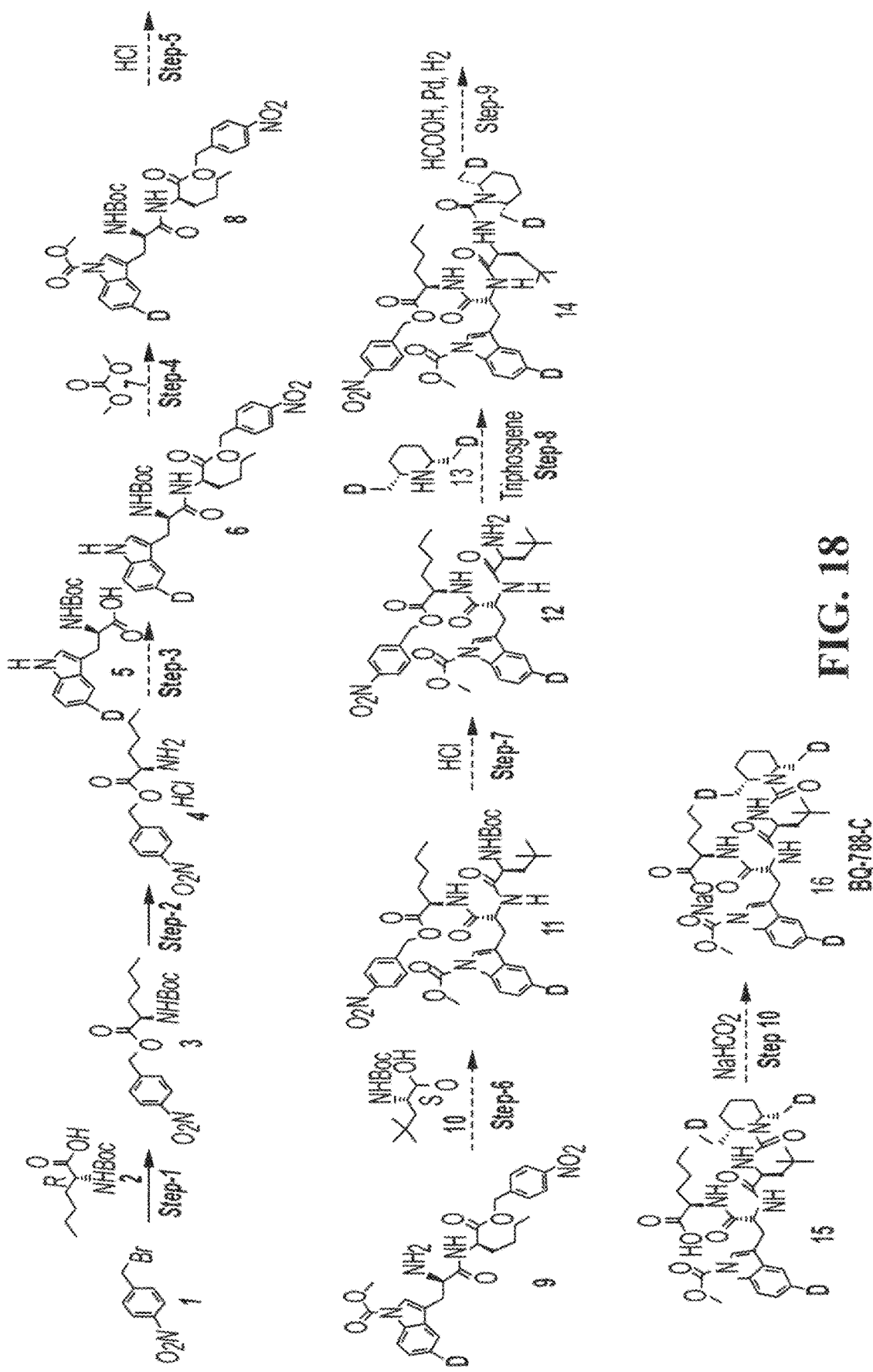
FIG. 18 depicts an exemplary synthetic scheme for preparation of the specifically deuterated ETRB antagonist BQ-788-C.

In addition, compound BQ-788-C can be prepared according to the method demonstrated in FIG. 18.

The number and position of the deuterium atoms is not to be limited by the specific schemes or examples shown herein. The preparation of compounds with more deuterium substitution can be readily extrapolated from the schemes presented here using commonly known starting materials or prepared using standard synthetic methods.

Example 2. Biological Activities of Deuterated ETBR Antagonists

Figure 4A:
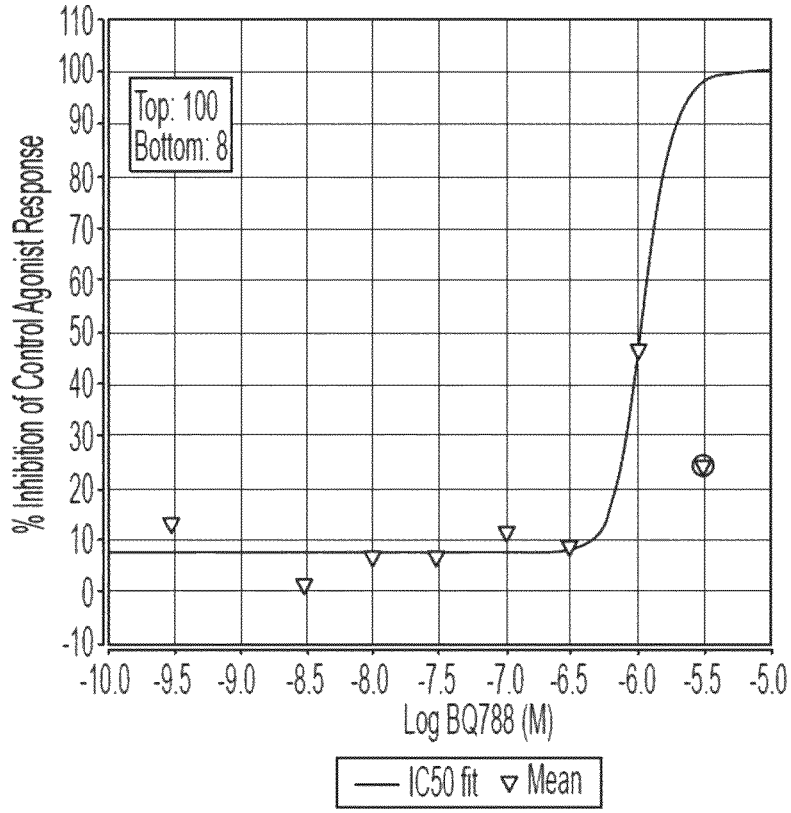
FIGS. 4A and 4B show determination of CXCR4 (h) inhibitory effect for, A) BQ-788 and B) BQ-788-B, a specifically deuterated ETRB antagonist (i.e., "Compound 1"). Cellular agonist effect was calculated as a % of control response to a known reference agonist for CXCR4 (h), and cellular antagonist effect was calculated as a % inhibition of control reference agonist response for CXCR4. Results showing ≥50% inhibition of agonist effect are considered significant while those showing less than 25% inhibition are not considered significant. The IC50 for BQ-788 was greater than about 1.0E-6 M. The IC50 for BQ-788-B was not calculable.
Figure 4B:
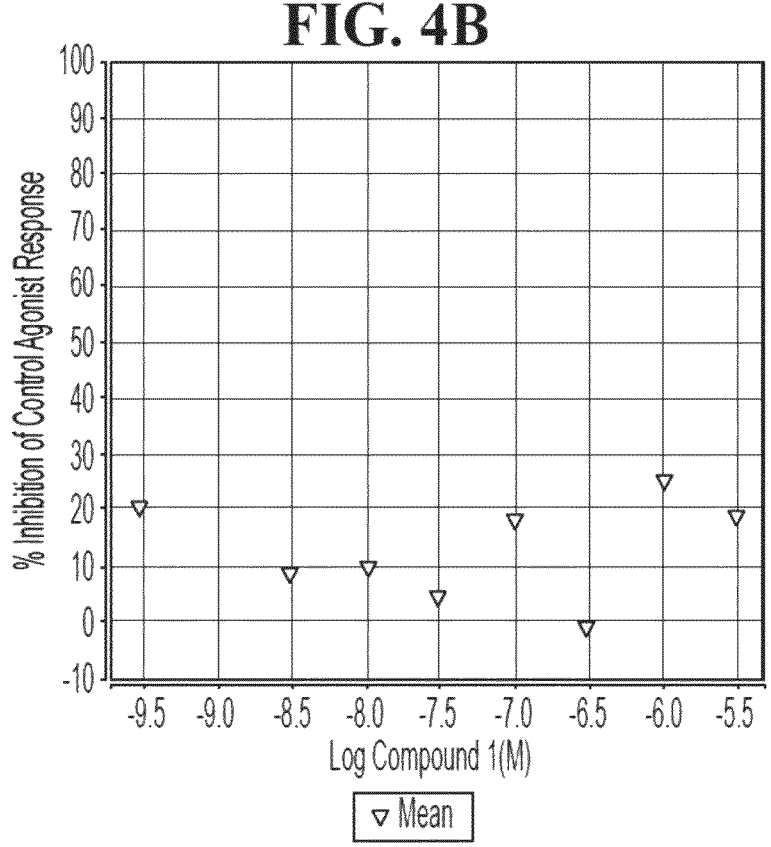

Determination of CXCR4 inhibitory effect. The inhibitory effect on CXCR4 (h) was determined for BQ-788 (FIG. 4A), and BQ-788 (FIG. 4B) BQ-788-B (i.e., "Compound 1"). Cellular agonist effect was calculated as a % of control response to a known reference agonist for CXCR4 (h), and cellular antagonist effect was calculated as a % inhibition of control reference agonist response for CXCR4. Recombinant human CXCR4 was expressed in CHO cells, and stimulated with 1 nM SDF-1α and incubated at 28° C. Dielectric spectroscopy was used to measure impedance of the cells. Results showing ≥50% inhibition of agonist effect are considered significant while those showing less than 25% inhibition are not considered significant. The IC50 for BQ-788 was greater than about 1.0E-6 M. The IC50 for BQ-788-B was not calculable.

Figure 5A:
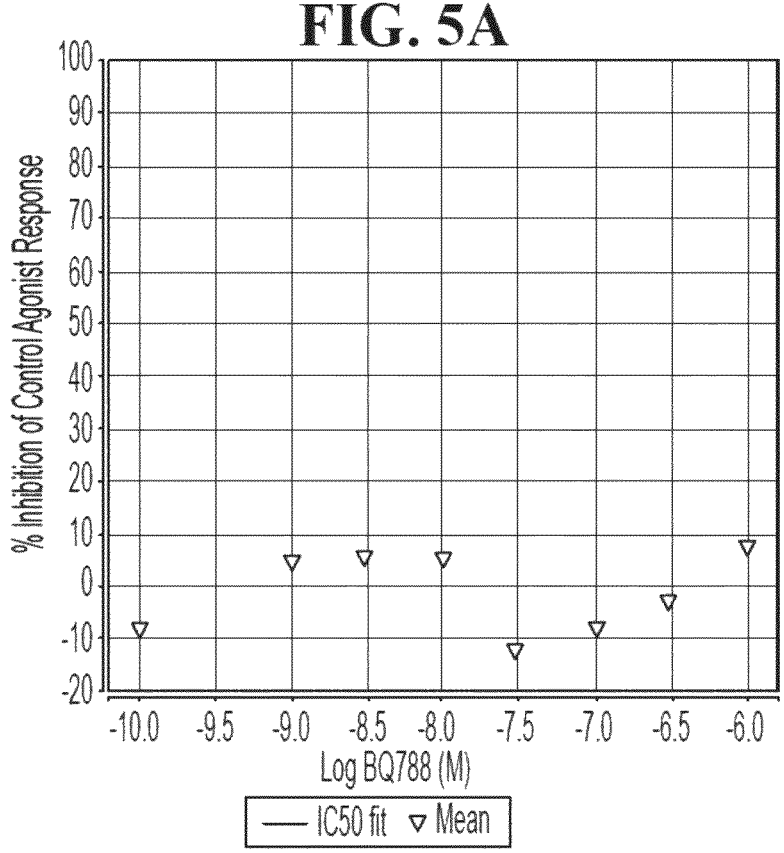
FIGS. 5A and 5B show determination of ETA (h) inhibitory effect for A) BQ-788 and B) BQ-788-B, a specifically deuterated ETRB antagonist. Cellular agonist effect was calculated as a % of control response to a known reference agonist for ETA (h), and cellular antagonist effect was calculated as a % inhibition of control reference agonist response for ETA. Results showing ≥50% inhibition of agonist effect are considered significant while those showing less than 25% inhibition are not considered significant. The IC50 for BQ-788 and BQ-788-B was not calculable (i.e., the dose-response curve shows less than 25% effect at the highest validated testing concentration).
Figure 5B:
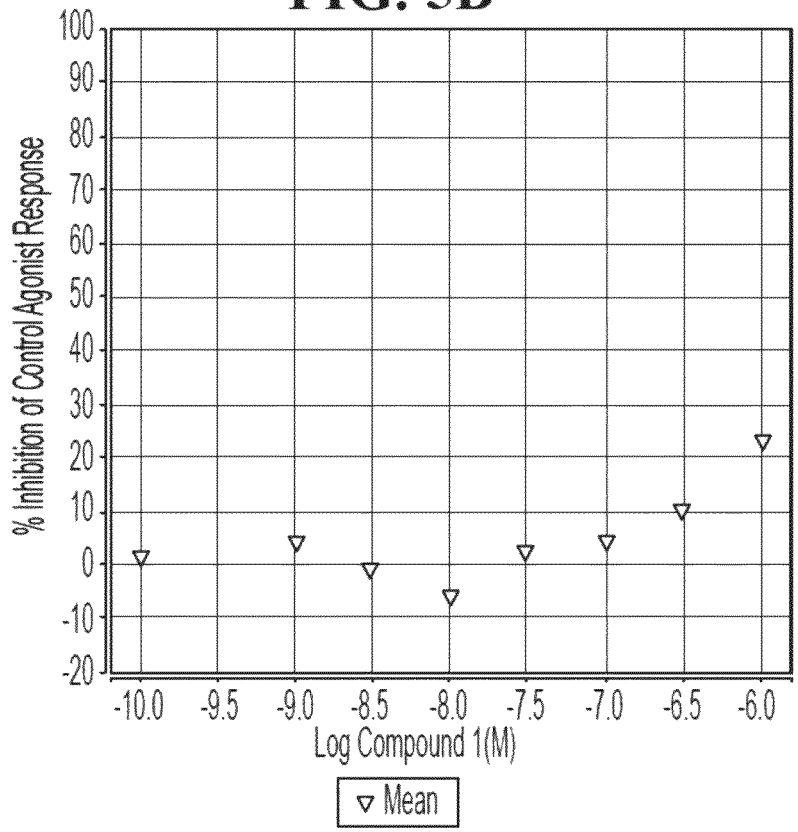

Determination of ETA (h) inhibitory effect for BQ-788 and BQ-788-B. FIGS. 5A and 5B demonstrate the determination of ETA (h) inhibitory effect for, A) BQ-788 and B) BQ-788-B (i.e., "Compound 1"). Cellular agonist effect was calculated as a % of control response to a known reference agonist for ETA (h), and cellular antagonist effect was calculated as a % inhibition of control reference agonist response for ETA. Results showing ≥50% inhibition of agonist effect are considered significant while those showing less than 25% inhibition are not considered significant. The IC50 for BQ-788 and BQ-788-B was not calculable (i.e., the dose-response curve shows less than 25% effect at the highest validated testing concentration).

Figure 6:
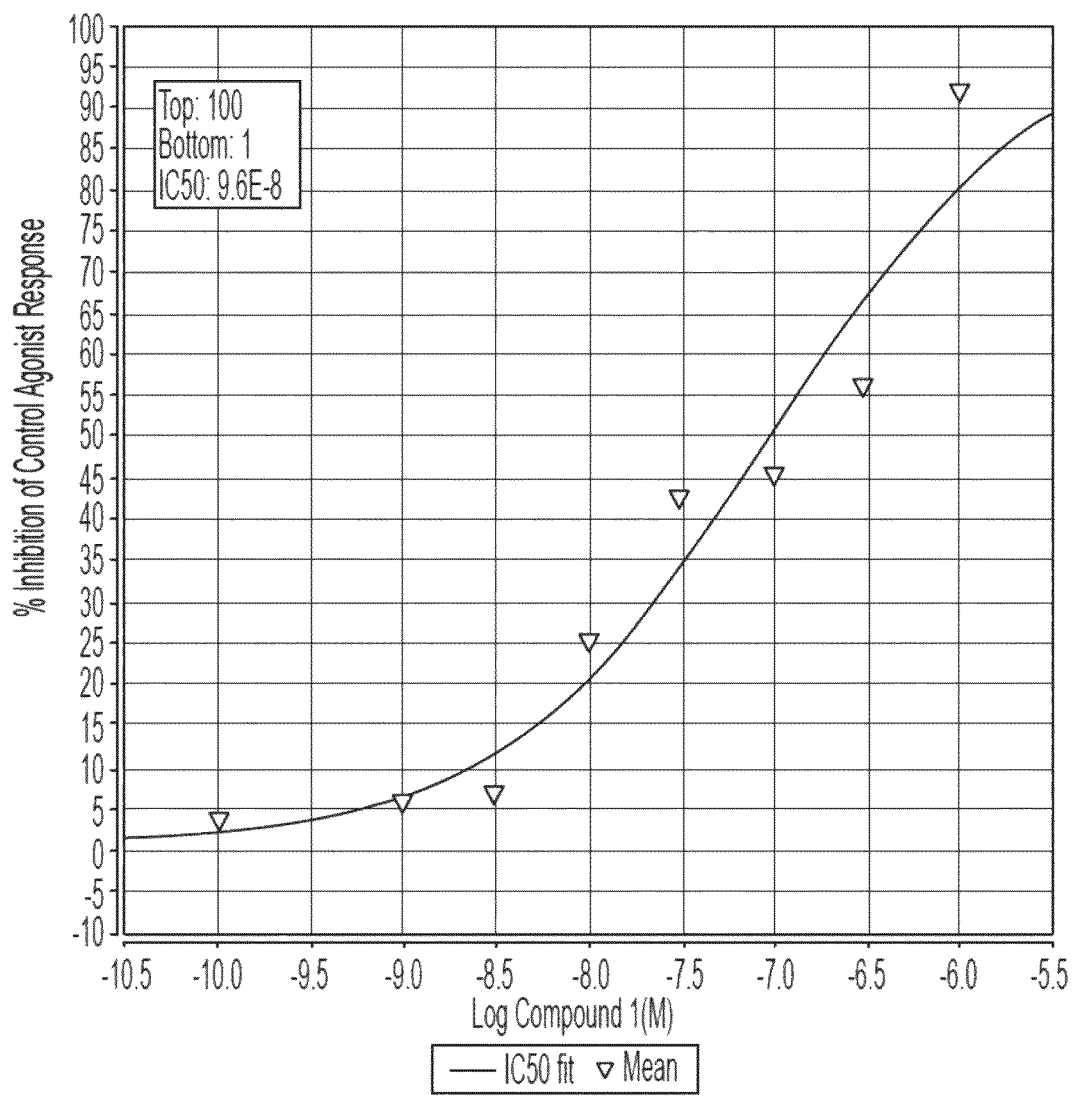
FIG. 6 shows that specifically deuterated ETRB antagonists inhibit melanoma growth and metastasis and induction of apoptosis in melanoma tumor cells. Cellular agonist effect was calculated as a % of control response to a known reference agonist for ETB (h), and cellular antagonist effect was calculated as a % inhibition of control reference agonist response for ETB. Results showing ≥50% inhibition of agonist effect are considered significant while those showing less than 25% inhibition are not considered significant. The IC50 for BQ-788 was 5.1E-08 M and the Kd was 1.3E-08; while the IC50 for the specifically deuterated compound is 9.6E-08 M and a Kd of 2.5E-08.

Determination of ETBR inhibitory effect for specifically deuterated ETBR antagonists. FIG. 6 demonstrates that specifically deuterated ETBR antagonists inhibit melanoma growth and metastasis, and induce apoptosis in melanoma tumor cells. Cellular agonist effect was calculated as a % of control response to a known reference agonist for ETB (h), and cellular antagonist effect was calculated as a % inhibition of control reference agonist response for ETB. Results showing ≥50% inhibition of agonist effect are considered significant while those showing less than 25% inhibition are not considered significant. The IC50 for a non-deuterated ETRB antagonist was 5.1E08 M and the Kd was 1.3E-08; while the IC50 for specifically deuterated ETRB antagonists were 9.6E-08 M and a Kd of 2.5E-08. Surprisingly, in PK studies in vivo, the specifically deuterated ETRB antagonists demonstrated enhanced biologic activity relative to the non-deuterated counterpart.

Figure 7:
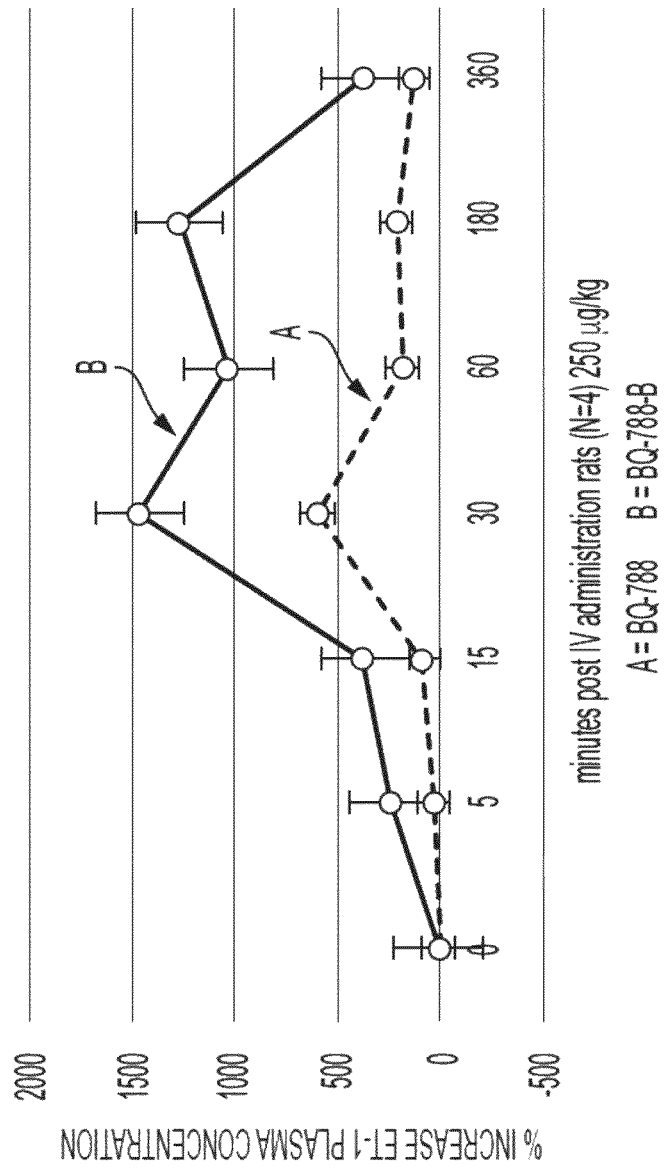
FIG. 7 shows that BQ-788-B, a specifically deuterated ETRB antagonist demonstrates enhanced biological activity relative to BQ-788. BQ-788-B demonstrates a prolonged peak out to about 3 hours as compared to BQ-788, which demonstrates a transient peak at about 30 minutes. The IC50 for BQ-788-B is 9.6E-08 M (MW=665.37). The IC50 for BQ-788 is 5.6E-08 (MW=663.78).

Plasma concentrations of BQ-788 versus BQ-788-B. FIG. 7 illustrates that BQ-788-B (curve "B"), a deuterated analog of BQ-788, demonstrates enhanced plasma concentrations relative to BQ-788. Briefly, rats (N=4 animals per timepoint) were administered either BQ-788 or the deuterated form, BQ-788-B at a dose of 250 µg/kg via IV infusion. Plasma samples were collected at various time points and ET-1 ELISA performed. BQ788 and BQ788-B are peptide drugs that are rapidly degraded in plasma and thus drug levels are difficult to detect directly. However, when BQ788 binds ETBR, this results in an increase in plasma concentrations of ET-1, the ligand for ETBR. As such, plasma levels of ET-1 are commonly used as an indirect measure of BQ-788 biologic activity. Significantly, the deuterated compound BQ-788-B demonstrates an enhanced duration and amplitude of response relative to the undeuterated form as exemplified by the prolonged peak out to about 3 hours as compared to BQ-788, which demonstrates a transient peak at about 30 minutes. The IC50 for BQ-788-B is 9.6E-08 M (MW=665.37). The IC50 for BQ-788 is 5.6E-08 (MW=663.78).

BQ-788-B in combination with anti-PD1 demonstrates synergistic results. Dual combination of specifically deuterated compounds and immunotherapeutics (FIG. 8), result in superior efficacy relative combinations with approved cancer drugs. The syngenic melanoma model V600E+ (BRAF mutated) SM1 tumor model was used in C57BL/6 mice to assess efficacy of deuterated ETRB antagonists in combination with immunotherapeutics ("B+P") as compared to a standard treatment, dabrafenib with anti-PD1 ("D+P"). Previous studies have indicated that V600E+ model demonstrates no efficacy for anti-PD1 as a single agent (and little tumor infiltrating lymphocytes (TILs)). In this study 6-8 week old female C57BL/6 mice were inoculated with SM1 tumor fragments (TME* components present). Dosing was initiated when tumors were 150 mm3. The general dosing schemes were as follows: dabrafenib (30 mg/kg daily by oral gavage), immunotherapeutic 10 mg/kg Q4D IP beginning 2 days after dabrafenib), deuterated ETRB antagonist (4 µg administered QOD IV beginning 2 days after dabrafenib). Tumors were measured three times per week, and the study was terminated after 21 days of dosing and IHC analysis of tumors was performed. The dual combination of the immunotherapeutic and the deuterated ETRB antagonist induced tumor shrinkage below baseline. In stark contrast, a standard combination of dabrafenib and the immunotherapeutic failed to shrink tumors but demonstrated intermediate tumor growth inhibition. IHC analysis of tumors treated with immunotherapeutics and deuterated ETRB antagonists revealed that tumors had been eradicated leaving only residual adipose tissue. In sum, the combination of immunotherapeutic compounds with specifically deuterated ETRB antagonists as described herein provided significant improvement against tumor growth relative to the existing therapeutic paradigm.

Figure 8:
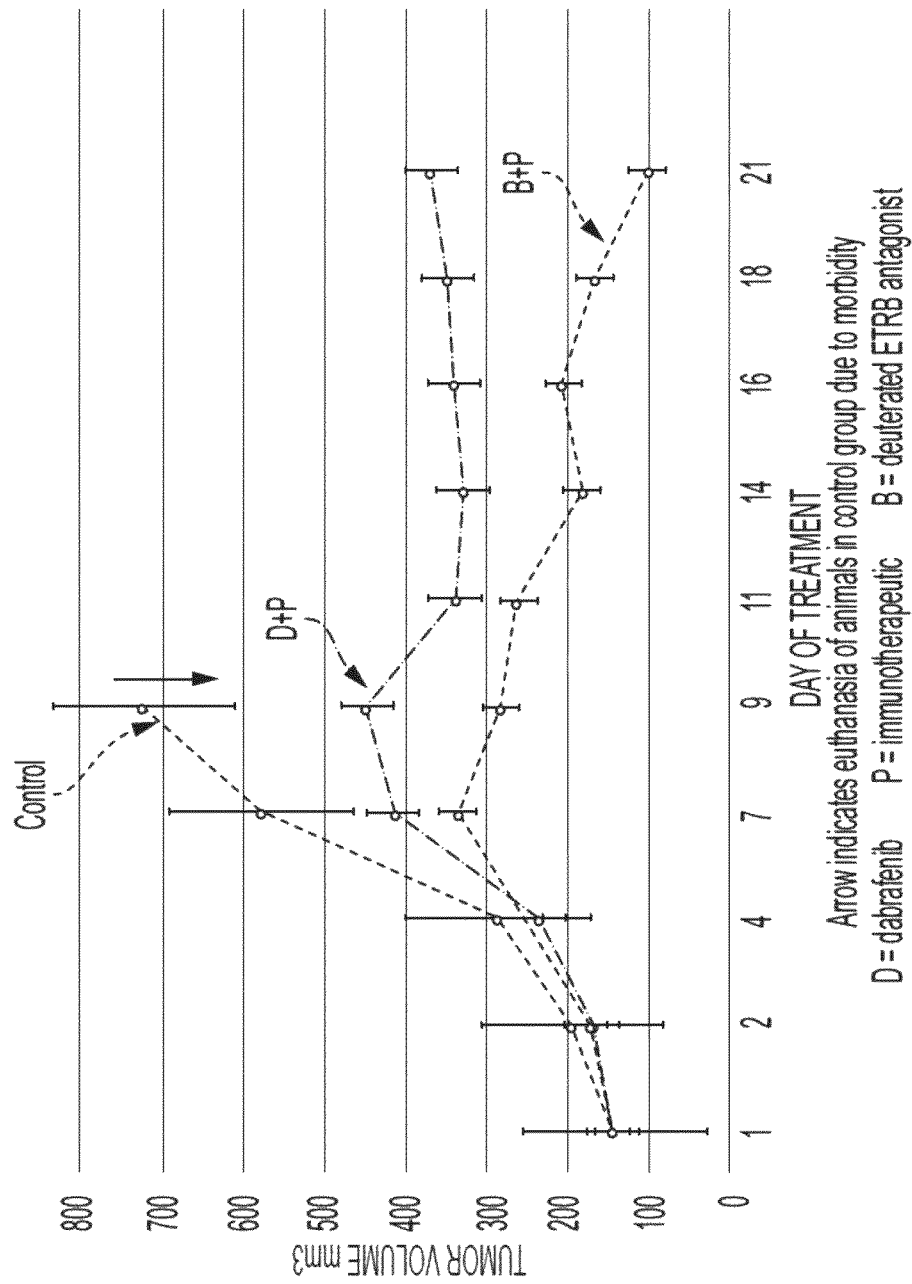
FIG. 8 shows that a dual combination of specifically deuterated ETRB antagonists and an immunotherapeutic results in superior efficacy relative to current standard drug combinations. The syngeneic melanoma model V600E+ (BRAF mutated) SM1 tumor model was used in C57BL/6 mice to assess efficacy of the specific deuterated ETRB antagonist in combination with the immunotherapeutic ("B+P") as compared to a standard of treatment, dabrafenib with anti-PD1 ("D+P").
Figure 9:
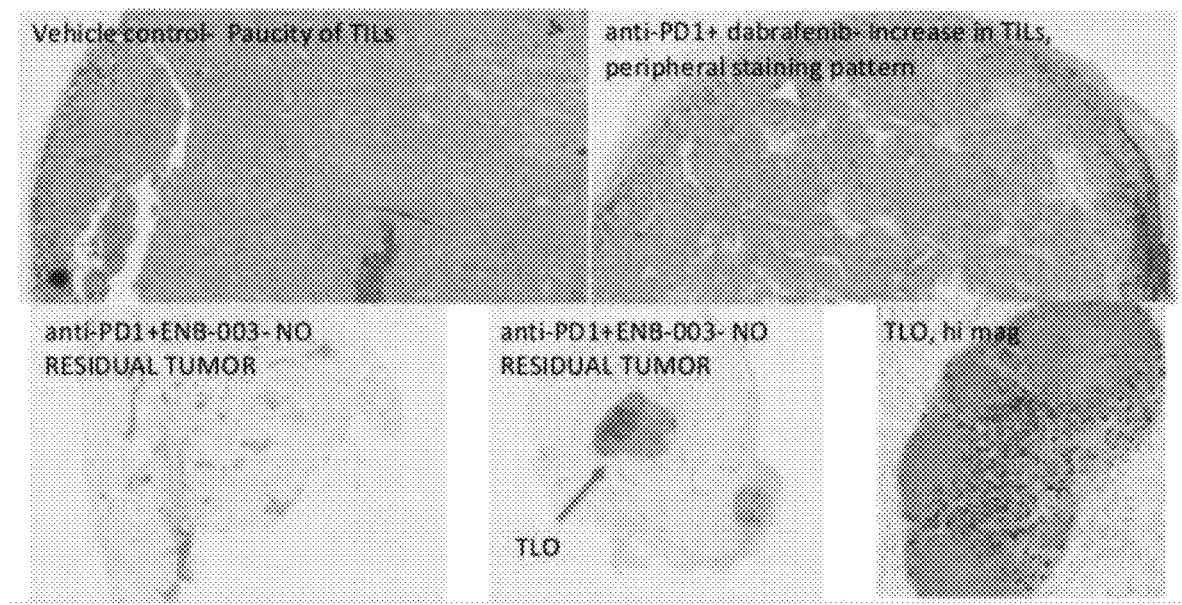
FIG. 9 shows that a dual combination of the specifically deuterated ETRB antagonist BQ-788-B and immunocheckpoint inhibitors (e.g. anti-PD1) eradicates tumors. Histological examination of V600E+ melanoma tumor cells implanted into C57BL/6 mice 21 days after treatment as indicated in FIG. 8. BQ-788-B and immunocheckpoint inhibitors in combination eradicated the tumors in 21 days, promoted robust infiltration by CD8+ lymphocytes (TILs), and induced tertiary lymphoid organ (TLO) formation.

Dual combination BQ-788-B and immunocheckpoint inhibitors eradicates tumors. FIG. 9 demonstrates the results of histological examination of V600E+ melanoma tumor cells implanted into C57BL/6 mice 21 days after treatment as indicated in FIG. 8. The specifically deuterated compound BQ-788-B and immunocheckpoint inhibitors (e.g. anti-PD1, anti-PD1, anti-CTLA) combination therapy eradicated the tumors in 21 days, promoted robust infiltration by CD8+ lymphocytes (TILs), and tertiary lymphoid organ (TLO) formation. TIL infiltration is exemplified by the dark punctate staining. TLOs are functionally equivalent to lymph nodes, produce tumor-specific T- and B-cells, and induce long lasting anti-tumor immunity.

Intratumoral TLO formation induced by combination therapy including anti-PD1 and BQ-788-B. FIG. 10 demonstrates the histological examination of V600E+ melanoma tumor cells implanted into C57BL/6 mice 21 days after treatment as indicated in FIG. 8 with BQ-788-B and anti-PD1 combination therapy. The staining of CD8+, CD4+ and Treg (FoxP3) lymphocytes (dark punctate staining) indicates that the combination therapy promotes strong mobilization of lymphocytes to the tumor, which is associated with tumor eradication and positive patient outcomes.

Figure 12:
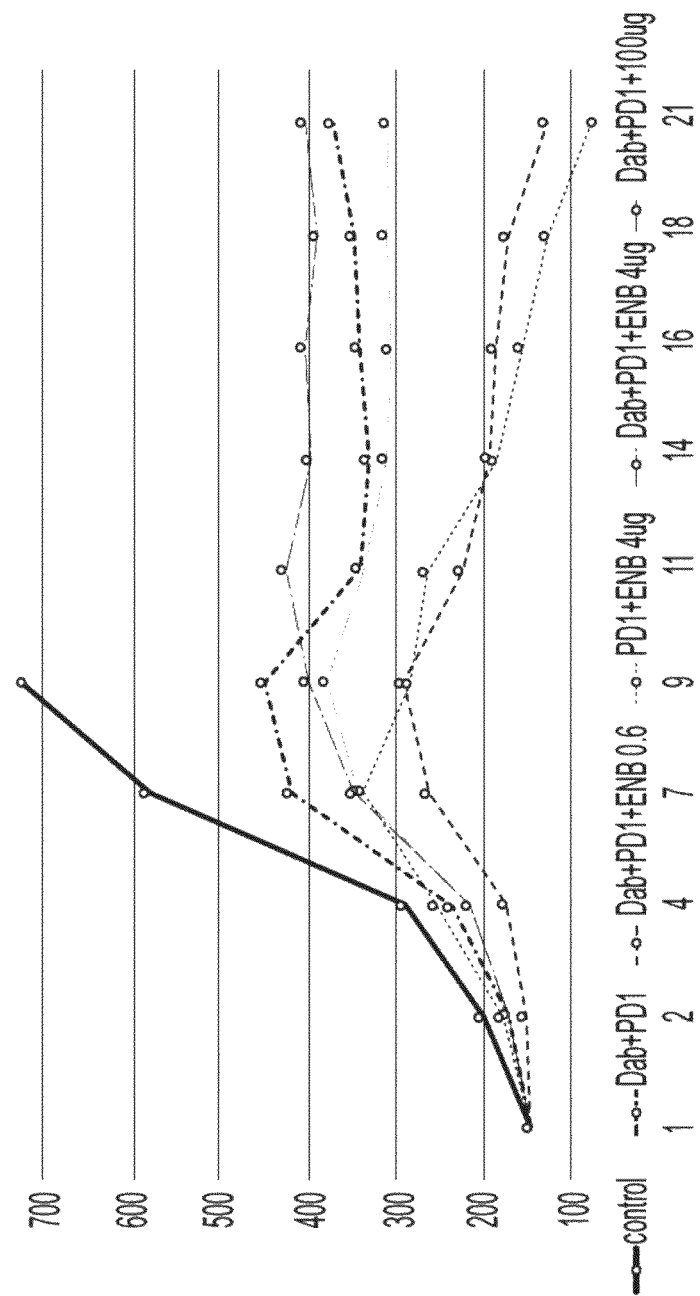
FIG. 12 shows that the inclusion of the specifically deuterated ETRB antaonist BQ-788-B with the immunocheckpoint inhibitor anti-PD1 restores sensitivity to anti-PD1. The addition of dabrafenib to anti-PD1/BQ-788-B combination impairs efficacy, possibly due to dabrafenib's ability to increase Tregs and tumor-associated macrophages (TAMs).

Intratumoral (internal) TLO formation associated with treatment with BQ-788-B. FIG. 11 provides table summaries of the results obtained with combination therapies (two- and three-part), TLO formation and efficacy for tumor eradication. The model system tested is as described for FIG. 8. The combinations included dabrafenib+anti-PD1 ("D+P"); dabrafenib+anti-PD1+BQ-788-B at 0.6 µg ("D+P+B(0.6 µg)"); dabrafenib+anti-PD1+BQ-788-B at 4.0 µg ("D+P+B(4.0 µg)"); dabrafenib+anti-PD1+BQ-788-B at 100 µg ("D+P+B (100 µg)"); and anti-PD1+BQ-788-B at (4.0 µg) ("P+B(4.0 µg)"). The data indicate that (i) internal TLO formation is associated with tumor eradication; and (ii) the combination of anti-PD1 antibody and BQ-788-B was most frequently associated with intratumoral TLO formation and tumor reduction. FIG. 12 presents the efficacy results as a function of tumor volume (mm3). The inclusion of BQ-788-B with anti-PD1 is synergistic and appears to help restore sensitivity to anti-PD1. The addition of dabrafenib to anti-PD1/BQ-788-B combination impairs efficacy, possibly due to dabrafenib's ability to increase Tregs and tumor-associated macrophages (TAMs).

Figure 13:
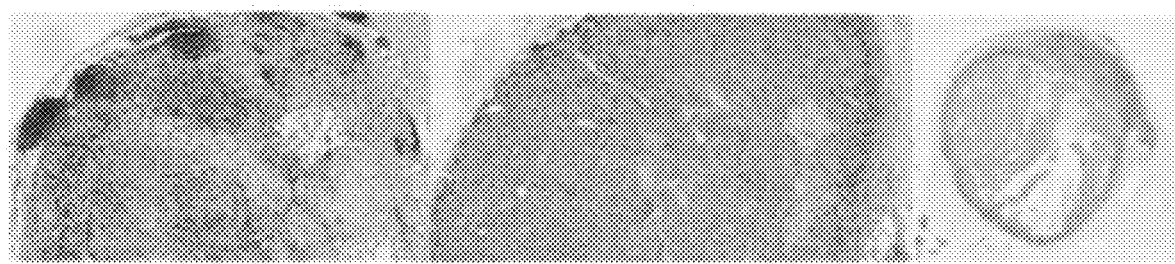
FIG. 13 shows that specifically deuterated compound BQ-788-B at 0.6 μg in combination with immunocheckpoint inhibitor (e.g. anti-CTLA, anti-PD-L1, or anti-PD1) and dabrafenib promotes diffuse CD8+ TIL staining. Histological examination of V600E+ melanoma tumor cells implanted into C57BL/6 mice 21 days after treatment as indicated in FIG. 8 with the respective combination therapy. The diffuse distribution of CD8+ TIL staining (dark punctate staining in "D+P+B(0.6 μg)") appears to be associated with higher efficacy as compared to those with peripheral distribution of TILs (see "D+P+B(4.0 μg)" and "D+P+B(100 μg)").

BQ-788-B at 0.6 µg in combination with immunocheckpoint inhibitors and dabrafenib promotes diffuse CD8+ TIL staining. FIG. 13 shows demonstrates the histological examination of V600E+ melanoma tumor cells implanted into C57BL/6 mice 21 days after treatment as indicated in FIG. 8 with the respective combination therapy. The diffuse distribution of CD8+ TIL staining (dark punctate staining) appears to be associated with higher efficacy as compared to those with peripheral distribution of TILs.

Thus, specifically deuterated forms of BQ-788 as described herein, e.g., BQ-788-A BQ-788-B, BQ-788-C and others described herein, demonstrate synergistic activity with anti-oncologic agents in a preclinical melanoma model in which anti-PD1 lacks any efficacy as a single agent. Tumor reduction or eradication correlates well with intratumoral TLO formation or neogenesis, and diffuse infiltration pattern of TILs rather than tumor-peripheral TIL distribution. TLO neogenesis has prognostic implications and correlates will with increased patient survival. The dual combination of specifically deuterated ETBR antagonists and anti-oncologic agents is superior to other dual and triple combinations in terms of (i) anti-tumor efficacy; (ii) low anticipated toxicity (based upon established safety profile of parent compound in humans); and (iii) overall treatment cost (relative to triple therapies). In addition, IV administration allows for a 2-3 order of magnitude dose reduction relative to IP or PO administration (e.g. typical doses of 200-600 µg BQ788 vs. 0.6-4.0 µg deuterated BQ-788).

Example 3. Treatment of Melanoma in a Human Subject

A human patient suffering melanoma, e.g., malignant melanoma or metastatic melanoma, is administered compounds or pharmaceutical compositions according to a method for treatment disclosed herein. The treatment cures the patient or ameliorates the patient's one or more symptoms such as a sore, spread of pigment from the border of a spot into surrounding skin, redness or a new swelling beyond the border of the mole, change in sensation, such as itchiness, tenderness, or pain, or change in the surface of a mole—scaliness, oozing, bleeding, or the appearance of a lump or bump.

Example 4. Treatment of a Malignant Solid Tumor in a Human Subject

A human patient suffering a malignant solid tumor, e.g., pancreatic tumor, ovarian tumor, sarcomas, carcinomas, and lymphomas, is administered compounds or pharmaceutical compositions according to a method for treatment disclosed herein. The treatment reduces a tumor volume or mass, or eradicates the tumor in the patient.

Example 5. Treatment of a Pancreatic Cancer in a Human Subject

A human patient suffering a pancreatic cancer is administered compounds or pharmaceutical compositions according to a method for treatment disclosed herein. The treatment cures the patient or ameliorates the patient's one or more symptoms such as Jaundice, light-colored stools, dark urine, pain in the upper or middle abdomen and back, weight loss, appetite loss, or fatigue.

Example 6. Treatment of an Ovarian Cancer in a Human Subject

A human patient suffering an ovarian cancer is administered compounds or pharmaceutical compositions according to a method for treatment disclosed herein. The treatment cures the patient or ameliorates the patient's one or more symptoms for example: abdominal bloating, indigestion or nausea, changes in appetite such as a loss of appetite or feeling full sooner, pressure in the pelvis or lower back, a frequent or urgent need to urinate and/or constipation, changes in bowel movements, increased abdominal girth, tiredness or low energy, or changes in menstruation.

Example 7. Treatment of Squamous Cell Carcinoma in a Human Subject

A human patient suffering squamous cell carcinoma is administered compounds or pharmaceutical compositions according to a method for treatment disclosed herein. The treatment cures the patient or ameliorates the patient's one or more symptoms such as firm red nodule, flat sore with a scaly crust, new sore or raised area on an old scar or ulcer, rough scaly path on a lip or inside a mouth, scaly red patches, open sores, or warts or elevated growths with a central depression on or in anus on genitals.

Example 8. Treatment of Glioblastoma in a Human Subject

A human patient suffering glioblastoma is administered compounds or pharmaceutical compositions according to a method for treatment disclosed herein. The treatment cures the patient, reduces or eradicates brain tumor, or ameliorates the patient's one or more symptoms such as headache, nausea, vomiting, memory loss, drowsiness, blurred vision, change to personality, mood, or concentration, localized neurological problems, or seizure.

While some embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a tumor in a subject in need thereof, comprising administering to the subject (a) a deuterated endothelin B-receptor (ETBR) antagonist according to Structure

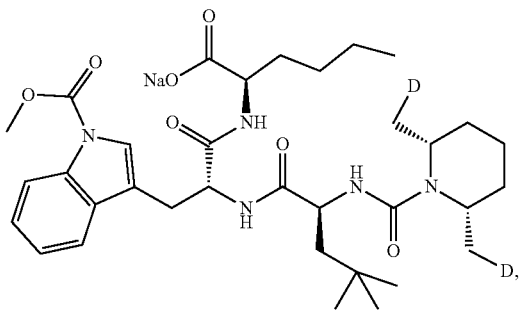

and (b) a PD1 inhibitor.

2. The method of claim 1, wherein administration of the ETBR antagonist and the PD1 inhibitor induces the growth and/or formation of a tertiary lymphoid organ (TLO) in the tumor.

3. The method of claim 1, wherein administration of the ETBR antagonist and the PD1 inhibitor increases Tumor Infiltrating Lymphocyte (TIL) infiltration of the tumor.

4. The method of claim 1, wherein immune cell infiltration of the tumor is increased.

5. The method of claim 1, wherein the volume and/or mass of the tumor is reduced.

6. The method of claim 1, wherein the PD1 inhibitor is an anti-PD1 antibody.

7. The method of claim 6, wherein the anti-PD1 antibody is pidilizumab, nivolumab, pembrolizumab or any combination thereof.

8. The method of claim 6, wherein the ETBR antagonist and the anti-PD1 antibody are administered at different times.

9. The method of claim 8, wherein the ETBR antagonist is administered 2, 3, 4, or 5 times frequently as the anti-PD1 antibody.

10. The method of claim 8, wherein the ETBR antagonist is administered 3 times as frequently as the anti-PD1 antibody.

11. The method of claim 1, wherein the tumor is selected from melanoma, squamous cell carcinoma, glioblastoma, pancreatic cancer, colon cancer, breast cancer, ovarian cancer and prostate cancer.

12. The method of claim 11, wherein the melanoma is metastatic melanoma.

13. The method of claim 11, wherein the squamous cell carcinoma is metastatic squamous cell carcinoma.

* * * * *